US008034345B2

(12) United States Patent
Suzuki et al.

(10) Patent No.: US 8,034,345 B2
(45) Date of Patent: Oct. 11, 2011

(54) ANTI-PCI ANTIBODY FOR REGULATING LIVER REGENERATION/REPAIR

(75) Inventors: Koji Suzuki, Mie (JP); Hiroyuki Saito, Shizuoka (JP)

(73) Assignees: Chugai Seiyaku Kabushiki Kaisha, Tokyo (JP); Mie University, Mie (JP)

( * ) Notice: Subject to any disclaimer, the term of this patent is extended or adjusted under 35 U.S.C. 154(b) by 454 days.

(21) Appl. No.: 11/577,157

(22) PCT Filed: Oct. 11, 2005

(86) PCT No.: PCT/JP2005/018675
§ 371 (c)(1),
(2), (4) Date: Aug. 4, 2008

(87) PCT Pub. No.: WO2006/041048
PCT Pub. Date: Apr. 20, 2006

(65) Prior Publication Data
US 2009/0035320 A1 Feb. 5, 2009

(30) Foreign Application Priority Data
Oct. 15, 2004 (JP) ................................ 2004-302129
Jul. 26, 2005 (JP) ................................ 2005-215376

(51) Int. Cl.
*A61K 39/395* (2006.01)
(52) U.S. Cl. ................ 424/145.1; 424/130.1; 424/133.1
(58) Field of Classification Search ........................ None
See application file for complete search history.

(56) References Cited

U.S. PATENT DOCUMENTS

| 6,593,291 B1 | 7/2003 | Green et al. |
| 2006/0167230 A1 | 7/2006 | Koga et al. |
| 2009/0170760 A1 | 7/2009 | Suzuki |

FOREIGN PATENT DOCUMENTS

| JP | 63-233927 | 9/1988 |
| JP | 2002-000273 | 1/2002 |

OTHER PUBLICATIONS

USPTO Restriction Requirement in U.S. Appl. No. 11/911,754, dated Dec. 2, 2009, 5 pages.
Fish & Richardson P.C., Response to Restriction Requirement dated Dec. 2, 2009 in U.S. Appl. No. 11/911,754, filed Dec. 23, 2009, 1 page.
USPTO Non-Final Office Action in U.S. Appl. No. 11/911,754, dated Feb. 19, 2010, 12 pages.
Asanuma et al., "Protein C inhibitor inhibits breast cancer cell growth, metastasis and angiogenesis independently of its protease inhibitory activity," Int. J. Cancer, 121:955-965 (2007).
Kuhn et al., "Elicidating the structural chemistry of glycosaminoglycan recognition by protein C inhibitor", Proc. Natl. Acad. Sci. USA 87:8506-8510, 1990.
Shirk et al., "Role of the H helix in heparin binding to protein C inhibitor", The Journal of Biological Chemistry 269(46):28890-28895, 1994.
Stief et al., "Evidence for identity of PCI and plasminogen activator inhibitor 3", Biol. Chem. Hoppe-Seyler 368:1427-1433, 1987.
Stump et al., "Purification and characterization of a novel imhibitor of urokinase from human urine", The Journal of Biological Chemistry 261(27):12750-12766, 1986.
Suzuki et al., "Protein C inhibitor", The Journal of Biological Chemistry 258(1):163-168, 1983.
Suzuki et al., "Characterization of a cDNA for human protein C inhibitor", The Journal of Biological Chemistry 262(2):611-616, 1987.
Fair and Marlar, "Biosynthesis and Secretion of Factor VII, Protein C, Protein S, and the Protein C Inhibitor From a Human Hepatoma Cell Line," *Blood*, 67(1):64-70 (1986).
Hamada et al., "Protein C inhibitor regulates hepatocyte growth factor activator-mediated liver regeneration in mice," *Gut*, 57:365-373 (2008).
European Search Report for App. Ser. No. EP 05 79 3705, dated Feb. 12, 2009, 5 pages.
Japanese Patent Office, International Search Report for App. Ser. No. PCT/JP2006/308095, mailed Jul. 25, 2006, 5 pages.
International Preliminary Report on Patentability for App. Ser. No. PCT/JP2006/308095, dated Oct. 23, 2007, 6 pages.
Akita et al., "Protein C Inhibitor (PCI) inhibits invasion and matastasis of melanoma cells", Japanese Journal of Thrombosis and Hemostasis, 14(5):443, 2003.
Elisen et al., "Protein C Inhibitor Acts As A Procoagulant by Inhibiting the Thrombomodulin-Induced Activation of Protein C in Human Plasma", Blood, 91:1542-1547, 1998.
Francis Jr. et al., "Behaviour of Protein C Inhibitor in Intravascular Coagulation and Liver Disease", Thromb Haemostas, 52:71-74, 1984.
Hayashi et al., "Characterization of a Novel Human Protein C Inhibitor (PCI) Gene Transgenic Mouse Useful for Studying the Role of PCI in Physiological and Pathological Conditions", Journal of Thrombosis and Haemostas, 2:949-961, 2004.
Jackson et al., "Assessment of the interaction between urokinase and reactive site mutants of protein C inhibitor", Journal of Protein Chemistry 16(8):819-828, 1997.
Joyce et al., "Gene Expression Profile of Antithrombotic Protein C Defines New Mechanisms Modulating Inflammation and Apoptosis", The Journal of Biological Chemistry, 276:11199-11203, 2001.
Kaido et al., "Expressions of Molecules Associated with Hepatocyte Growth Factor Activation After Hepatectomy in Liver Cirrhosis", Hepato-gastroenterology, 51:547-551, 2004.
Marlar et al., "Deficiency of Protein C Inhibitor in Combined factor V/VIII Deficiency Disease", J. Clin. Invest., 66:1186-1189, 1980.
Suzuki et al., "Mechanism of Inhibition of Activated Protein C", J. Biochem. 95:187-195, 1984.

(Continued)

*Primary Examiner* — Sharon Wen
(74) *Attorney, Agent, or Firm* — Fish & Richardson P.C.

(57) ABSTRACT

The present invention relates to uses of PCI, which inhibits HGFa activity, and to uses of anti-PCI antibodies, which neutralize HGFa inhibition; and to agents for regulating and controlling tissue regeneration and/or repair, with PCI as an active ingredient; and to agents for enhancing tissue regeneration and/or repair, with anti-PCI antibodies as active ingredients (particularly, anti-PCI antibodies with the action of neutralizing PCI (anti-PCI neutralizing antibodies)).

18 Claims, 16 Drawing Sheets

OTHER PUBLICATIONS

Suzuki et al., "Protein C Inhibitor Plays a Role as a Potent Regulator of Activated Hepatocyte Growth Factor Activator", Journal of Thrombosis and Haemostasis, 3(Suppl. 1):Abstract No. OR001, Abstracts from XXth ISTH Congress, Aug. 2005.

Suzuki, "Protein C Inhibitor (PAI-3): Structure and Multi-Function", Fibrinolysis and Proteolysis, 14:133-145, 2000.

Taylor Jr. et al., "DEGR-Factor Xa Blocks Disseminated Intravascular Coagulation Initiated by *Escherichia coli* Without Preventing Shock or Organ Damage", Blood, 78:364-368, 1991.

Taylor Jr. et al., "Protein C Prevents the Coagulopathic and Lethal Effects of *Escherichia coli* Infusion in the Baboon", J. Clin. Invest., 79:918-925, 1987.

Wakita et al., "Regulation of carcinoma cell invasion by protein C inhibitor whose expression is decreased in renal cell carcinoma", Intl. J. Cancer 108(10):516-523, 2004.

Xue et al., "Hepatocyte Growth Factor Gene Therapy Accelerates Regeneration in Cirrhotic Mouse Livers After Hepatectomy", Gut, 52:694-700, 2003.

| | | CDR1 | | CDR2 | |
|---|---|---|---|---|---|
| PC23D8 | EVQLQQSGAELVKPGASVKLSCTASGFDIK | DTFMH | WVKQRPEQGLEWIG | RIDYVNGNTKYDPKFQG | |
| PC19G8 | EVQLQQSGAELVKPGASVKLSCTASGFDIK | DTFMH | WVKQRPEQGLEWIG | RIDYVNGNTKYDPKFQG | |
| PC23A7 | EVQLQQSGAELVKPGASVKLSCTASGFDIR | DTFMH | WVKQRPEQGLEWIG | RIDLVNVNTKYDPNFQD | |
| PC39C6 | EVQLQQSGAELVRPGALVKLSCKASGFNIK | DYYIH | WVKQRPEQGLEWIG | RIDLEKGNIIYDPKFQG | |
| PC31F1 | EVKLLESGGGLVQPGSLKLSCAASGFDFS | RYWMS | WVRQAPGKGLEWIG | EINPDSSTINYTPSLKD | |
| PC30G1 | EVKLLESGGGLVQPGGSLKFSCEASGFDFS | RYWMS | WVRQAPGKGLEWIG | EINPDSSTITYTSSLKD | |
| PC31E2 | QVQLQQSGAELVKPGASVKMSCKAFGYTFT | TYPIE | WMKQNFIGKSLEWIG | KFHPDNDDTNYNEKFKG | |

| | | CDR3 | | | |
|---|---|---|---|---|---|
| PC23D8 | KAITIGDTSSNTAYLQLSSLTSEDTAVYYCAR | GGYDVREFAY | WGQGTLVTVSA | (SEQ ID NO : 8) |
| PC19G8 | KATITGDTSSNTAYLQLSSLTSEDTAVYYCAR | GGYDVREFAY | WGQGTLVTVSA | (SEQ ID NO : 9) |
| PC23A7 | RATITADTSSNTAYLQLTSLTSEDTAVYYCAR | GGYDVREFAY | WGQGTLVTVSA | (SEQ ID NO : 10) |
| PC39C6 | KDNITADTSSNTAYLQLSSLTSEDTAVYYCAR | GGYDVPSFAY | WGQGTLVTVSA | (SEQ ID NO : 11) |
| PC31F1 | KFIISRDNAKKTLYLQMNKVRSEDTALYYCAR | FFYYGTPDY | WGQGTTLTVSSA | (SEQ ID NO : 12) |
| PC30G1 | RFIISRDNAKNTVYLQMSKVRSEDTALYYCAR | LFYYGTPDY | WGQGTTLTVSSA | (SEQ ID NO : 13) |
| PC31E2 | KAKLTVEKSSSTVYLELSRLTSDDSAVYYCAR | GHDYDYGMDY | WGQGTSVTVSSA | (SEQ ID NO : 14) |

FIG. 6

|        | | CDR1 | | CDR2 | |
|--------|--|------|--|------|--|
| PC23D8 | QIVLTQSPAIMSASPGEKVTITC | SATSSLIYMH | WFQQKPGSSPELMIY | STSNLASGVPA | |
| PC19G8 | QIVLTQSPAIMSASPGEKVTITC | SATSSLIYMH | WFQQKPGSSPELMIY | STSNLASGVPA | |
| PC23A7 | QIVLTQSPAIMSASPGEKVTITC | SATSSLIYMH | WFQQKPGTSPKLWIY | STSNLASGVPA | |
| PC39C6 | QIVLTQSPAIMSASPGEKVTITC | SASSSVSYMH | WFQQKPGTSPKLWIY | STSNLASGVPA | |
| PC31F1 | DIVMTQSHKFMSASVGDRVSITC | KASQDVIVAVA | WYQQKPGQSPELLIY | SASYRYTGVPD | |
| PC30G1 | DIVMTQSHKFMSTSVGDRVSITC | KASQDVIKAVA | WYQQKPGQSPKLLIY | STSYRYTGVPD | |
| PC31E2 | DIVLTQSPASLAVSLGQRATISC | KASQSVDYDGDSYLN | WYQQKPGQPPKLLIY | GASNLESGTPA | |

|        | | | CDR3 | |
|--------|--|--|------|--|
| PC23D8 | RFSGSGSGTSYSLTIISRMEAEDAATYYCQQ | RSSYPFT | FGSGTKLEIK | (SEQ ID NO : 15) |
| PC19G8 | RFSGSGSGTSYSLTIISRMEAEDAATYYCQQ | RSSYPFT | FGSGTKLEIK | (SEQ ID NO : 16) |
| PC23A7 | RFSGSGSGTSYSLTIISRMEAEDAATYYCQQ | RSSYPFT | FGSGTKLEIK | (SEQ ID NO : 17) |
| PC39C6 | RFSGSGSGTSYSLTIISRMEAEDAATYYCQQ | RSSYPFT | FGSGTKLEIK | (SEQ ID NO : 18) |
| PC31F1 | RFTGSGSGTDFTFTISSVQAEDLAVYYCQQ | HYSSPPWT | FGGGTKLEIK | (SEQ ID NO : 19) |
| PC30G1 | RFSGSGSGTDFTFTISSVQAEDLAVYYCQQ | HYSSPPWT | FGGGTKLEIK | (SEQ ID NO : 20) |
| PC31E2 | RFSGSGSGTDFTLDIHPVEEEDAATYYCQQ | SNEDPPT | FGGGTKLEIT | (SEQ ID NO : 21) |

FIG. 12
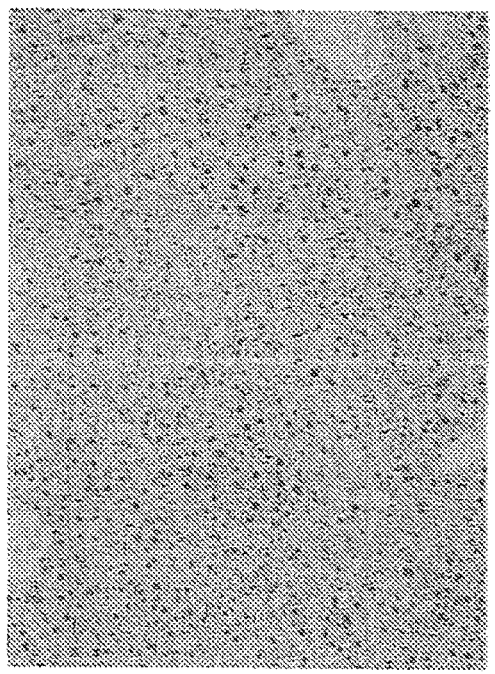
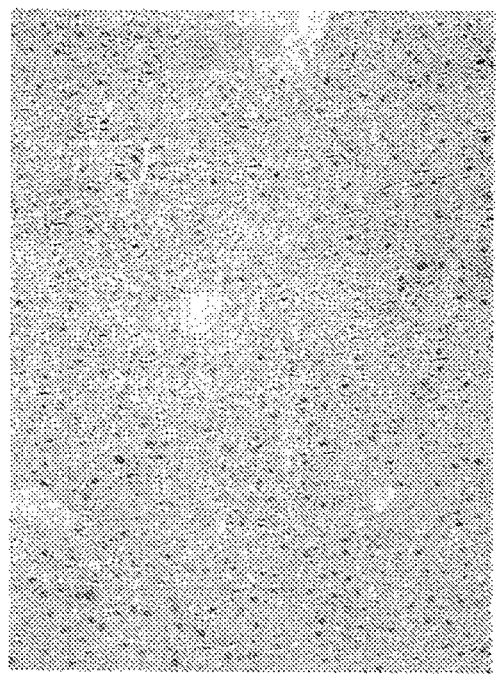
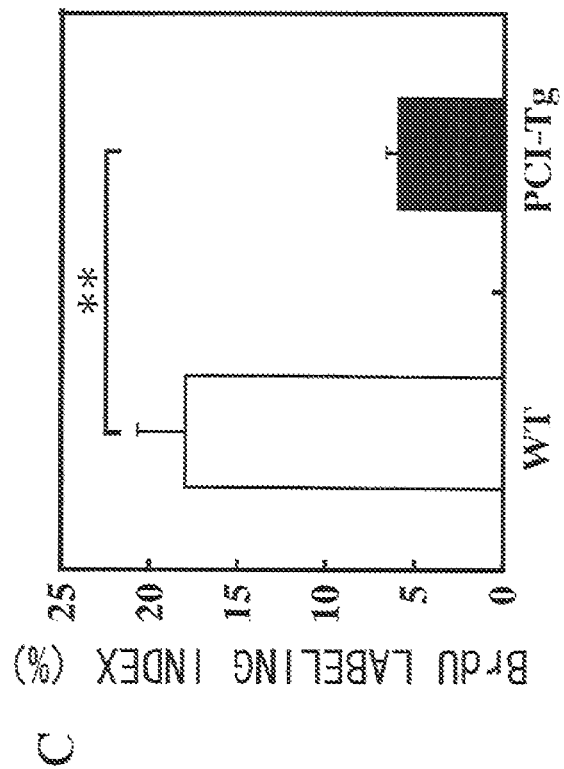

ANTI-PCI ANTIBODY FOR REGULATING LIVER REGENERATION/REPAIR

CROSS-REFERENCE TO RELATED APPLICATIONS

This application is the National Stage of International Application No. PCT/JP2005/018675, filed on Oct. 11, 2005, which claims the benefit of Japanese Patent Application Serial No. 2004-302129, filed on Oct. 15, 2004, and Japanese Patent Application Serial No. 2005-215376, filed on Jul. 26, 2005. The contents of all foregoing applications are hereby incorporated by reference in their entireties.

TECHNICAL FIELD

The present invention relates to agents for regulating and controlling tissue regeneration and/or repair, which comprise protein C inhibitor (PCI) as an active ingredient, and agents for inducing or enhancing tissue regeneration and/or repair, which comprise as an active ingredient an anti-PCI antibody (particularly anti-PCI antibodies with the activity of neutralizing PCI (an anti-PCI neutralizing antibody)).

BACKGROUND ART

Hepatocyte growth factor (HGF) was isolated as a substance that enhanced hepatocyte growth, and its gene was cloned in 1989. In a model of experimental rats with 70% partial hepatectomies, HGF production in liver stromal cells and distant organs, such as lung and kidney, was reported to contribute to liver regeneration. Such liver regeneration is further enhanced in mice administered with recombinant HGF and HGF-expressing transgenic mice.

Clinical findings also show that hepatitis and hepatic disorders increase blood HGF level and that HGF activity decreases rapidly when liver regeneration is completed. HGF is thus thought to play an important role in liver regeneration. HGF is known to not only function as a regeneration factor in pathological conditions, such as drug-induced hepatitis, fulminant hepatitis, alcoholic hepatitis, and cirrhosis, but also to induce tissue regeneration in pulmonary fibrosis, nephrosclerosis, cardiac myopathy, and the like, thereby inhibiting the progression of fibrosis. Thus, HGF replacement therapy is expected to be a novel regeneration medical therapy that inhibits progression of intractable organ diseases and improves pathological conditions.

HGF is secreted as an inactive single-chain precursor. Intramolecular cleavage by HGF activator (HGFa), an activating enzyme specific to HGF, results in formation of the active two-chain HGF.

HGFa is one type of serine protease and is secreted in the form of single-chain pro-HGFa in the liver, and converted through limited proteolysis by thrombin into two-chain active HGFa.

Based on various findings, activated protein C (aPC) is thought to be effective in treating and preventing thrombosis, sepsis, and such (Non-patent Documents 1 to 3).

Protein C inhibitor (PCI) was discovered as a biological substance that inhibits the coagulation regulatory factor aPC (Non-patent Document 4). PCI irreversibly inhibits the enzymatic activity of aPC by forming an acyl enzyme complex with aPC (Non-patent Document 5). In addition, PCI also inhibits thrombin/thrombomodulin (Thr/TM) complex, which is an aPC-producing enzyme, to suppress production of aPC (Non-patent Document 6). In other words, PCI inhibits both production and activity of aPC, thereby suppressing the action of aPC. Therefore, the inhibition of PCI activity can enhance the activity of aPC produced endogenously and aPC administered exogenously, and thus can obtain an effective anti-blood coagulation action. The present inventors therefore prepared anti-PCI antibodies with the activity of neutralizing PCI, which inhibits the production and enzymatic activity of aPC (Patent Document 1). Such neutralizing antibodies suppress the blood coagulation system by enhancing the aPC activity, and are thus extremely useful for treating and preventing thrombosis. Further, when used in combination with aPC in the treatment of sepsis and such using aPC, these antibodies can be used as pharmaceutical agents that enhance aPC actions by suppressing aPC inactivation in blood.

In addition to the action described above, PCI was reported to have the action of inhibiting the HGFa activity by forming a complex with HGFa (Patent Document 2). However, whether or not PCI actually has the action of suppressing or retarding liver regeneration is unknown.

[Patent Document 1] International Patent Application Publication No. WO 04/065418 pamphlet
[Patent Document 2] Japanese Patent Application Kokai Publication No. (JP-A) 2002-273 (unexamined, published Japanese patent application)
[Non-patent Document 1] J. Biol. Chem. (2001) 276, 11199-203
[Non-patent Document 2] J. Clin. Invest. (1987) 79, 918-25
[Non-patent Document 3] Blood (1991) 78, 364-8
[Non-patent Document 4] J. Clin. Invest. (1980) 66, 1186-9
[Non-patent Document 5] J. Biochem. (1984) 95, 187-95
[Non-patent Document 6] Blood (1998) 91, 1542-7

DISCLOSURE OF THE INVENTION

Problems to be Solved by the Invention

An objective of the present invention is to provide agents for inducing or enhancing liver regeneration, with anti-PCI antibodies, particularly anti-PCI neutralizing antibodies, as active ingredients. Another objective is to provide agents for regulating liver regeneration, with PCI as an active ingredient.

Means to Solve the Problems

The present inventors discovered that PCI retarded tissue regeneration and repair in vivo, and that anti-PCI neutralizing antibodies neutralized HGFa inhibition by PCI and thus had the action of enhancing liver regeneration by canceling the suppression of active HGF formation. The inventors thus completed the present invention based on these findings. Specifically, the present invention relates to uses of PCI, which inhibits HGFa activity, and to uses of anti-PCI antibodies, which neutralize HGFa inhibition; and to agents for regulating and controlling tissue regeneration and/or repair, with PCI as an active ingredient; and to agents for inducing or enhancing tissue regeneration and/or repair, with anti-PCI antibodies as active ingredients (particularly, anti-PCI antibodies with the activity of neutralizing PCI (anti-PCI neutralizing antibodies)). Specifically, the prevent invention relates to:

[1] an agent for inducing or enhancing liver regeneration, which comprises an anti-PCI antibody as an active ingredient;
[2] a therapeutic agent for a hepatic disease, which comprises an anti-PCI antibody as an active ingredient;
[3] the agent of [1] or [2], in which the anti-PCI antibody is an antibody with the activity of neutralizing a PCI;
[4] the therapeutic agent of [2], in which the hepatic disease is hepatitis or cirrhosis;

[5] an agent for regulating liver regeneration, which comprises a PCI as an active ingredient; and

[6] the agent of [5], in which liver regeneration is regulated by retarding liver regeneration.

BRIEF DESCRIPTION OF THE DRAWINGS

FIG. 1 shows the nucleotide sequence of PCI cDNA (without tags). The nucleotide sequence of a full-length PCI gene is shown in this figure. EcoRI and BamHI recognition sequences (underlined) have been added to the 5' and 3' ends of the sequence respectively, for insertion in between the EcoRI and BamHI sites on the animal cell expression vector pCHOI. In addition, a Kozak sequence has been attached just before the initiation codon to improve transcription efficiency. The nucleotide sequence is shown in SEQ ID NO: 4, and its amino acid sequence is shown in SEQ ID NO: 5.

FIG. 2 shows the nucleotide sequence of a PCI cDNA (with a FLAG tag). The nucleotide sequence of a Flag-tagged PCI gene is shown in this figure. A Flag sequence (wavy line) has been attached to the 3' end of the full-length PCI gene by inserting the full-length PCI-encoding cDNA between the EcoRI and BamHI sites on the animal cell expression vector pCHO2-FLAG. The nucleotide sequence is shown in SEQ ID NO: 6, and its amino acid sequence is shown in SEQ ID NO: 7.

FIG. 5 shows the amino acid sequences of the H chains of each of the anti-PCI neutralizing antibodies. CDR 1, 2, and 3 are boxed. The amino acid sequences in the figure correspond to SEQ ID NOs: 8 to 14 respectively, from the top.

FIG. 6 shows the amino acid sequences of the L chains of each of the anti-PCI neutralizing antibodies. CDR 1, 2, and 3 are boxed. The amino acid sequences in the figure correspond to SEQ ID NOs: 15 to 21 respectively, from the top.

FIG. 12 is light micrographs showing BrdU-labeled hepatocytes from the remnant livers of PCI-Tg and WT mice 48 hours after partial hepatectomies. FIG. 12A shows liver section of a WT mouse 48 hours after partial hepatectomy. FIG. 12B shows liver section of a PCI-Tg mouse 48 hours after partial hepatectomy. BrdU was administered into the peritoneal cavities six hours before sacrificing the mice. DNA synthesis was detected using BrdU uptake and immunostaining using a monoclonal antibody against BrdU. FIG. 12C shows BrdU labeling index in PCI-Tg and WT mice. The data were presented as means±SD (n=3). **p<0.01, in comparison with WT mice.

DETAILED DESCRIPTION

Figure 3:
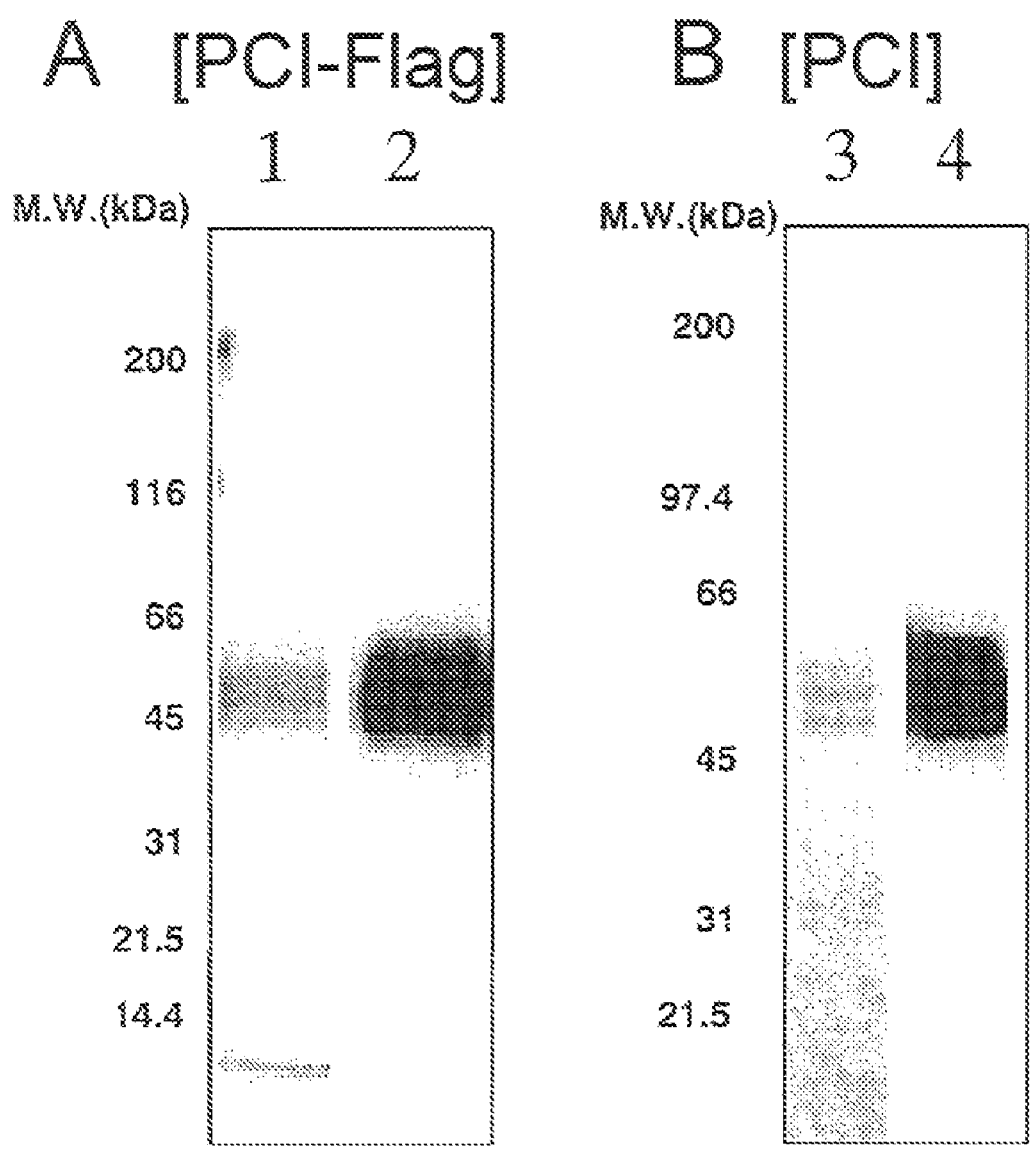
FIG. 3 shows photographs of PCI-Flag and PCI analyzed using SDS-PAGE and Western blotting. PCI-Flag (lanes 1 and 2, FIG. 3A) and non-tagged PCI (lanes 3 and 4, FIG. 3B) were fractionated by SDS-PAGE, and detected using Coomassie Blue staining (lanes 1 and 3) and Western blotting using anti-PCI antibodies (lanes 2 and 4).

1. Agents for Inducing and Enhancing Liver Regeneration

The present invention provides agents for inducing and/or enhancing liver regeneration, which comprise anti-PCI antibodies as active ingredients. Preferred anti-PCI antibodies, which are comprised in the agents for inducing and/or enhancing liver regeneration of the present invention, are antibodies with PCI-neutralizing action. PCI forms a complex with HGFa and thus inhibits the HGFa action of intramolecularly cleaving the HGF precursor. The anti-PCI antibodies to be used in the present invention are those that significantly inhibit such PCI activities. The anti-PCI antibodies of the present invention may be monoclonal antibodies (including full-length monoclonal antibodies) or polyclonal antibodies, or mutants thereof. Monoclonal antibodies are preferred because they are stably produced as homogeneous antibodies.

Herein, "monoclonal antibody" refers to antibodies obtained from groups of substantially homogeneous antibodies, that is, antibody groups wherein the antibodies constituting the group are homogeneous except for naturally occurring mutants that exist in small amounts. Monoclonal antibodies are highly specific and interact with a single antigenic site. Furthermore, each monoclonal antibody targets a single antigenic determinant (epitope) on an antigen, as compared to common polyclonal antibody preparations that typically contain various antibodies against a range of antigenic determinants. In addition to their specificity, monoclonal antibodies are advantageous in that they are produced from hybridoma cultures not contaminated with other immunoglobulins. The qualifier "monoclonal" indicates a characteristic of antibodies obtained from a substantially homogeneous group of antibodies, and does not mean antibodies produced by a particular method. For example, a monoclonal antibody to be used in the present invention can be produced by methods not limited to hybridoma methods (Kohler and Milstein, Nature (1975) 256, 495) or recombination methods (U.S. Pat. No. 4,816, 567). The monoclonal antibodies used in the present invention can also be isolated from phage antibody libraries (Clackson et al., Nature (1991) 352, 624-8; Marks et al., J. Mol. Biol. (1991) 222, 581-97). The monoclonal antibodies of the present invention particularly comprise "chimeric" antibodies (immunoglobulins), wherein a part of a heavy (H) chain and/or light (L) chain is derived from a specific species or specific antibody class or subclass, and the remaining portion of the chain is derived from another species, or another antibody class or subclass. Furthermore, mutant antibodies and antibody fragments thereof are also comprised in the present invention (U.S. Pat. No. 4,816,567; Morrison et al., Proc. Natl. Acad. Sci. USA (1984) 81, 6851-5).

Herein, "mutant antibody" refers to an antibody comprising a variant amino acid sequence in which one or more amino acid residues have been altered. For example, the variable region of an antibody can be modified to improve its biological properties, such as antigen binding. Such modifications can be achieved by site-directed mutagenesis (see Kunkel, Proc. Natl. Acad. Sci. USA (1985) 82, 488), PCR-based mutagenesis, cassette mutagenesis, and the like. Such mutants comprise an amino acid sequence which is at least 70% identical to the amino acid sequence of a heavy or light chain variable region of the antibody, more preferably at least 75%, even more preferably at least 80%, still more preferably at least 85%, yet more preferably at least 90%, and most preferably at least 95% identical. Herein, sequence identity is defined as the percentage of residues identical to those in the antibody's original amino acid sequence, determined after the sequences are aligned and gaps are appropriately introduced to maximize the sequence identity as necessary.

Specifically, the identity of one nucleotide sequence or amino acid sequence to another can be determined using the algorithm BLAST, by Karlin and Altschul (Proc. Natl. Acad. Sci. USA (1993) 90, 5873-7). Programs such as BLASTN and BLASTX were developed based on this algorithm (Altschul et al., J. Mol. Biol. (1990) 215, 403-10). To analyze nucleotide sequences according to BLASTN based on BLAST, the parameters are set, for example, as score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (see the website of the National Center for Biotechnology Information (NCBI), Basic Local Alignment Search Tool (BLAST); www.ncbi.nlm.nih.gov).

The polyclonal and monoclonal antibodies used in the present invention can be prepared by methods known to those skilled in the art. For example, the antibodies can be prepared by the methods described below.

For animal immunization, PCIs including the entire PCI amino acid sequence and partial peptides thereof prepared by recombinant DNA techniques or chemical synthesis can be used. The amino acid sequences of human PCI and PCIs from other mammals are known (Suzuki, K. et al., J. Biol. Chem. (1987) 262, 611-6), and can be used to prepare antibodies for use in the present invention. In the present invention, mammalian PCIs include, but are not limited to, for example, mouse, rat, and bovine PCIs (Zechmeister-Machhart, M., et al., Gene (1997) 186 (1), 61-6; Wakita, T., et al., FEBS Lett. (1998) 429 (3), 263-8; Yuasa, J., et al., Thromb. Haemost. (2000) 83 (2), 262-7). Recombinant PCI proteins can be prepared, for example, by the methods described in Example 1. As an antigen, PCI itself or its partial peptides can be used without modification, or after being conjugated with a carrier protein. When a carrier protein is used, for example, the antigen PCI is first coupled with the carrier protein (for example, cycloglobulin), and then an adjuvant is added thereto. Such adjuvants include Freund's complete and incomplete adjuvants and the like, any of which can be combined with the antigen.

An antigen prepared as described above is administered into a mammal, such as a mouse, rat, hamster, guinea pig, horse, monkey, rabbit, goat, or sheep. This immunization can be performed by any existing method, for example, by intravenous injections, subcutaneous injections, and intraperitoneal injections. There are no restrictions as to the immunization intervals. Immunization may be carried out at intervals of several days to several weeks, preferably four to 21 days. A mouse can be immunized, for example, at a single dose of 10 to 100 µg (for example, 20 to 60 µg) of the antigen protein.

Before the first immunization, as well as three to seven days after the second and subsequent immunizations, blood is collected from the animal, and the serum is analyzed for antibody titer. To promote an immune response, an aggregating agent such as alum is preferably used. In general, selected mammalian antibodies have sufficiently high antigen binding affinity. Antibody affinity can be determined using a saturation binding assay, an enzyme-linked immunosorbent assay (ELISA), or a competitive assay (for example, a radioimmunoassay).

Polyclonal antibodies can be screened by a conventional crosslinking analysis, such as that described in "Antibodies, A Laboratory Manual (Cold Spring Harbor Laboratories, Harlow and David Lane edit. (1988))". An alternative method is, for example, epitope mapping (Champe et al., J. Biol. Chem. (1995) 270, 1388-94). A preferred method for determining polypeptide or antibody titers comprises quantifying antibody-binding affinity. In other embodiments, methods for assessing one or more biological properties of an antibody are also used in addition to or in place of the methods for determining antibody-binding affinity. Such analytical methods are particularly useful because they demonstrate the therapeutic effectiveness of antibodies. When an antibody exhibits an improved property in such analyses, its binding affinity is also generally, but not always, enhanced.

Hybridomas that are used to prepare monoclonal antibodies can be obtained, for example, by the method of Milstein et al. (Kohler, G. and Milstein, C., Methods Enzymol. (1981) 73, 3-46). Myeloma cells to be fused with antibody-producing cells may be cell lines derived from any of the various animals generally available to those skilled in the art, such as mice, rats, and humans. The cell lines to be used are drug-resistant, and cannot survive in a selective medium (e.g., HAT medium) in an unfused state, but can survive in a fused state. 8-azaguanine-resistant cell lines are generally used, which are deficient in hypoxanthine-guanine-phosphoribosyl transferase and cannot grow in a hypoxanthine-aminopterin-thymidine (HAT) medium. Preferred myeloma cells include a variety of known cell lines, for example, P3x63Ag8.653 (J. Immunol. (1979) 123, 1548-50), P3x63Ag8U.1 (Current Topics in Microbiology and Immunology (1978) 81, 1-7), NS-1 (Kohler, G. and Milstein, C., Eur. J. Immunol. (1976) 6, 511-9), MPC-11 (Margulies, D. H. et al., Cell (1976) 8, 405-5), SP2/0 (Shulman, M. et al., Nature (1978) 276, 269-70), F0 (de St. Groth, S. F. et al., J. Immunol. Methods (1980) 35, 1-21), S194 (Trowbridge, I. S., J. Exp. Med. (1978) 148, 313-23), 8210 (Galfre, G. et al., Nature (1979) 277, 131-3), and P3U1 (J. Exp. Med. (1979) 150, 580; Curr. Top. Microbiol. Immunol. (1978) 81, 1). Human myeloma and mouse-human heteromyclom cell lines can also be used to produce human monoclonal antibodies (Kozbar, J. Immunol. (1984) 133, 3001; Brodeur et al., Monoclonal Antibody Production Techniques and Application, Marcel Dekker, Inc., New York, (1987) pp. 51-63). Antibody-producing cells are collected, for example, from animals sacrificed two to three days after the final immunization. Antibody-producing cells include spleen cells, lymph node cells, and peripheral blood cells. Particularly, spleen cells are generally used. Specifically, spleens, lymph nodes or the like are excised or collected from the various animals described above, and are then crushed. The resulting material is suspended in a medium or buffer, such as PBS, DMEM, and RPMI1640, followed by filtration with a stainless mesh or the like. This is then centrifuged to obtain antibody-producing cells of interest.

The above-described myeloma cells and antibody-producing cells are then fused. Cell fusion is achieved by contacting the myeloma cells with the antibody-producing cells at a ratio of 1:1 to 1:20 in a medium for animal cell culture, such as MEM, DMEM, and RPMI-1640, at 30° C. to 37° C. for one to 15 minutes in the presence of a fusion-promoting agent. To promote cell fusion, a fusion-promoting agent such as polyethylene glycol (mean molecular weight 1,000 to 6,000 Da) or polyvinyl alcohol, or a Sendai virus may be used, or the antibody-producing cells and the myeloma cells may be fused by a commercially available cell-fusion device using viruses for fusion.

Hybridomas of interest are selected from the cells after cell fusion. The selection methods include methods using selective propagation of cells in a selective medium. Specifically, a cell suspension is diluted with an appropriate medium, and then the cells are plated on to microtiter plates. An aliquot of selection medium (for example, HAT medium) is added to each well, and then the cells are cultured while the selection medium is appropriately exchanged. The cells grown as a result can be saved as hybridomas.

In another embodiment, antibodies or antibody fragments can be isolated from an antibody phage library, produced by using the technique reported by McCafferty et al. (Nature (1990) 348, 552-4). Clackson et al. (Nature (1991) 352, 624-8) and Marks et al. (J. Mol. Biol. (1991) 222, 581-97) reported on the respective isolation of mouse and human antibodies from phage libraries. They can be referred when preparing the antibodies used in the present invention. There are also reports that describe the production of high affinity (nM range) human antibodies based on chain shuffling (Marks et al., Bio/Technology (1992) 10, 779-83), and combinatorial infection and in vivo recombination, which are methods for constructing large-scale phage libraries (Waterhouse et al., Nucleic Acids Res. (1993) 21, 2265-6). These technologies can also be used to isolate monoclonal antibodies, in place of the conventional hybridoma technology for monoclonal antibody production.

Preferably, the anti-PCI neutralizing antibodies of the present invention can be selected by the screening method described below:

Primary Screening

To select antibodies that bind to PCI, each antibody is assessed for its binding specificity using a known technique, such as EIA (enzyme immunoassay), RIA (radioimmunoassay), ELISA (enzyme-linked immunosorbent assay), HTRF (homogenous time-resolved fluorescence), or fluorescence immunoassay (Antibodies A Laboratory Manual, Ed Harlow, David Lane, Cold Spring Harbor Laboratory (1988)).

Secondary Screening

Secondary screening selects antibodies with a relatively strong degree of inhibition against PCI. PCI inhibits HGFa activity as well as the formation of active two-chain HGF by forming a complex with HGFa. Thus, the effect of an antibody in inhibiting PCI is determined by incubating PCI with an anti-PCI antibody, adding this mixture to a solution comprising HGFa, or the like, incubating, and then measuring HGFa activity. The proportion of the inhibitory effect of PCI on HGFa activity that is inhibited by an anti-PCI antibody can be determined based on the HGFa activity level when PCI is absent (HGFa activity without PCI inhibition) and when the anti-PCI antibody is absent (HGFa activity when inhibited by PCI). PCI is mixed with HGFa using appropriate solutions. Such solutions can include physiological phosphate buffer, but are not limited thereto. In such assays, typically, 0.001 to 1,000 μg/ml of PCI is combined with 0.001 to 1,000 μg/ml of HGFa in a molar ratio of 1:1 to 1:1,000. The reaction can be conducted, for example, at 20° C. to 40° C. for five minutes to six hours. When the incubation of PCI with an antibody reduces the degree of PCI inhibition of HGFa activity compared to in the absence of the antibody, the antibody is judged to have inhibitory activity against the effect of PCI in inhibiting HGFa activity. HGFa activity can be determined by the method described in Example 1 of JP-A 2002-273 (Patent Document 2); briefly, the quantity of AMC (7-amino-4-methylcoumarin) produced in a degradation reaction using a synthetic substrate (Ac-AKTKQLR (SEQ ID NO: 1 in the same document)-MCA) is determined using an excitation wavelength of 380 nm and a fluorescence emission wavelength of 460 nm. The degree to which PCI activity is inhibited by antibodies is measured to select antibodies that exhibit a relatively high degree of inhibition. For example, when the assay comprises the use of antibodies prepared from antibody-producing cells (for example, hybridomas), the antibody-producing cells that produce antibodies comprising the activity of interest are identified and subcloned by the limiting dilution method. The clones are grown using standard methods (Goding, Monoclonal Antibodies, Principals and Practice, Academic Press (1986) pp. 59-103). The cells may be cultured in a medium, for example, D-MEM or RPIM-1640 medium. Such hybridomas can be cloned by repeating the screening, which comprises selecting hybridomas that produce stronger anti-PCI neutralizing antibodies.

In the above assay using hybridoma culture supernatants, the value is set at 100 in the absence of PCI, and at 0 when a hybridoma culture medium (for example, HAT medium) is used in place of the hybridoma culture supernatant. Antibody-producing hybridomas which have a relative PCI-inhibiting activity of preferably 45 or higher, more preferably 48 or higher, even more preferably 50 or higher, still more preferably 60 or higher, still more preferably 70 or higher, still more preferably 80 or higher, and yet still more preferably 90 or higher, are selected. The present invention provides hybridomas with a relative PCI-inhibiting activity of preferably 45 or higher, more preferably 48 or higher, even more preferably 50 or higher, still more preferably 60 or higher, still more preferably 70 or higher, still more preferably 80 or higher, and yet still more preferably 90 or higher, in the assay using culture supernatants.

Antibodies can be purified from hybridoma culture supernatants according to conventional methods. In assays where the value in the absence of antibody is set at 100% and the value in the absence of PCI is set at 0%, in order to achieve 50% inhibition, the antibodies of the present invention have a concentration of preferably 100 μg/ml or lower, more preferably 80 μg/ml or lower, even more preferably 60 μg/ml or lower, still more preferably 50 μg/ml or lower, still more preferably 40 μg/ml or lower, still more preferably 25 μg/ml or lower, still more preferably 15 μg/ml or lower, and yet still more preferably 12.5 μg/ml or lower. Alternatively, at an antibody concentration of 25 μg/ml, the antibodies of the present invention have a relative PCI inhibition value of preferably 40% or higher, more preferably 50% or higher, even more preferably 60% or higher, still more preferably 70% or higher, and yet still more preferably 80% or higher in the same assay. The 50% inhibition concentration can be determined by carrying out the assay at various antibody concentrations, plotting a graph, and determining the antibody concentration that corresponds to 50% inhibition from the graph.

In general, antibodies exhibiting stronger PCI binding are considered as more preferable antibodies of the present invention. The dissociation constant (KD) for the interaction between PCI and an antibody of the present invention is preferably 50 nM or less, more preferably 20 nM or less, even more preferably 10 nM or less, still more preferably 5 nM or less, still more preferably 3 nM or less, still more preferably 1 nM or less, still more preferably 0.8 nM or less, still more preferably 0.6 nM or less, still more preferably 0.4 nM or less, and yet still more preferably 0.2 nM or less. Kinetic parameters for the binding, such as dissociation constant, binding rate constant (ka), dissociation rate constant (kd), and maximal binding (Rmax), can be determined, for example, using surface plasmon resonance analysis, such as BIACORE.

Furthermore, the antibodies of the present invention preferably have the activity of suppressing the blood-mediated inactivation of HGFa. The antibodies of the present invention preferably suppress 10% or more, more preferably 15% or more, even more preferably 20% or more, still more preferably 25% or more, and yet still more preferably 30% or more of the HGFa inactivation by blood. Such suppression levels are defined as the suppression rate of inactivation (%), and are expressed as relative values between 0% (HGFa activity when inactivated by blood) and 100% (HGFa activity without inactivation).

Methods for preparing monoclonal antibodies from the obtained hybridomas include standard cell culture methods and methods comprising ascites production. In cell culture methods, hybridomas are cultured for two to 14 days under standard culture conditions (for example, at 37° C., 5% $CO_2$ atmosphere), in a culture medium for animal cells, such as RPMI-1640 or MEM containing 10% to 20% fetal calf serum, or serum-free medium, and antibodies are then prepared from the culture supernatant. In methods comprising ascites production, hybridomas are administered to the peritoneal cavities of mammalian individuals of the same species as that from which the myeloma cells were derived, and the hybridomas proliferate into large quantities. Ascites or sera are then collected after one to four weeks. To enhance ascites production, for example, pristane (2,6,10,14-tetramethylpentadecane) may be pre-administered into the peritoneal cavity.

Antibodies to be used in the present invention can be purified by methods appropriately selected from known methods, such as the protein A-Sepharose method, protein G-Sepharose method, hydroxyapatite chromatography, salting-out method with sulfate, ion exchange chromatography, and affinity chromatography, or by the combined use of the same.

The present invention may use recombinant antibodies, produced by gene engineering. The genes encoding the antibodies obtained by a method described above are cloned from the hybridomas. The genes are inserted into an appropriate vector, and then introduced into a host (see, for example, Carl, A. K. Borrebaeck, James, W. Larrick, Therapeutic Monoclonal Antibodies, published in the United Kingdom by Macmillan Publishers Ltd (1990)). Specifically, using a reverse transcriptase, cDNAs encoding the variable regions (V regions) of the antibodies are synthesized from the mRNAs of hybridomas. The DNAs encoding the variable regions of the antibodies of interest are obtained, and then ligated with DNAs encoding desired constant regions (C regions) of the antibodies, and the resulting DNA constructs are inserted into expression vectors. Alternatively, the DNAs encoding the variable regions of the antibodies may be inserted into expression vectors comprising the DNAs of the antibody C regions. These are inserted into expression vectors so that the genes are expressed under the regulation of an expression regulatory region, for example, an enhancer and/or a promoter. Then, host cells are transformed with the expression vectors to express the antibodies.

Particularly preferred antibodies for use in the present invention are antibodies with antibody-binding sites that fully or partially overlap with an antibody comprising the variable region of any one of the monoclonal antibodies (PC19G8, PC23A7, PC23D8, PC30G1, PC31E2, PC31F1, and PC39C6) isolated in the Examples. Herein, such antibodies are referred to as antibodies that bind to practically the same site on PCI as one of the monoclonal antibodies (PC19G8, PC23A7, PC23D8, PC30G1, PC31E2, PC31F1, or PC39C6). Whether two antibodies bind to an identical site on an antigen protein can be determined by, for example, competition experiments. Specifically, when the binding between PCI and a first anti-PCI antibody is competitively inhibited by a second anti-PCI antibody, the first and second antibodies are judged to bind to an identical site on the antigen. For example, antibodies which compete for an antigen binding site with any of the PC19G8, PC23A7, PC23D8, PC30G1, PC31E2, PC31F1, and PC39C6 antibodies, or antibodies comprising an H chain variable region comprising the amino acid sequence of SEQ ID NO: 8, 9, 10, 11, 12, 13, or 14 and a corresponding L chain variable region comprising the amino acid sequence of SEQ ID NO: 15, 16, 17, 18, 19, 20, or 21, are preferable as the antibodies of the present invention. Alternatively, antibodies that bind to practically the same site on PCI as one of the monoclonal antibodies described above can also be obtained by using partial PCI peptides to analyze the monoclonal antibody epitopes by known epitope mapping techniques, and using peptides containing the identified epitopes as antigens to prepare binding antibodies. Such antibodies are expected to produce the same inhibitory effect against HGFa activity as the antibodies isolated in the Examples. Thus, antibodies which bind to practically the same PCI site as the antibodies isolated in the Examples, wherein the isolated antibodies have the activity of inhibiting the PCI inhibitory effect on HGFa activity, can preferably be used in the present invention.

The antibodies of the present invention also include antibodies that comprise the complementarity determining regions (CDRs) of any of the monoclonal antibodies isolated in the Examples (PC19G8, PC23A7, PC23D8, PC30G1, PC31E2, PC31F1, or PC39C6), or complementarity determining regions functionally equivalent thereto. The term "functionally equivalent" refers to comprising amino acid sequences similar to the amino acid sequences of the CDRs of any of the monoclonal antibodies isolated in the Examples, and with the activity of inhibiting PCI function by binding thereto. The term "CDR" refers to a region in an antibody variable region (also called "V region"), and determines the specificity of antigen binding. The H chain and L chain each have three CDRs, designated from the N terminus as CDR1, CDR2, and CDR3. There are four regions flanking these CDRs: these regions are referred to as the "framework", and their amino acid sequences are highly conserved. The CDRs can be grafted into other antibodies, and thus a recombinant antibody can be prepared by combining CDRs with the framework of a desired antibody. One or more amino acids of a CDR can be modified without losing the ability to bind to its antigen. For example, one or more amino acids in a CDR can be substituted, deleted, and/or added.

An amino acid residue is preferably altered into one that allows the properties of the amino acid side-chain to be conserved. Examples of the properties of amino acid side-chains include: hydrophobic amino acids (A, I, L, M, F, P, W, Y, V), hydrophilic amino acids (R, D, N, C, E, Q, G, H, K, S, T), and amino acids comprising the following side chains: aliphatic side-chains (G, A, V, L, I, P); hydroxyl group-containing side-chains (S, T, Y); sulfur atom-containing side-chains (C, M); carboxylic acid- and amide-containing side-chains (D, N, E, Q); base-containing side-chains (R, K, H); and aromatic-containing side-chains (H, F, Y, W). (The letters within parenthesis indicate the one-letter amino acid codes.) Amino acid substitutions within each group are called conservative substitutions. It is well known that a polypeptide comprising a modified amino acid sequence in which one or more amino acid residues is deleted, added, and/or substituted can retain its original biological activity (Mark, D. F. et al., Proc. Natl. Acad. Sci. USA (1984) 81, 5662-6; Zoller, M. J. and Smith, M., Nucleic Acids Res. (1982) 10, 6487-500; Wang, A. et al., Science (1984) 224, 1431-3; Dalbadie-McFarland, G. et al., Proc. Natl. Acad. Sci. USA (1982) 79, 6409-13). The number of mutated amino acids is not limited, but in general, it is within 40% of the amino acids of each CDR, and preferably within 35%, and still more preferably within 30% (e.g., within 25%). The identity of amino acid sequences can be determined by a method described above.

The antibodies of the present invention include, for example, antibodies that comprise three CDRs comprising amino acid sequences: D(T/Y)(F/Y)(M/I)H (SEQ ID NO: 49), RID(Y/L)(V/E)(N/K)(G/V)N(T/I)(K/I)YDP(K/N)FQ (G/D) (SEQ ID NO: 50), and GGYDV(R/P)(E/S)FAY (SEQ ID NO: 51) (wherein the slash dividing the amino acids implies that either of the amino acids may be present), or their functionally equivalent CDRs. The amino acid sequences indicated above correspond to antibody H chain CDR1, CDR2, and CDR3, respectively. The PCI-neutralizing antibodies of the present invention can be prepared by inserting the CDRs into positions corresponding to CDR1, CDR2, and CDR3 in the framework of a desired H chain variable region. More specific examples of the preferred amino acid sequences of antibody H chain CDRs are DTFMH (SEQ ID NO: 22) and DYYIH (SEQ ID NO: 23) for CDR1, RIDYVNGNTKYDPKFQG (SEQ ID NO: 26), RIDLVNVNTKYDPNFQD (SEQ ID NO: 27), and RIDLEKGNIIY-DPKFQG (SEQ ID NO: 28) for CDR2, GGYDVREFAY (SEQ ID NO: 32) and GGYDVPSFAY (SEQ ID NO: 33) for CDR3. In addition, the amino acids of each of the above-described CDRs may be appropriately modified by substitution and the like, as long as an obtained antibody has PCI-neutralizing activity. For example, an antibody in which the CDR amino acids are conservatively substituted is expected to retain the neutralizing activity of its original antibody, and thus can be used as an antibody of the present invention. More specifically, the CDRs may comprise combinations of CDR1, 2, and 3 from the H chains of monoclonal antibodies PC23D8, PC19G8, PC23A7, and PC39C6 (see FIG. 5). Such an antibody is expected to have PCI-neutralizing activity equivalent to that of the clones described above.

The L chain variable region of an antibody may be appropriately combined with an antibody comprising an H chain CDR described above. The preferred L chain CDRs include combinations of CDRs comprising the amino acid sequences of SA(T/S)SS(L/V)(I/S)YMH (SEQ ID NO: 55), STSNLAS-GVPA (SEQ ID NO: 56), and RSSYPFT (SEQ ID NO: 57), and functionally equivalent CDRs thereof. The amino acid sequences correspond, respectively, to CDR1, CDR2, and CDR3 of an antibody L chain. The L chain CDRs may also be used independently of the above H chains. These CDRs are inserted into positions corresponding to CDR1, CDR2, and CDR3 in the framework of a desired L chain variable region. More specific examples of the preferred amino acid sequences of antibody L chain CDRs include, but are not limited to, SATSSLIYMH (SEQ ID NO: 37) and SASSS-VSYMH (SEQ ID NO: 38) for CDR1, STSNLASGVPA (SEQ ID NO: 42) for CDR2, and RSSYPFT (SEQ ID NO: 46) for CDR3 in the present invention.

Specifically, the antibodies of the present invention include those comprising the following H chain complementarity determining regions, and which have the activity to inhibit PCI inhibitory effect on HGFa activity.

(a) A complementarity determining region comprising the amino acid sequences of SEQ ID NOs: 49, 50, and 51.

(b) A complementarity determining region comprising amino acid sequences of SEQ ID NOs: 49, 50, and 51 with conservative substitutions of arbitrary amino acids.

(c) A complementarity determining region comprising amino acid sequences with substitutions, deletions, and/or additions of three amino acids or less in SEQ ID NO: 49, eight amino acids or less in SEQ ID NO: 50, and five amino acids or less in SEQ ID NO: 51.

(d) A complementarity determining region comprising amino acid sequences having 70% or more identity to each of SEQ ID NOs: 49, 50, and 51.

The number of modified amino acids in the sequence of SEQ ID NO: 49 in (c) is preferably two or less, and more preferably one. The number of modified amino acids in the sequence of SEQ ID NO: 50 in (c) is preferably seven or less, more preferably six or less, even more preferably five or less, still more preferably four or less, and yet still more preferably three or less. The number of modified amino acids in the sequence of SEQ ID NO: 51 in (c) is preferably four or less, more preferably three or less, even more preferably two or less, and still more preferably one. The identity in (d) is preferably 75% or more, more preferably 80% or more, even more preferably 90% or more, and still more preferably 95% or more.

Furthermore, the antibodies of the present invention also include those comprising the following L chain complementarity determining regions, and which have the activity to inhibit PCI inhibitory effect on HGFa activity.
(a) A complementarity determining region comprising the amino acid sequences of SEQ ID NOs: 55, 56, and 57.
(b) A complementarity determining region comprising the amino acid sequence of SEQ ID NOs: 55, 56, and 57 with conservative substitutions of arbitrary amino acids.
(c) A complementarity determining region comprising amino acid sequences with substitutions, deletions, and/or additions of five amino acids or less in SEQ ID NO: 55, five amino acids or less in SEQ ID NO: 56, and four amino acids or less in SEQ ID NO: 57.
(d) A complementarity determining region comprising amino acid sequences having 70% or more identity to each of SEQ ID NOs: 55, 56, and 57.

The number of modified amino acids in the sequence of SEQ ID NO: 55 in (c) is preferably four or less, more preferably three or less, even more preferably two or less, and still more preferably one. The number of modified amino acids in the sequence of SEQ ID NO: 56 in (c) is preferably four or less, more preferably three or less, even more preferably two or less, and still more preferably one. The number of modified amino acids in the sequence of SEQ ID NO: 57 in (c) is preferably three or less, more preferably two or less, and still more preferably one. The amino acid identity in (d) is preferably 75% or more, more preferably 80% or more, even more preferably 90% or more, and still more preferably 95% or more. The preferred antibodies of the present invention include, in particular, antibodies comprising both the H chain and the L chain complementarity determining regions described above.

The antibodies used in the present invention also include antibodies that comprise CDRs comprising the amino acid sequences of RYWMS (SEQ ID NO: 52), EINPDSSTI(N/T)YT(P/S)SLKD (SEQ ID NO: 53), and (F/L)FYYGTPDY (SEQ ID NO: 54), or their functionally equivalent CDRs. As described above, the amino acid sequences indicated above correspond to the CDR1, CDR2, and CDR3 of an antibody H chain, respectively. More specific examples of the preferred amino acid sequences of antibody H chain CDRs are RYWMS (SEQ ID NO: 24) for CDR1, EINPDSSTINYTPSLKD (SEQ ID NO: 29) and EINPDSSTITYTSSLKD (SEQ ID NO: 30) for CDR2, and FFYYGTPDY (SEQ ID NO: 34) and LFYYGTPDY (SEQ ID NO: 35) for CDR3. Specifically, combinations of CDR1, 2, and 3 from the H chain of monoclonal antibodies PC30G1 and PC31F1 can be used. Such antibodies are expected to have PCI-neutralizing activity equivalent to that of PC30G1 or PC31F1. In this case, it is preferable to combine them with L chain CDRs, such as CDRs comprising the amino acid sequences of KASQDVI(V/K)AVA (SEQ ID NO: 58), S(A/T)SYRYTGVPD (SEQ ID NO: 59), and HYSSPPWT (SEQ ID NO: 60), or functionally equivalent CDRs thereof. These amino acid sequences correspond to CDR1, CDR2, and CDR3 of an antibody L chain, respectively. The L chain CDRs may also be used independently of the H chain described above. Specific examples of the preferred amino acid sequences of L chain CDR include, but are not limited to, KASQDVIVAVA (SEQ ID NO: 39) and KASQDVIKAVA (SEQ ID NO: 40) for CDR1, SASYRYTGVPD (SEQ ID NO: 43) and STSYRYTGVPD (SEQ ID NO: 44) for CDR2, and HYSSPPWT (SEQ ID NO: 47) for CDR3 in the present invention.

Specifically, the antibodies of the present invention include those comprising the following H chain complementarity determining regions, and which have the activity to inhibit PCI inhibitory effect on HGFa activity:
(a) A complementarity determining region comprising the amino acid sequences of SEQ ID NOs: 52, 53, and 54.
(b) A complementarity determining region comprising the amino acid sequences of SEQ ID NOs: 52, 53, and 54 with conservative substitutions of arbitrary amino acids.
(c) A complementarity determining region comprising amino acid sequences with substitutions, deletions, and/or addition of three amino acids or less in SEQ ID NO: 52, eight amino acids or less in SEQ ID NO: 53, and five or less amino acids of SEQ ID NO: 54.
(d) A complementarity determining region comprising amino acid sequences having 70% or more identity to each of SEQ ID NOs: 52, 53, and 54.

The number of modified amino acids in the sequence of SEQ ID NO: 52 in (c) is preferably two or less, and more preferably one. The number of modified amino acids in the sequence of SEQ ID NO: 53 in (c) is preferably seven or less, more preferably six or less, even more preferably five or less, still more preferably four or less, and yet still more preferably three or less. The number of modified amino acids in the sequence of SEQ ID NO: 54 in (c) is preferably four or less, more preferably three or less, even more preferably two or less, and still more preferably one. The amino acid identity in (d) is preferably 75% or more, more preferably 80% or more, even more preferably 90% or more, and still more preferably 95% or more.

The antibodies of the present invention also include those comprising the following L chain complementarity determining regions, and which have the activity to inhibit PCI inhibitory effect on HGFa activity:
(a) A complementarity determining region comprising the amino acid sequences of SEQ ID NOs: 58, 59, and 60.
(b) A complementarity determining region comprising the amino acid sequences of SEQ ID NOs: 58, 59, and 60 with conservative substitutions of arbitrary amino acids.
(c) A complementarity determining region comprising amino acid sequences with substitutions, deletions, and/or additions of five amino acids or less in SEQ ID NO: 58, five amino acids or less in SEQ ID NO: 59, and four or less amino acids in SEQ ID NO: 60.
(d) A complementarity determining region comprising amino acid sequences having 70% or more identity to each of SEQ ID NOs: 58, 59, and 60.

The number of modified amino acids in the sequence of SEQ ID NO: 58 in (c) is preferably four or less, more preferably three or less, even more preferably two or less, and still more preferably one. The number of modified amino acids in the sequence of SEQ ID NO: 59 in (c) is preferably four or less, more preferably three or less, even more preferably two or less, and still more preferably one. The number of modified amino acids in the sequence of SEQ ID NO: 60 in (c) is preferably three or less, more preferably two or less, and still more preferably one. The amino acid identity in (d) is preferably 75% or more, more preferably 80% or more, even more preferably 90% or more, and still more preferably 95% or more. Antibodies comprising both the H chain and the L chain complementarity determining regions described above are particularly preferred as the antibodies of the present invention.

The antibodies of the present invention also include antibodies that comprise CDRs comprising the amino acid sequences of TYPIE (SEQ ID NO: 25), KFHPDNDDT-NYNEKFKG (SEQ ID NO: 31), and GHDYDYGMDY (SEQ ID NO: 36), or functionally equivalent CDRs thereof. As described above, these amino acid sequences correspond to the CDR1, CDR2, and CDR3 of an antibody H chain, respectively. Such antibodies are expected to have PCI-neutralizing activity equivalent to that of PC31E2. In this case, it is preferable to combine them with L chain CDRs, for example, CDRs comprising the amino acid sequences of KASQSVDYDGDSYLN (SEQ ID NO: 41), GASNLES-GTPA (SEQ ID NO: 45), and SNEDPPT (SEQ ID NO: 48), or functionally equivalent CDRs thereof. These amino acid sequences correspond to CDR1, CDR2, and CDR3 of an antibody L chain, respectively.

Specifically, the antibodies of the present invention include those comprising the following H chain complementarity determining regions, and which have the activity to inhibit PCI inhibitory effect on HGFa activity.
(a) A complementarity determining region comprising the amino acid sequences of SEQ ID NOs: 25, 31, and 36.
(b) A complementarity determining region comprising the amino acid sequences of SEQ ID NOs: 25, 31, and 36 with conservative substitutions of arbitrary amino acids.
(c) A complementarity determining region comprising amino acid sequences with substitutions, deletions, and/or additions of three amino acids or less in SEQ ID NO: 25, eight amino acids or less in SEQ ID NO: 31, and five or less amino acids in SEQ ID NO: 36.
(d) A complementarity determining region comprising amino acid sequences having 70% or more identity to each of SEQ ID NOs: 25, 31, and 36.

The number of modified amino acids in the sequence of SEQ ID NO: 25 in (c) is preferably two or less, and more preferably one. The number of modified amino acids in the sequence of SEQ ID NO: 31 in (c) is preferably seven or less, more preferably six or less, even more preferably five or less, still more preferably four or less, and yet still more preferably three or less. The number of modified amino acids in the sequence of SEQ ID NO: 36 in (c) is preferably four or less, more preferably three or less, even more preferably two or less, and still more preferably one. The amino acid identity in (d) is preferably 75% or more, more preferably 80% or more, even more preferably 90% or more, and still more preferably 95% or more.

The antibodies of the present invention also include those comprising the following L chain complementarity determining regions, and which have the activity to inhibit PCI inhibitory effect on HGFa activity.
(a) A complementarity determining region comprising the amino acid sequences SEQ ID NOs: 41, 45, and 48.
(b) A complementarity determining region comprising the amino acid sequences of SEQ ID NOs: 41, 45, and 48 with conservative substitutions of arbitrary amino acids.
(c) A complementarity determining region comprising amino acid sequences with substitutions, deletions, and/or additions of five amino acids or less in SEQ ID NO: 41, five amino acids or less in SEQ ID NO: 45, and four amino acids or less in SEQ ID NO: 48.
(d) A complementarity determining region comprising amino acid sequences having 70% or more identity to each of SEQ ID NOs: 41, 45, and 48.

The number of modified amino acids in the sequence of SEQ ID NO: 41 in (c) is preferably four or less, more preferably three or less, even more preferably two or less, and still more preferably one. The number of modified amino acids in the sequence of SEQ ID NO: 45 in (c) is preferably four or less, more preferably three or less, even more preferably two or less, and still more preferably one. The number of modified amino acids in the sequence of SEQ ID NO: 48 in (c) is preferably three or less, more preferably two or less, and still more preferably one. The degree of identity in (d) is preferably 75% or more, more preferably 80% or more, even more preferably 90% or more, still more preferably 95% or more. Antibodies comprising both the H chain and the L chain complementarity determining regions described above are particularly preferred as the antibodies of the present invention.

The CDR amino acid sequences can be modified, for example, by synthesizing oligonucleotides encoding the amino acid sequence of a modified variable region comprising CDR, and preparing nucleic acids encoding the variable region by PCR using the oligonucleotides. Antibodies that comprise desired CDRs can be prepared by inserting the nucleic acid into an appropriate expression vector and expressing it. For example, the oligonucleotides are synthesized using mixed nucleotides to prepare a DNA library that encodes a variety of antibodies comprising CDRs with various amino acids introduced at certain positions. The antibodies for use in the present invention can be isolated by selecting from the library clones encoding antibodies that binds to PCI and suppresses its activity.

In the present invention, recombinant antibodies artificially modified to reduce heterologous antigenicity against humans can be used. Examples include chimeric antibodies and humanized antibodies. These modified antibodies can be produced using known methods. Chimeric antibodies include antibodies comprising variable and constant regions of species that are different to each other; for example, an antibody comprising the antibody heavy chain and light chain variable regions of a nonhuman mammal such as a mouse, and the antibody heavy chain and light chain constant regions of a human. Such an antibody can be obtained by (1) ligating a DNA encoding a variable region of a mouse antibody to a DNA encoding a constant region of a human antibody; (2) incorporating this into an expression vector; and (3) introducing the vector into a host for production of the antibody.

A humanized antibody, which is also called a reshaped human antibody, is obtained by substituting a heavy or light chain complementarity determining region (CDR) of an antibody of a nonhuman mammal such as a mouse, with the CDR of a human antibody. Conventional genetic recombination techniques for the preparation of such antibodies are known (see, for example, Jones et al., Nature (1986) 321, 522-5; Reichmann et al., Nature (1988) 332, 323-9; Presta. Curr. Op. Struct. Biol. (1992) 2, 593-6). Specifically, a DNA sequence designed to ligate a CDR of a mouse antibody with the framework regions (FRs) of a human antibody is synthesized by PCR, using several oligonucleotides constructed to comprise overlapping portions at their ends. A humanized antibody can be obtained by (1) ligating the resulting DNA to a DNA that encodes a human antibody constant region; (2) incorporating this into an expression vector; and (3) transfecting the vector into a host to produce the antibody (see European Patent Application No. EP 239,400 and International Patent Application Publication No. WO 96/02576). Human antibody FRs that are ligated via the CDR are selected where the CDR forms a favorable antigen-binding site. The humanized antibody may comprise additional amino acid residue(s) that are not included in the CDRs introduced into the recipient antibody, nor in the framework sequences. Such amino acid residues are usually introduced to more accurately optimize the antibody's ability to recognize and bind to an antigen. For example, as necessary, amino acids in the framework region of an antibody variable region may be substituted such that the CDR of a reshaped human antibody forms an appropriate antigen-binding site (Sato, K. et al., Cancer Res. (1993) 53, 851-6).

Methods for obtaining human antibodies are also known. For example, desired human antibodies with antigen-binding activity can be obtained by (1) sensitizing human lymphocytes with antigens of interest or cells expressing antigens of interest in vitro; and (2) fusing the sensitized lymphocytes with human myeloma cells such as U266 (see Japanese Patent Application Kokoku Publication No. (JP-B) H01-59878 (examined, approved Japanese patent application published for opposition)). Alternatively, the desired human antibody can also be obtained by using an antigen to immunize a transgenic (Tg) animal that comprises a partial or entire repertoire of human antibody genes (see Nature Genetics (1994) 7, 13-21; Nature Genetics (1997) 15, 146-56; Nature (1994) 368, 856-9; International Patent Application Publication Nos. WO 93/12227, WO 92/03918, WO 94/02602, WO 94/25585, WO 96/34096, and WO 96/33735). Specifically, such Tg animals are created as follows: a nonhuman mammal in which the loci of heavy and light chains of an endogenous immunoglobulin have been disrupted, and instead, the loci of heavy and light chains of a human immunoglobulin have been introduced via yeast artificial chromosome (YAC) vectors and the like, is obtained by creating knockout animals or Tg animals, or mating such animals. The immunoglobulin heavy chain loci can be functionally inactivated, for example, by introducing a defect at a certain site in a J region or C region (e.g., Cµ region). The immunoglobulin light chains (e.g., κ chain) can be functionally inactivated, for example, by introducing a defect at a certain site in a J region or C region, or a region comprising the J and C regions.

Such humanized antibodies can also be obtained from culture supernatants, by using genetic engineering technology to transform eukaryotic cells with cDNAs that encode each of the heavy and light chains of the antibody, or preferably vectors comprising these cDNAs, and then culturing the transformed cells that produce the recombinant human monoclonal antibody. The hosts are, for example, desired eukaryotic cells, preferably mammalian cells, such as CHO cells, lymphocytes, and myelomas.

Furthermore, techniques to obtain human antibodies by panning with a human antibody library are known. For example, the variable region of a human antibody is expressed as a single chain antibody (scFv) on the surface of a phage, using a phage display method, and phages that bind to the antigen can be selected. By analyzing the genes of selected phages, the DNA sequences encoding the variable regions of human antibodies that bind to the antigen can be determined. If the DNA sequences of scFvs that bind to the antigen are identified, appropriate expression vectors comprising these sequences can be constructed, and then introduced into appropriate hosts and expressed to obtain human antibodies. Such methods are already well known (see WO 92/01047, WO 92/20791, WO 93/06213, WO 93/11236, WO 93/19172, WO 95/01438, and WO 95/15388).

When the antibody genes have been isolated and introduced into an appropriate host, hosts and expression vectors can be used in appropriate combination to produce the antibodies. As eukaryotic host cells, animal cells, plant cells, and fungal cells may be used. The animal cells include: (1) mammalian cells such as CHO, COS, myeloma, baby hamster kidney (BHK), HeLa, and Vero cells; (2) amphibian cells such as *Xenopus* oocytes; or (3) insect cells such as Sf9, Sf21, and Tn5, or silkworms. Known plant cells include cells derived from the *Nicotiana* genus such as *Nicotiana tabacum*, which can be callus-cultured. Known fungal cells include yeasts such as the *Saccharomyces* genus, for example *Saccharomyces cerevisiae*, and filamentous fungi such as the *Aspergillus* genus, for example *Aspergillus niger*. Prokaryotic cells can also be used in production systems that utilize bacterial cells. Known bacterial cells include *Escherichia coli* (*E. coli*) and *Bacillus subtilis*. The antibodies can be obtained by transferring the antibody genes of interest into these cells using transformation, and then culturing the transformed cells in vitro.

The isotypes of the antibodies of the present invention are not limited. The isotypes include, for example, IgG (IgG1, IgG2, IgG3, and IgG4), IgM, IgA (IgA1 and IgA2), IgD, and IgE, with IgG and IgM being preferable. The antibodies of the present invention may also be antibody fragments comprising a portion responsible for antigen binding, or modified fragments thereof. The term "antibody fragment" refers to a portion of a full-length antibody, and generally to a fragment comprising an antigen-binding site or a variable region. Such antibody fragments include, for example, Fab, F(ab')$_2$, Fv, single-chain Fv (scFv) which comprises a heavy chain Fv and a light chain Fv coupled together with an appropriate linker, diabodies, linear antibodies, and multispecific antibodies prepared from antibody fragments. Previously, antibody fragments were produced by digesting natural antibodies with a protease; currently, methods for expressing them as recombinant antibodies using genetic engineering techniques are also known (see Morimoto et al., Journal of Biochemical and Biophysical Methods (1992) 24, 107-17; Brennan et al., Science (1985) 229, 81; Co, M. S. et al., J. Immunol. (1994) 152, 2968-76; Better, M. & Horwitz, A. H., Methods in Enzymology (1989) 178, 476-96; Plueckthun, A. & Skerra, A., Methods in Enzymology (1989) 178, 476-96; Lamoyi, E., Methods in Enzymology (1989) 121, 663-9; Bird, R. E. et al., TIBTECH (1991) 9, 132-7).

An "Fv" fragment is the smallest antibody fragment, and contains a complete antigen recognition site and a binding site. This region is a dimer ($V_H$-$V_L$ dimer) wherein the variable regions of each of the heavy chain and light chain are strongly connected by noncovalent bonds. The three complementarity determining regions (CDRs) of each of the variable regions interact with each other to form an antigen-binding site on the surface of the $V_H$-$V_L$ dimer. In other words, a total of six CDRs from the heavy and light chains function together as antigen-binding site of an antibody. However, a variable region (or a half Fv, which contains only three antigen-specific CDRs) alone is also known to be able to recognize and bind to an antigen, although its affinity is lower than the affinity of the entire binding site. Thus, preferred antibody fragments of the present invention are Fv fragments, but are not limited thereto. Such antibody fragments may be polypeptides that comprise antibody fragments of heavy or light chain CDRs which are conserved, and which can recognize and bind to their antigens.

A Fab fragment (also referred to as F(ab)) also contains a light chain constant region and heavy chain constant region (CH1). For example, papain digestion of an antibody produces two kinds of fragments: an antigen-binding fragment called the Fab fragment, which contains heavy chain and light chain variable regions forming a single antigen-binding site; and the remaining portion called an "Fc", which is readily crystallized. A Fab' fragment is different from a Fab fragment in that a Fab' fragment also has several residues derived from the carboxyl terminus of a heavy chain CH1 region, which contains one or more cysteine residues of the hinge region of an antibody. A Fab' fragment is, however, structurally equivalent to Fab in that both are antigen-binding fragments comprising the variable regions of a heavy chain and light chain, which form a single antigen-binding site. Herein, an antigen-binding fragment which comprises the variable regions of a heavy chain and light chain forming a single antigen-binding site, and which is equivalent to that obtained by papain digestion, is referred to as a "Fab-like antibody", even when it is not identical to the antibody fragment produced by protease digestion. Fab'-SH is Fab' with one or more cysteine residues having free thiol groups in its constant region.

A F(ab') fragment is produced by cleaving the disulfide bond between the cysteine residues in the hinge region of F(ab')$_2$. Other chemically crosslinked antibody fragments are also known to those skilled in the art. Pepsin digestion of an antibody yields two fragments; one is a F(ab')$_2$ fragment which comprises two antigen-binding domains and can cross-react with antigens, and the other is the remaining fragment (referred to as pFc'). Herein, an antibody fragment equivalent to that obtained by pepsin digestion is referred to as a "F(ab')$_2$-like antibody" when it comprises two antigen-binding sites and can cross-react with antigens. Such antibody fragments can also be produced, for example, by genetic engineering. Such antibody fragments can also be isolated, for example, from an antibody phage library described above. Alternatively, F(ab')$_2$—SH fragments can be recovered directly from hosts, such as E. coli, and then allowed to form F(ab')$_2$ fragments by chemical crosslinking (Carter et al., Bio/Technology (1992) 10, 163-7). In an alternative method, F(ab')$_2$ fragments can be isolated directly from a culture of recombinant hosts.

Furthermore, antibodies for use in the present invention may be multispecific antibodies. A multispecific antibody is an antibody that has specificity to at least two different kinds of antigens. Although such molecules usually bind to two antigens (i.e., bispecific antibodies), herein "multispecific antibody" encompasses antibodies with specificity to more than two antigens (e.g., three antigens). The multispecific antibodies can be full-length antibodies or fragments thereof (e.g., F(ab')$_2$ bispecific antibody). Bispecific antibodies can be prepared by crosslinking the heavy and light chains of two types of antibodies (HL pairs), or from bispecific-antibody-producing cells produced by fusing hybridomas that produce different monoclonal antibodies (Millstein et al., Nature (1983) 305, 537-9). Alternatively, bispecific antibodies can be prepared by genetic engineering. Specifically, the variable domain of an antibody with binding specificity is fused to the constant domain sequence of an immunoglobulin. The above-mentioned constant domain sequence preferably comprises at least a part of the hinge, CH2, and the CH3 regions of the heavy chain constant domain of the immunoglobulin. Preferably, the CH1 region of the heavy chain required for binding with the light chain is also included. A DNA encoding the immunoglobulin heavy chain fusion is inserted into an expression vector to transform an appropriate host organism. As necessary, a DNA encoding the immunoglobulin light chain is also inserted into an expression vector, different to that of the immunoglobulin heavy chain fusion, to transform the host organism. There are cases where the antibody yield increases when the chain ratio is not identical. In such cases, it is more convenient to insert each of the genes into separate vectors, since the expression ratio of each of the chains can be controlled. However, genes encoding a number of chains can also be inserted into one vector.

The term "diabody (Db)" refers to a bivalent antibody fragment constructed by gene fusion (for example, P. Holliger et al., Proc. Natl. Acad. Sci. USA (1993) 90, 6444-8; EP 404,097, WO 93/11161). In general, a diabody is a dimer of two polypeptide chains. In each of the polypeptide chains, a light chain variable region ($V_L$) and a heavy chain variable region ($V_H$) in an identical chain are connected via a short linker, for example, a linker of about five residues, so that they cannot bind to each other. Because the linker between the two is short, the $V_L$ and $V_H$ in the same polypeptide chain cannot form a single chain V region fragment, but instead form a dimer. Thus, a diabody has two antigen-binding domains. When the $V_L$ and $V_H$ regions against two types of antigens (a and b) are combined to form $V_L$a-$V_H$b and $V_L$b-$V_H$a via a linker of about five residues, and then co-expressed, they are secreted as bispecific Dbs. The antibodies used in the present invention may be such Dbs.

A single-chain antibody (also referred to as "scFv") can be prepared by linking a heavy chain V region and a light chain V region of an antibody (for a review of scFv, see Pluckthun "The Pharmacology of Monoclonal Antibodies" Vol. 113, eds. Rosenburg and Moore, Springer Verlag, New York, (1994) 269-315). Methods for preparing single-chain antibodies are known in the art (see, for example, U.S. Pat. Nos. 4,946,778, 5,260,203, 5,091,513, and 5,455,030). In such scFvs, the heavy chain V region and the light chain V region are linked together via a linker, preferably, a polypeptide linker (Huston, J. S. et al., Proc. Natl. Acad. Sci. USA (1988) 85, 5879-83). The heavy chain V region and the light chain V region in a scFv may be derived from the same antibody, or from different antibodies. The peptide linker used to ligate the V regions may be any single-chain peptide consisting of 12 to 19 residues. A DNA encoding a scFv can be amplified by PCR using, as a template, either the entire DNA, or a partial DNA encoding a desired amino acid sequence, selected from a DNA encoding the heavy chain of the above antibody or the V region thereof, and a DNA encoding the light chain of the above antibody or the V region thereof; and using a primer pair that defines the two ends. Further amplification can be subsequently conducted using a combination of the DNA encoding the peptide linker portion, and the primer pair that defines both ends of the DNA to be ligated to the heavy and light chain respectively. After constructing DNAs encoding scFvs, conventional methods can be used to obtain expression vectors comprising these DNAs, and hosts transformed by these expression vectors. Furthermore, scFvs can be obtained according to conventional methods using the resulting hosts. These antibody fragments can be produced in hosts by obtaining genes that encode the antibody fragments and expressing these as outlined above. Antibodies bound to various types of molecules, such as polyethylene glycols (PEGs), may be used as modified antibodies. Methods for modifying antibodies are already established in the art. The term "antibody" used in the present invention also encompasses the above-described antibodies.

The antibodies of the present invention may also be sc(Fv) 2. In the present invention, sc(Fv)2 are single-chain minibodies produced by linking four or more antibody variable regions with linkers and such. The sc(Fv)2 include, for example, antibodies with the following arrangement: [variable region 1] (linker 1) [variable region 2] (linker 2) [variable region 3] (linker 3) [variable region 4].

sc(Fv)2 are generally single-chain antibodies produced by linking two VHs and two VLs, four variable regions in total, with linkers and such (Hudson et al., J. Immunol. Methods (1999) 231, 177-189). The two VHs and two VLs may also be derived from different monoclonal antibodies.

sc(Fv)2 can be produced by methods known to those skilled in the art, for example, by linking an scFv with a linker. scFv contain the VH and VL of an antibody, and these regions exist on a single polypeptide chain (for a review of scFv, see Pluckthun "The Pharmacology of Monoclonal Antibodies" Vol. 113, eds. Rosenburg and Moore, Springer Verlag, New York (1994) pp. 269-315).

The sc(Fv)2 of the present invention include antibodies in which two VHs and two VLs are arranged in the order of: VH, VL, VH, and VL ([VH] linker [VL] linker [VH] linker [VL]), beginning from the N terminus of a single-chain polypeptide; however the order of the two VHs and two VLs is not limited to the above arrangement, and they may be arranged in any order. Examples of arrangements are listed below:

[VL] linker [VH] linker [VH] linker [VL]
[VH] linker [VL] linker [VL] linker [VH]
[VH] linker [VH] linker [VL] linker [VL]
[VL] linker [VL] linker [VH] linker [VH]
[VL] linker [VH] linker [VL] linker [VH]

The sc(Fv)2 of the present invention may also comprise amino acid sequences in addition to the antibody variable regions and linkers.

The variable regions used in the present invention may be entire variable regions, or partial sequences of variable regions, as long as they retain antigen-binding activity. Furthermore, some amino acid sequences in the variable regions may comprise substitutions, deletions, additions, insertions, and such. For example, the variable regions may be chimerized or humanized to reduce the antigenicity.

Other proteins, such as an Fc domain of an IgG, may be fused with the sc(Fv)2 of the present invention at the N or C terminus (Clinical Cancer Research (2004) 10, 1274-1281). Such proteins to be fused can be appropriately selected by those skilled in the art. The sc(Fv)2 of the present invention may be conjugated with carrier polymers, such as PEGs, or organic compounds, such as anticancer agents. Alternatively, sugar chains can be added by inserting a glycosylation sequence.

The linkers for linking the variable regions of an antibody can be arbitrary peptide linkers that can be introduced by genetic engineering, or synthetic linkers (for example, see Protein Engineering (1996) 9 (3), 299-305); however, peptide linkers are preferred in the present invention. There are no limitations as to the length of the peptide linkers. The length can be appropriately selected by those skilled in the art, depending on the purpose, and is preferably five amino acids or more (the upper limit is not particularly limited; the length is typically 30 amino acids or less, preferably 20 amino acids or less), and more preferably 15 amino acids. When an sc(Fv)2 comprises three peptide linkers, the lengths may be identical or different.

For example, such peptide linkers include:
Ser
Gly Ser
Gly Gly Ser
Ser Gly Gly
Gly Gly Gly Ser
Ser Gly Gly Gly
Gly Gly Gly Gly Ser
Ser Gly Gly Gly Gly
Gly Gly Gly Gly Gly Ser
Ser Gly Gly Gly Gly Gly
Gly Gly Gly Gly Gly Gly Ser
Ser Gly Gly Gly Gly Gly Gly
(Gly Gly Gly Gly Ser)n
(Ser Gly Gly Gly Gly)n
where n is an integer of one or more. The lengths and sequences of peptide linkers can be appropriately selected by those skilled in the art, depending on the purpose.

Synthetic linkers (chemical cross-linking agents) include cross-linking agents routinely used to cross-link peptides; for example: N-hydroxy succinimide (NHS), disuccinimidyl suberate (DSS), bis(sulfosuccinimidyl) suberate (BS$^3$), dithiobis(succinimidyl propionate) (DSP), dithiobis(sulfosuccinimidyl propionate) (DTSSP), ethylene glycol bis(succinimidyl succinate) (EGS), ethylene glycol bis(sulfosuccinimidyl succinate) (sulfo-EGS), disuccinimidyl tartrate (DST), disulfosuccinimidyl tartrate (sulfo-DST), bis[2-(succinimidoxycarbonyloxy)ethyl]sulfone (BSOCOES), and bis[2-(sulfosuccinimidoxycarbonyloxy)ethyl]sulfone (sulfo-BSOCOES). These cross-linking agents are commercially available.

In general, three linkers are required to link four antibody variable regions together. The linkers to be used may be of the same or different types.

The antibodies obtained in the present invention can be purified to homogeneity. The antibodies can be isolated and purified by methods routinely used to isolate and purify proteins. The antibodies can be isolated and purified by the combined use of one or more methods appropriately selected from column chromatography, filtration, ultrafiltration, salting out, dialysis, preparative polyacrylamide gel electrophoresis, and isoelectrofocusing, for example (Strategies for Protein Purification and Characterization, A Laboratory Course Manual, Daniel R. Marshak et al. eds., Cold Spring Harbor Laboratory Press (1996); Antibodies, A Laboratory Manual, Ed Harlow and David Lane, Cold Spring Harbor Laboratory (1988)). Such methods are not limited to those listed above. Chromatographic methods include affinity chromatography, ion exchange chromatography, hydrophobic chromatography, gel filtration, reverse-phase chromatography, and adsorption chromatography. These chromatographic methods can be practiced using liquid phase chromatography, such as HPLC and FPLC. Columns to be used in affinity chromatography include protein A columns and protein G columns. For example, protein A columns include Hyper D, POROS, and Sepharose F.F. (Pharmacia). Antibodies can also be purified by utilizing antigen binding, using carriers on which antigens have been immobilized.

The agents for inducing and/or enhancing liver regeneration of the present invention comprise anti-PCI antibodies obtainable by the procedures described above as active ingredients. The phrase "comprise [antibodies of the present invention] as active ingredients" means comprising an antibody of the present invention as at least one active ingredient, and does not limit the content of the antibodies of the present invention. Furthermore, the agents for inducing and/or enhancing liver regeneration of the present invention may comprise not only anti-PCI antibodies, but also other active ingredients that induce or enhance liver regeneration, for example, HGF.

The antibodies of the present invention can be formulated according to standard methods (see, for example, Remington's Pharmaceutical Science, latest edition, Mark Publishing Company, Easton, USA). Further, they may comprise pharmaceutically acceptable carriers and/or additives if necessary. For example, they may contain surfactants (for example, PEG and TWEEN™ (polysorbate)), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents. However, the carriers that can be comprised in the agents for inducing and/or enhancing liver regeneration of the present invention are not limited to this list. In fact, other commonly used carriers can be appropriately comprised, such as light anhydrous silicic acid, lactose, crystalline cellulose, mannitol, starch, carmelose calcium, carmelose sodium, hydroxypropylcellulose, hydroxypropylmethylcellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, inorganic salt, and so on. The compositions may also comprise other low-molecular-weight polypeptides, proteins such as serum albumin, gelatin, and immunoglobulin, and amino acids such as glycine, glutamine, asparagine, arginine, and lysine. When the composition is prepared as an aqueous solution for injection, antibodies may be dissolved in an isotonic solution comprising, for example, physiological saline, dextrose, and other adjuvants. The adjuvants may include, for example, D-sorbitol, D-mannose, D-mannitol, and sodium chloride. In addition, appropriate solubilizing agents, for example, alcohols (for example, ethanol), polyalcohols (for example, propylene glycols and PEGs), and non-ionic detergents (polysorbate 80 and HCO-50) may be used concomitantly.

If necessary, the antibodies of the present invention may be encapsulated in microcapsules (microcapsules made of hydroxycellulose, gelatin, polymethylmethacrylate, and the like), and made into components of colloidal drug delivery systems (liposomes, albumin microspheres, microemulsions, nano-particles, and nano-capsules) (for example, see "Remington's Pharmaceutical Science 16th edition", Oslo Ed. (1980)). Moreover, methods for making sustained-release drugs are known, and these can be applied for the antibodies of the present invention (Langer et al., J. Biomed. Mater. Res. (1981) 15, 167-277; Langer, Chem. Tech. (1982) 12, 98-105; U.S. Pat. No. 3,773,919; European Patent Application (EP) No. 58,481; Sidman et al., Biopolymers (1983) 22, 547-56; EP 133,988).

The agents for inducing and/or enhancing liver regeneration of the present invention can be administered either orally or parenterally, but are preferably administered parenterally. Specifically, the agents may be administered to patients via injections, nasal administration, pulmonary administration, and cutaneous administration. For example, injections can be administered systemically or locally by intravenous injection, intramuscular injection, intraperitoneal injection, or subcutaneous injection. Furthermore, the method of administration can be appropriately selected according to the age and symptoms of the patient. A single dose can be selected from within the range of 0.0001 mg to 1,000 mg per kg of body weight. Alternatively, the dose can be selected from within the range of 0.001 to 100,000 mg/body for each patient. However, the doses of the agents for inducing and/or enhancing liver regeneration of the present invention are not limited to these examples.

In addition, genes encoding the above antibodies of the present invention may be inserted into vectors used in gene therapy to prepare agents for inducing and/or enhancing liver regeneration used in gene therapy. Such genes can be administered by direct injection using naked plasmids, and also by packaging in liposomes, producing as a variety of viral vectors such as retroviral vectors, adenovirus vectors, vaccinia virus vectors, poxvirus vectors, adenoassociated virus vectors, and HVJ vectors (Adolph, "Virus Genome Methods", CRC Press, Florida (1996)), or by coating onto carrier beads such as colloidal gold particles (for example, WO93/17706). However, any method can be used for administration, as long as the antibodies are expressed in vivo and exercise their function. Preferably, sufficient doses may be administered by suitable parenteral routes (such as injecting intravenously, intraperitoneally, subcutaneously, percutaneously, or into adipose tissues or mammary glands, inhalation, intramuscular injection, infusion, gas-induced particle bombardment (using electron guns and such), or through mucosa, for example, using nose drops). Alternatively, genes encoding the antibodies may be administered into cells ex vivo using liposome transfection, particle bombardment (U.S. Pat. No. 4,945,050), or viral infection, and the cells may be reintroduced into animals.

2. Therapeutic Agents for Hepatic Diseases

The above-described agents for inducing and/or enhancing liver regeneration that comprise anti-PCI antibodies as active ingredients are used to induce or enhance liver regeneration, and are effective against hepatic diseases such as various types of hepatitis, including drug-induced hepatitis, fulminant hepatitis, and alcoholic hepatitis, and cirrhosis, which demand liver regeneration. The present invention thus provides therapeutic agents for hepatic diseases, where the agents comprise anti-PCI antibodies as active ingredients.

3. Agents for Regulating Liver Regeneration

The present inventors discovered that PCI retarded in vivo tissue regeneration and/or repair. They revealed that since PCI had the above characteristics, it could be used as an agent for regulating liver regeneration. The present invention thus provides agents for regulating liver regeneration, which comprise PCI as an active ingredient. The agents for regulating liver regeneration that comprise PCI as an active ingredient are agents that retard liver regeneration.

PCI is a single-chain glycoprotein with a molecular weight of about 57 kDa. The PCI to be used in the present invention may be natural PCI or artificially produced PCI. Human PCI and other mammalian PCIs are known (Suzuki, K. et al., J. Biol. Chem. (1987) 262, 611-6), and can be preferably used in the present invention. Mammalian PCIs include, for example, mouse, rat, and bovine PCIs, but are not limited thereto in the present invention (Zechmeister-Machhart, M. et al., Gene (1997) 186 (1), 61-6; Wakita, T. et al., FEBS Lett. (1998) 429 (3), 263-8; Yuasa, J. et al., Thromb. Haemost. (2000) 83 (2), 262-7). In the present invention, preferred PCIs include polypeptides comprising the amino acid sequence of SEQ ID NO: 5, encoded by the nucleotide sequence of SEQ ID NO: 4. Any PCI can be used in the present invention, as long as it can form a complex with HGFa and can inhibit HGFa activity; in addition to polypeptides comprising an entire PCI, PCI fragments retaining binding activity to HGFa and the ability to inhibit the biological activity can also be used. Polypeptides comprising an entire PCI include fusion polypeptides modified with other peptides.

Any PCI can be used in the present invention, as long as it can form a complex with HGFa and can inhibit HGFa activity. Therefore, the PCI may be a polypeptide comprising the amino acid sequence of SEQ ID NO: 5, as well as a variant amino acid sequence with an alteration of one or more amino acid residues in this amino acid sequence. For example, the alterations may improve in vivo stability of PCI and the physical and biological properties of PCI, such as binding activity to HGFa. Such alterations can be achieved by methods such as site-directed mutagenesis (see Kunkel, Proc. Natl. Acad. Sci. USA (1985) 82, 488), PCR-based mutagenesis, and cassette mutagenesis. Such mutants exhibit at least 70% amino acid sequence identity to the original amino acid sequence, preferably at least 75%, more preferably at least 80%, even more preferably at least 85%, still more preferably at least 90%, and yet the most preferably at least 95% identity. Herein, sequence identity is defined as the percentage of residues identical to those in the original amino acid sequence of the PCI, determined after the sequences are aligned and gaps are appropriately introduced to maximize sequence identity as necessary. Specifically, the above description of amino acid sequence identity for mutant antibodies can be referred to.

The PCIs to be used in the present invention form a complex with HGFa and inhibit HGFa activity. The activity of such PCIs can be tested by determining the binding activity between PCI and HGFa, or the HGFa activity after incubating a mixture of PCI and HGFa. Whether or not a PCI to be used inhibits the desired effect of inhibiting HGFa activity, and the percentage of that inhibition, can be determined based on HGFa activity levels when PCI is absent (HGFa activity without PCI inhibition). HGFa activity assays can be carried out by reference to descriptions regarding the determination of the activity of anti-PCI antibodies.

PCIs can be isolated from natural sources, such as blood, urine, seminal fluid, synovial fluid, or cells or tissues expressing PCI, based on its physical properties and the like. Alternatively, PCIs may be chemically synthesized based on known sequence information. Alternatively, PCIs can be obtained by using genetic recombination techniques to transform host cells with a gene encoding a PCI, preferably a vector carrying the gene, then culturing the resulting transformed cells that produce the recombinant PCI, and collecting PCI from the cells or culture supernatant. Recombinant PCI proteins can be prepared, for example, as described in Example 1.

Vectors suitable for producing PCI using genetic engineering methods include various vectors using viruses, cosmids, plasmids, bacteriophages, and the like (Molecular Cloning $2^{nd}$ ed., Cold Spring Harbor Press (1989); Current Protocols in Molecular Biology, John Wiley & Sons (1987)). Such vectors comprise appropriate regulatory sequences, and a PCI-encoding gene is inserted so as to maintain the correct reading frame relative to the regulatory sequence, such that the PCI is expressed when introduced into desired host cells. Any genes encoding PCI can be used as the above-mentioned PCI-encoding gene, as long as they can be expressed by the selected vector and host; preferable genes include cDNAs, however, RNAs or the like may be used in some cases. When the host cell is a prokaryotic cell, the "regulatory sequence" comprises a promoter, a ribosome-binding site, and a terminator. Alternatively, when the host is a eukaryotic cell, the "regulatory sequence" comprises a promoter and terminator, and, as necessary, an enhancer, splicing signal, transcription factor, transactivator, poly A signal, and/or polyadenylation signal, and so on. Such expression vectors for PCI may comprise selection markers for the convenience of selection of transformed host cells, if necessary. Furthermore, PCI genes with signal peptide-encoding sequences attached may be inserted into vectors to translocate expressed cellular PCIs into the lumen of the endoplasmic reticulum or the extracellular space, or alternatively into the periplasm when the host cells are gram-negative bacteria. Such signal peptides may be original PCI signals or may be derived from different proteins, as long as they are properly recognized in selected host cells. Furthermore, linkers, start codons, stop codons, and such may be added, if required.

Genes can be inserted into vectors via ligase reactions using restriction enzyme sites (Molecular Cloning $2^{nd}$ ed., Cold Spring Harbor Press (1989) Section 5.61-5.63; Current Protocols in Molecular Biology, John Wiley & Sons (1987) 11.4-11.11). Such vectors may be designed by considering codon usage in the host cells to be used, and selecting nucleotide sequences that allow high efficiency expression (Grantham et al., Nucleic Acids Res. (1981) 9, r43-74).

When such vectors are introduced into adequate hosts, the above expression vectors and hosts can be used in combinations appropriate to PCI production. Animal cells, plant cells, and fungal cells may be used as the eukaryotic host cells. The animal cells include: (1) mammalian cells, for example, CHO, COS, myeloma, BHK (baby hamster kidney), HeLa, and Vero cells; (2) amphibian cells, for example, *Xenopus* oocytes; or (3) insect cells, for example, Sf9, Sf21, and Tn5 cells, or silkworms. Known plant cells include cells derived from the *Nicotiana* genus, such as *Nicotiana tabacum*, which can be callus cultured. Known fungal cells include yeasts, such as the *Saccharomyces* genus, for example *Saccharomyces cerevisiae*, and filamentous fungi, such as the *Aspergillus* genus, for example, *Aspergillus niger*. Prokaryotic cells can also be used in production systems that utilize bacterial cells. Known bacterial cells include *E. coli* and *Bacillus subtilis*. PCI can be obtained by transferring a PCI gene into these cells using transformation, and then culturing the transformed cells in vitro.

Host cells can be transformed using methods suited to selected hosts and vectors. For example, when prokaryotic cells are used as the host, known methods include calcium treatment and electroporation. Examples also include the *Agrobacterium* method for plant cells, and the calcium phosphate precipitation method for mammalian cells. The present invention is not particularly limited to the methods described above. The present invention can use various known methods, including nuclear microinjection, cell fusion, electroporation, protoplast fusion, lipofectamine methods (GIBCO BRL), DEAE-dextran methods, and methods using FuGENE6® reagent (Boehringer-Mannheim).

Host cells can be cultured by known methods suited to selected cells. For example, when animal cells are used as the host, the cells may be cultured using a medium, such as DMEM, MEM, RPMI-1640, 199, or IMDM, if required, supplemented with fetal calf serum (FCS) and such, at a pH of about 6 to 8 at 30° C. to 40° C. for about 15 to 200 hours. In addition, if necessary, required treatments such as medium exchange, aeration, and stirring can be given during culture.

PCI is preferably used after purification by known methods. PCI can be purified to homogeneity by conventional protein purification methods. PCI can be separated and purified, for example, by appropriately selecting and combining chromatographic columns, filters, ultrafiltration, salting out, dialysis, preparative polyacrylamide gel electrophoresis, isoelectrofocusing, and such (Strategies for Protein Purification and Characterization, A Laboratory Course Manual, Daniel R. Marshak et al., eds., Cold Spring Harbor Laboratory Press (1996); Antibodies, A Laboratory Manual, Ed Harlow and David Lane, Cold Spring Harbor Laboratory (1988)); however, the present invention is not limited thereto. Such chromatography includes affinity chromatography, ion-exchange chromatography, hydrophobic chromatography, gel filtration, reverse phase chromatography, adsorption chromatography, and the like. The chromatographic methods can be conducted using liquid chromatography, such as HPLC and FPLC. Affinity chromatography can be conducted, for example, using antibodies against PCI. PCI can be preferably purified by the method described in Example 2 below, but this is not limiting.

The agents for regulating liver regeneration of the present invention comprise PCIs obtainable as described above as active ingredients. The phrase "comprise PCIs . . . as active ingredients" means comprising a PCI as at least one active ingredient, and does not indicate any limitation as to the PCI content. Furthermore, the agents for regulating liver regeneration of the present invention may comprise other active ingredients for regulating liver regeneration in combination with PCI.

PCI can be formulated according to standard methods (see, for example, Remington's Pharmaceutical Science, latest edition, Mark Publishing Company, Easton, USA), and may comprise pharmaceutically acceptable carriers and/or additives. For example, carriers may include detergents (for example, PEG and TWEEN™ (polysorbate)), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents. However, the carriers are not limited to this list, and the agents for inducing and/or enhancing liver regeneration of the present invention may comprise other appropriate conventional carriers. Specifically, such carriers include light anhydrous silicic acid, lactose, crystalline cellulose, mannitol, starch, carmelose calcium, carmelose sodium, hydroxypropylcellulose, hydroxypropylmethylcellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, inorganic salt, and so on. The agents may also comprise other low-molecular-weight polypeptides; proteins, such as serum albumin, gelatin, and immunoglobulin; and amino acids, such as glycine, glutamine, asparagine, arginine, and lysine. When the agents are prepared as aqueous solutions for injection, they can comprise isotonic solutions comprising, for example, physiological saline, dextrose, and other adjuvants, including, for example, D-sorbitol, D-mannose, D-mannitol, and sodium chloride, which can also comprise appropriate solubilizing agents, for example, alcohols (for example, ethanol), polyalcohols (for example, propylene glycol and PEGs), and non-ionic detergents (polysorbate 80 and HCO-50).

If necessary, PCI may be encapsulated in microcapsules (microcapsules made of hydroxymethylcellulose, gelatin, polymethylmethacrylate, and the like), and made into components of colloidal drug delivery systems (liposomes, albumin microspheres, microemulsions, nano-particles, and nano-capsules) (for example, see "Remington's Pharmaceutical Science 16th edition", Oslo Ed. (1980)). Moreover, methods for preparing sustained-release drugs are known, and these can be applied to PCI (Langer et al., J. Biomed. Mater. Res. (1981) 15, 167-277; Langer, Chem. Tech. (1982) 12, 98-105; U.S. Pat. No. 3,773,919; European Patent Application (EP) No. 58,481; Sidman et al., Biopolymers (1983) 22, 547-56; EP No. 133,988).

The agents for inducing and/or enhancing liver regeneration can be administered either orally or parenterally, but are preferably administered parenterally. Specifically, the agents can be administered to patients by injection, nasally, transpulmonarily, and percutaneously. For example, injections can be administered systemically or locally by intravenous injection, intramuscular injection, intraperitoneal injection, or subcutaneous injection. Furthermore, the method of administration can be appropriately selected according to the age and symptoms of the patient. A single dose can be selected from between 0.0001 to 1,000 mg per kg of body weight. Alternatively, the dose can be selected from between 0.001 to 100,000 mg/body for each patient. However, the doses of the agents for regulating liver regeneration of the present invention are not limited to these examples.

In addition, the above-described genes encoding PCIs may be used as gene therapy agents for regulating liver regeneration by transferring the genes into vectors for such use. The genes can be administered by direct injection using naked plasmids, by packaging in liposomes and such, or by forming as a variety of viral vectors, such as retroviral vectors, adenovirus vectors, vaccinia virus vectors, poxvirus vectors, adenoassociated virus vectors, and HVJ vectors (see Adolph, Virus Genome Methods, CRC Press, Florida (1996)), or by coating onto carrier beads, such as colloidal gold particles (see, for example, WO 93/17706). However, any methods can be used for administration, as long as PCI is expressed and exercises its function in vivo. Preferably, a sufficient dose may be administered by a suitable parenteral route (such as injecting intravenously, intraperitoneally, subcutaneously, intracutaneously, or into adipose tissues or mammary gland tissues, inhalation, intramuscular injection, infusion, gas-induced particle bombardment (using electron guns and such), or through mucosa, for example, using nose drops). Alternatively, genes encoding PCI may be administered into cells ex vivo using liposome transfection, particle bombardment (U.S. Pat. No. 4,945,050), or viral infection, and the cells may be reintroduced into animals.

All prior-art documents cited herein are incorporated by reference herein.

EXAMPLES

Herein below, the present invention will be specifically described using examples; however, it is not to be construed as being limited thereto. All publications cited herein constitute a part of the present invention.

Example 1

Construction of PCI Expression Vectors 1.1 Cloning of PCI Gene

A full-length PCI gene was cloned by PCR using the primers indicated below.

```
                                                (SEQ ID NO: 1)
PCI-up:  5'- ACG AAT TCC ACC ATG CAG CTC TTC CTC (SEQ ID NO: 2)
PCI-low: 5'- CTG GAT CCT CAG GGG CGG TTC ACT TTG C
```

Figure 1:
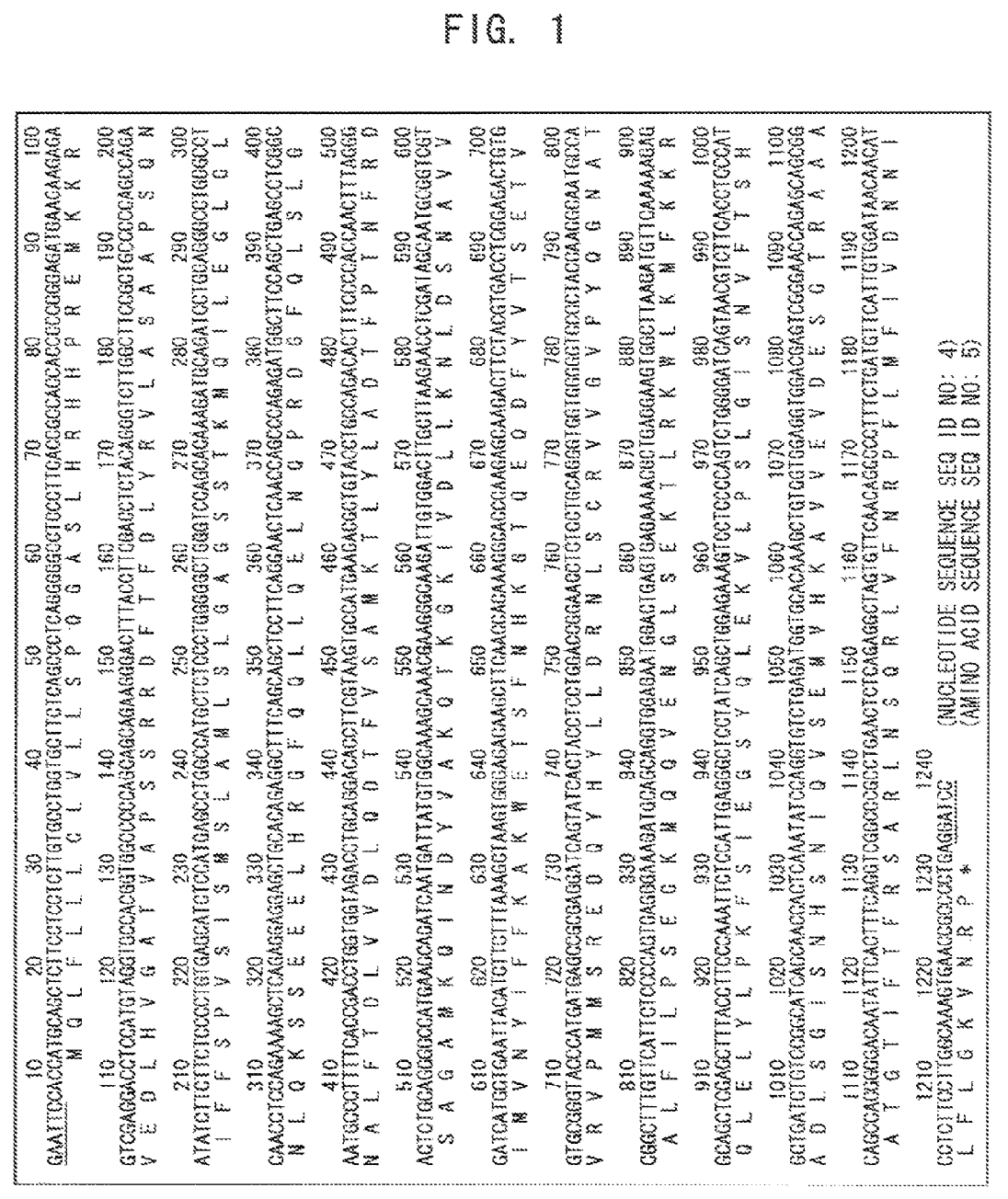

The human PCI gene which comprises the entire ORF containing an EcoRI sequence at the 5' end and a BamHI sequence at the 3' end was amplified by PCR, using the primers described above and Human kidney marathon ready cDNA (Clontech) as a template. The amplified DNA fragment was digested with EcoRI and BamHI, and inserted between the cleaved EcoRI and BamHI sites in the animal cell expression vector pCHOI. The nucleotide sequence of the PCI gene in the vector was determined and a plasmid containing the desired sequence was selected as the pCHOI-PCI vector to use in the following experiments (FIG. 1).

A Flag-tagged PCI expression vector (PCI-Flag) was constructed as described below. First, the PCI gene was amplified by PCR using the pCHOI-PCI vector as a template, and PCI-up and PCI-low2 primers.

```
                                          (SEQ ID NO: 3)
PCI-low2: 5'- TTG GAT CCG GGG TTC ACT TTG CCA AG
```

Figure 2:
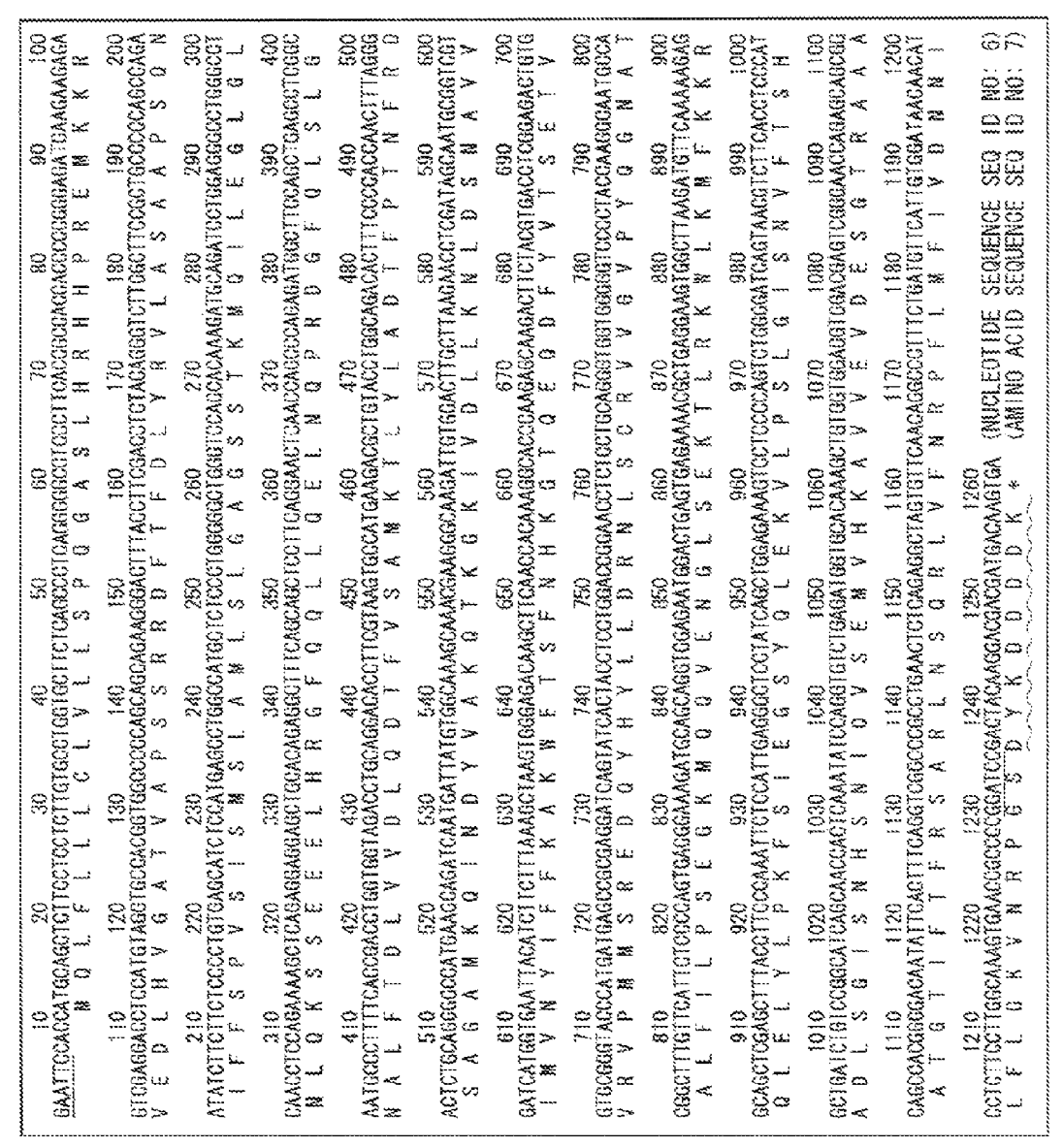

The DNA fragment was digested with EcoRI and BamHI, and then inserted between the cleaved EcoRI and BamHI sites on the animal cell expression vector pCHOII-Flag, which comprises a Flag tag immediately after the cloning site. Accordingly, a Flag-tagged PCI expression vector pCHOII-PCI-Flag was obtained (FIG. 2). The inserted nucleotide sequence confirmed that the vector certainly encoded PCI-Flag.

1.2 Establishment of PCI and PCI-Flag Producing Cell Lines

The pCHOI-PCI and pCHOII-PCI-Flag plasmids were linearized by PvuI digestion. 30 µg of the DNAs were introduced into CHO cells (DXB11 strain) by electroporation. Then, the cells were cultured in α(−)MEM (nucleic acid-free) (GIBCO BRL CAT# 12561-056) containing 5% FBS (GIBCO BRL CAT# 10099-141). Cell lines producing PCI or PCI-Flag were selected. The selected cell lines were cultured in the same medium containing a final concentration of 50 nM MTX to establish cell lines that highly produce PCI and PCI-Flag. The expressions of PCI and PCI-Flag were confirmed using an anti-PCI antibody (Affinity Biologicals CAT# GAPCI-IG).

Example 2

Purification of PCI-Flag

The PCI-Flag-overexpressing CHO cell lines were cultured in roller bottles (1,700 cm$^2$) using α(−)MEM (nucleic acid-free) containing 5% FBS. The cells were cultured until confluent (37° C., 0.5 rpm), and then the media were removed. The cells were washed with PBS, and further cultured in CHO-S-SFMII medium (GIBCO BRL CAT# 12052-098) for 72 hours. The culture supernatant obtained was centrifuged to remove cell debris, filtered through 0.45 µm filters, and then used in the purification step described below. That is, the culture supernatant was loaded onto a CM SEPHAROSE™ Fast Flow column (Amersham CAT# 17-0719-01) equilibrated with 50 mM Tris buffer (pH7.0) containing 0.05% TWEEN™ (polysorbate) 20. The column was washed, and then eluted with the same buffer containing 400 mM NaCl. The eluted fraction was diluted to adjust the NaCl concentration to 200 mM. The diluted fraction was loaded onto an anti-Flag M2 agarose affinity gel column (SIGMA CAT# A-2220) equilibrated with 50 mM Tris buffer (pH7.4) containing 150 mM NaCl and 0.05% TWEEN™ (polysorbate) 20. The column was eluted with 100 mM glycine buffer (pH3.5) containing 0.05% TWEEN™ (polysorbate) 20. The eluted fraction was immediately neutralized with 1 M Tris buffer (pH8.0). Then, the fraction containing PCI-Flag was loaded onto a CM SEPHAROSE™ Fast Flow column equilibrated with 50 mM phosphate buffer (pH7.0) containing 0.05% TWEEN™ (polysorbate) 20, and eluted with the same buffer containing 400 mM NaCl for the purpose of solvent displacement. The eluted sample was then concentrated by ultrafiltration using CENTRICON® YM-3 (Amicon) to prepare PCI-Flag. The purified protein was fractionated by SDS-PAGE, and then confirmed by Coomassie Blue staining, and by Western analysis using an anti-PCI antibody after transferring onto a PVDF membrane (FIG. 3A).

Example 3

Purification of PCI

The PCI-overexpressing CHO cell line was cultured using roller bottles (1,700 cm$^2$) and the culture supernatant was prepared by the same method as described above in Example 2. The culture supernatant was loaded onto a CM SEPHAROSE™ Fast Flow column equilibrated with 50 mM Tris buffer (pH7.0) containing 0.05% TWEEN™ (polysorbate) 20. After washing, the column was eluted with the same buffer containing 400 mM NaCl. Then, the PCI-containing fraction was loaded onto a HITRAP™ Heparin HP (Amersham CAT# 17-0407-01) column equilibrated with 10 mM phosphate buffer (pH7.0) containing 0.05% TWEEN™ (polysorbate) 20. The sample was eluted with a NaCl step gradient (concentration from 0 mM to 1,000 mM). The eluted fraction was loaded onto a SUPERDEX® 200 26/60 column (Amersham CAT# 17-1071-01) and fractionated by molecular weight. For the solvent, PBS containing 0.01% TWEEN™ (polysorbate) 20 (PBS-T) was used. This process was repeated twice for PCI purification. The purified protein was fractionated by SDS-PAGE, and then confirmed by Coomassie Blue staining, and by Western analysis using an anti-PCI antibody after transferring onto a PVDF membrane (FIG. 3B).

Example 4

Preparation of Anti-PCI Antibodies Having PCI-Neutralizing Activity 4.1 Immunization and Preparation of Hybridomas Five Balb/c mice (female, 13 weeks old; Charles River Japan, Inc.) were immunized with PCI-Flag as an antigen according to conventional methods. 100 µg/head of the antigen was used for the first immunization. The antigen was emulsified using FCA [Freund's complete adjuvant (H37 Ra), Difco (3113-60), Becton Dickinson (CAT# 231131)], and injected subcutaneously into the mice. After two weeks, 50 µg/head of the antigen was emulsified using FIA [Freund's incomplete adjuvant, Difco (0639-60), Becton Dickinson (CAT# 263910)] and injected subcutaneously into the mice. Then, booster immunization was carried out five times in total at two-week intervals. The final immunization was carried out by injecting the antigen (50 µg/head) in the caudal vein or subcutaneously. The anti-PCI antibody titer was confirmed to be elevated in sera by ELISA using immunoplates coated with 0.5 µg/ml or 100 µl/well of PCI, then the final immunization was carried out by injecting to the No. 2 mouse in the caudal vein and the No. 4 mouse subcutaneously. Murine myeloma P3U1 cells and murine spleen cells were combined and fused using PEG1500 (Roche Diagonostic, CAT# 783641) according to conventional methods. The respective murine hybridoma cells were cultured in sixteen 96-well culture plates each. HAT selection began on the following day, using HAT medium [10% FBS/RPMI 1640/1x HAT media supplement (SIGMA CAT# H-0262)/4% BM-Condimed H1 Hybridoma cloning supplement (Roche CAT# 1088947)]. Ten days after the fusion, culture supernatants were collected for ELISA screening. ELISA screening was carried out using immunoplates coated with 0.5 µg/ml or 100 µl/well of PCI by the same method as described above for antibody titer assay.

4.2 Screening
4.2.1 ELISA

Positive wells were selected by ELISA screening using PCI. Then, the cells were cloned by expanding in 24-well plates and by limiting dilution (100 cells from a single positive well were placed into separate wells of a 96-well plate). The cloned hybridomas were expanded and antibodies were purified from the culture supernatants. 290 positive wells were selected and the cells were expanded in 24-well plates. Then, the first 111 wells exhibiting higher OD values in the primary screening were selected, and the cells were cloned by limiting dilution. Culture supernatants were collected from the 179 wells not treated with limiting dilution, and the cells were stored. Finally, from the 111 wells treated with limiting dilution, 81 clones stably producing antibodies were established.

4.2.2 aPC/PCI Assay

Figure 4:
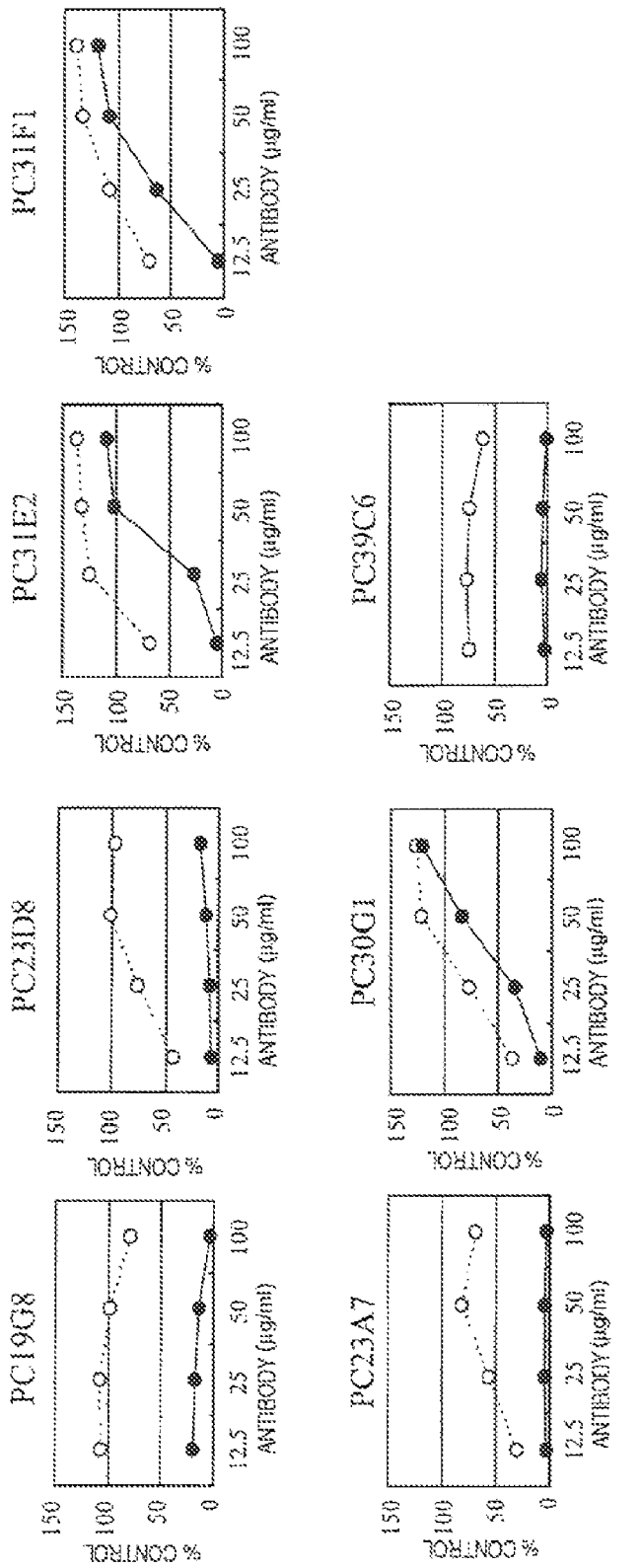
FIG. 4 shows a comparison of the neutralizing activities of anti-PCI antibodies using the aPC/PCI and Thr/TM/PCI assays. Open circles show aPC/PCI assay results and closed circles show Thr/TM/PCI assay results. The level of activity is expressed as a relative value, between 100% activity in the absence of PCI, and 0% activity in the presence of PCI but absence of antibody.

In an aPC/PCI assay for determining PCI-neutralizing activity, following the addition of a hybridoma culture supernatant or purified antibody and 5 µg/ml PCI, the reaction solution (50 mM Tris-HCl (pH8.0), 150 mM NaCl, 2 mM $CaCl_2$, 0.1% BSA, and 5 U/ml Heparin) was incubated at 37° C. for 30 minutes. 0.25 µg/ml aPC was added to the mixture, which was then incubated at 37° C. for another 30 minutes. 0.4 mM Spectrozyme aPC (American Diagnostica Inc.) was added to the mixture. After two hours of incubation at room temperature, the mixture was analyzed by colorimetry at 405 nm (the concentrations indicated above are all final concentrations). 81 samples of monocloned hybridoma culture supernatants were analyzed by aPC/PCI assay, and clones in which aPC activity had been recovered by neutralizing the PCI activity were selected. From clones with strong PCI-neutralizing activity, 16 clones with the strongest PCI-neutralizing activity were selected, and then antibodies were purified from the culture supernatants using Protein G columns. aPC/PCI assays using the purified antibodies confirmed that eight of the 16 clones had a strong dose-dependent neutralizing activity. FIG. 4 shows dose-dependent curves for seven of these clones.

4.2.3 Thrombin (Thr)/Thrombomodulin (TM)/PCI Assay

In a thrombin (Thr)/thrombomodulin (TM)/PCI assay for determining PCI-neutralizing activity, a purified antibody, 5 µg/ml PCI, 2 nM Thr, and 10 nM TM were added to the reaction solution (50 mM Tris-HCl (pH8.0), 150 mM NaCl, 2 mM $CaCl_2$, 0.1% BSA, and 5 U/ml heparin), which was then incubated at 37° C. for 30 minutes, followed by addition of 0.73 µg/ml PC and incubation at 37° C. for 50 minutes. Then, 0.875 µg/ml argatroban was added to the mixture to stop the reaction. 0.4 mM Spectrozyme aPC was added to the reaction solution, followed by two hours of incubation at room temperature, and colorimetry analysis at 405 nm (The concentrations indicated above are all final concentrations).

The seven clones confirmed by the aPC/PCI assay to have neutralizing activity were analyzed by the Thr/TM/PCI assay using purified antibodies. As a result, three (PC31E2, PC31F1, and PC30G1) of the seven clones were confirmed to have a strong dose-dependent neutralizing activity (FIG. 4).

4.3 Purification of Antibodies

Antibodies with an IgG1, IgG2a or IgG2b isotype were purified as follows: The hybridoma culture supernatants were loaded onto a HITRAP™ Protein G HP (Amersham CAT# 17-0404-01) equilibrated with 20 mM phosphate buffer (pH7.0). After washing, the columns were eluted with 0.1 M glycine buffer (pH2.7). The eluted fraction was immediately neutralized with 1 M Tris buffer (pH9.0). Fractions containing the antibody were pooled, and then dialyzed overnight against PBS containing 0.05% TWEEN™ (polysorbate) 20 for solvent displacement. Then, 0.02% $NaN_3$ was added to the dialyzed sample.

4.4 Isotyping of Anti-PCI Antibodies

Isotyping of anti-PCI antibodies was carried out using the ImmunoPure Monoclonal Antibody Isotyping Kit II (PIERCE CAT# 37502) according to the method described in the attached manual. Isotyping analysis of the established 81 anti-PCI antibody clones yielded 70 IgG1 clones, six IgG2a clones, four IgG2b clones, and one IgM clone.

4.5 Kinetic Analyses of Anti-PCI Antibodies Using BIACORE

PCI-Flag was diluted to 25 µg/ml with 10 mM sodium acetate (pH5.0), and then amine-coupled to a sensor chip CM5 (BIACORE; BR-1000-14) using an amine coupling kit (BIACORE; BR-1000-50) according to the method described in the kit. Approximately 3,000 RU of PCI-Flag was immobilized onto the CM5 chip by this treatment. The kinetic analyses described below were performed on BIACORE 2000 using the sensor chip. Each anti-PCI antibody was diluted to 1.25, 2.5, 5, 10 and 20 µg/ml with HBS-EP buffer (BIACORE; BR-1001-88). After the chip was equilibrated with HBS-EP buffer, 40 µl of the antibody solution at each concentration was injected at a flow rate of 20 µl/min. In the association phase, the antibody was injected over two minutes. Then, instead of the antibody, HBS-EP buffer was injected over two minutes in the dissociation phase. After the dissociation phase, 40 µl of 10 mM HCl and then 40 µl of 0.05% SDS were injected continuously to regenerate the sensor chip. The sensorgrams obtained by the procedure described above were superimposed, and the binding rate constant (ka), dissociation rate constant (kd), dissociation constant (KD), and maximal binding (Rmax) were computed using data analysis software (BIAevaluation, ver.3.0).

BIACORE kinetic analyses were performed on the eight clones found by aPC/PCI assay using the purified antibodies to exhibit strong PCI-neutralizing activity. The data revealed that many of the antibodies included exhibit relatively high affinities with a dissociation constant ranged from $10^{-9}$ to $10^{-10}$ M. Table 1 summarizes the characteristics of anti-PCI antibodies from the obtained clones.

TABLE 1

Characteristics of neutralizing antibodies

| Clone | Isotype | aPC/PCI | Thr/TM/PCI (+H) | Kinetic Parameter ka (1/Ms) | kd (1/s) | KD (nM) |
|---|---|---|---|---|---|---|
| PC19G8 | IgG1 | + | − | 1.68E+05 | 2.13E−05 | 0.126 |
| PC23A7 | IgG2a | + | − | 1.51E+05 | 7.17E−05 | 0.473 |
| PC23D8 | IgG2a | + | − | 2.25E+05 | 6.59E−05 | 0.293 |
| PC30G1 | IgG1 | + | + | 1.82E+05 | 4.54E−05 | 0.249 |
| PC31E2 | IgG1 | + | + | 1.75E+05 | 3.13E−04 | 1.79 |
| PC31F1 | IgG1 | + | + | 1.53E+05 | 3.89E−05 | 0.254 |
| PC39C6 | IgG1 | + | − | 8.88E+04 | 4.89E−04 | 5.51 |

Example 5

Analysis of the H Chains and the L Chains of Neutralizing Anti-PCI Antibodies

Using the RNeasy Plant Mini Kits (QIAGEN, CAT# 74904), total RNA was extracted from about $1 \times 10^7$ cells in each antibody-producing hybridoma. Then, cDNA was synthesized from the total RNA using the SMART RACE cDNA Amplification Kit (Clontech, CAT# K1811-1). The H chains and L chains were amplified by 5'-RACE PCR using the Advantage2 PCR Kit with primers specific to the IgG1 constant region for clones PC19G8, PC30G1, PC31E2, PC31F1, and PC39C6, or primers specific to the IgG2a constant region for clones PC23A7 and PC23D8. The amplified H chain and L chain DNA fragments were cloned into pGEM-T easy vector (Promega, CAT# A1360), and their nucleotide sequences were determined.

Amino acid sequences of the H chain and L chain variable regions, which were obtained by analyzing the determined nucleotide sequences, are respectively shown in FIGS. 5 and 6. The amino acid sequences of PC19G8 and PC23D8 were found to be identical, and therefore the antibodies were predicted to be derived from an identical clone. However, class switch was suspected to have taken place considering that the isotypes of PC19G8 and PC23D8 were IgG1 and IgG2a, respectively. PC23A7 and PC39C6 have sequences similar to the antibodies from the two clones described above. This suggests that the epitopes recognized by antibodies of the four clones are in close vicinity. On the other hand, the PC30G1 and PC31F1 sequences show low similarity to the four antibody clones described above. However, these two clones have similar sequences, and thus the epitopes for the two antibodies were predicted to be located close to each other. The PC31E2 sequence was found to have low similarity to the other six clones. PC19G8, PC23A7, PC23D8, and PC39C6 suppressed only the aPC-PCI system, while PC30G1, PC31E2, and PC31F1 suppressed both the aPC-PCI and Thr-TM-PCI systems. Thus, presumably, the sequence-based categorization has closely reflected the pattern of PCI-neutralizing activity.

Example 6

Evaluation of Regulating and Controlling Effect of PCI on Liver Regeneration and Repair A partial hepatectomy model was created using PCI transgenic mice overexpressing human PCI (Journal of Thrombosis and Haemostasis (2004) 2, 949-61). Regulating and controlling effect of PCI on liver regeneration and repair was assessed using the model. A PCI-neutralizing antibody was then administered to these same model mice and its effect on PCI-dependent regulation and control of liver regeneration and repair was evaluated.

6. Evaluation of Regulating and Controlling Effect of PCI on Liver Regeneration and Repair in PCI Transgenic (PCI-TG) Mice 6.1 Mice All animal experiments were approved by the Mie University Review Board for animal experiments. The experiments were carried out according to the guidelines for animal experiments of the National Institute of Health in the USA. Mice introduced with the human PCI gene (PCI-Tg) were developed and characterized using methods described in a previous study (Hayashi, T. et al., J. Thromb. Haemost. (2004) 2, 949-961). PCI-Tg mice and wild type (WT) mice were discriminated between using enzyme immunoassays, as described in a previous study (Hayashi, T. et al., J. Thromb. Haemost. (2004) 2, 949-961). PCI-Tg and wild type (WT) mice were allowed free access to food and water, and housed under temperature-controlled conditions with a 12-hour/12-hour light/dark cycle.

6.2 Partial Hepatectomy and Sample Collection 10- to 12-week-old PCI-Tg and WT mice were used. Their weights were 20 to 30 g, and there was no difference between the groups. Using the same surgical procedure as that described by Higgins and Anderson, two-thirds partial hepatectomies were performed on the mice under diethyl ether inhalation (Higgins, G. M. et al., Arch Pathol (1931) 12, 186-202) (n=6 in each group). Control mice only underwent a laparotomy (n=6 in each group). The mice were anesthetized by intraperitoneal administration of Nembutal at a predetermined time. Blood samples were collected by cardiopuncture, and 0.38% sodium citrate (Nacalai Tesque Inc., Kyoto, Japan) was added thereto. The remnant livers were washed with saline and excised. After determining their weights, the blood and liver samples were frozen in liquid nitrogen, and stored at −80° C. until use.

6.3 Detection of Active 34-kDa HGFa in Plasma

Active 34-kDa HGFa was purified using the heparin-Sepharose chromatography described in previous studies, with some modifications. The detection was achieved by Western blotting (Miyazawa, K. et al., J. Biol. Chem. (1996) 271, 3615-3618). 200 µl of mouse plasma was diluted three times with 10 mM phosphate buffer (pH7.0) containing 0.05% CHAPS (Dojindo Molecular Technologies, Inc., Kumamoto, Japan) and 1 mM phenylmethanesulfonyl fluoride (PMSF; Nacalai Tesque Inc., Kyoto, Japan), and then loaded onto an HiTrap Heparin HP column (1 cm; Amersham Biosciences Corp., Tokyo, Japan) equilibrated with 10 mM sodium phosphate (pH 7.0) containing 0.05% CHAPS and 50 mM NaCl (Nacalai Tesque Inc., Kyoto, Japan). This column was washed with 4 ml of equilibration buffer containing 1 mM PMSF. Bound protein was eluted with 10 ml of 10 mM sodium phosphate (pH7.0) containing 0.05% CHAPS and 800 mM NaCl. Each eluted solution was concentrated to 40 µl by ultrafiltration using Centricon 30 (YM-30; Millipore Corp.). After denaturation with Laemmli's solution, the samples were subjected to sodium dodecyl sulfate (SDS)-polyacrylamide gel electrophoresis (PAGE) under reducing conditions preferable for Western blot analysis.

6.4 Determination of Plasma PCI Level After Hepatectomy

The plasma levels of human PCI expressed in PCI-Tg mice were determined by ELISA using an anti-human PCI monoclonal antibody (2 µg/ml) as a capture antibody (0.5 µg/ml), biotinylated rabbit anti-human PCI IgG as a detection antibody, and streptavidin-horse radish peroxidase conjugate, as described in a previous study (Hayashi, T. et al., J. Thromb. Haemost. (2004) 2, 949-961).

6.5 Detection of HGFa-PCI Complex in Plasma

To detect HGFa-PCI complex in mouse plasma, immunoprecipitation was carried out using an anti-human PCI monoclonal antibody (a gift from Chugai Pharmaceutical Co. Ltd., Tokyo, Japan) and Western blotting was carried out using an anti-HGFa antibody. Plasma (200 µl) from each of the Tg and WT mice were mixed at room temperature for one hour. Anti-human PCI IgG-Sepharose was prepared from 1 mg of anti-human PCI monoclonal antibody and 500 µl of BrCN-activated Shepharose 4B (Amersham Bioscience, Tokyo, Japan), according to the manufacturer's instructions. The Sepharose was then washed three times with Tris-buffered saline (TBS: 50 mM Tris-HCl (pH7.5) and 150 mM NaCl), and then another three times with TBS containing 1M NaCl. Then, the Sepharose was denatured in Laemmli's solution containing 2% SDS and 5% 2-mercaptoethanol and subjected to SDS-PAGE followed by Western blot analysis.

6.6 Tissue Homogenation and HGF Activation Assay of Remnant Livers

The buffer used for homogenation of liver samples was 20 mM Tris-HCl (pH7.5) containing 1% SDS, 5 mmol/l EDTA, 3 mmol/l EGTA, and protease inhibitor cocktail (Nacalai Tesque Inc., Kyoto, Japan). 0.2 g of liver tissue was added to 2 ml of ice-cold homogenation buffer and homogenated on ice for several minutes. The sample was then centrifuged at 15,000 rpm and 4° C. for 15 minutes. The resulting supernatant was collected and the concentration of protein in the sample was determined by bicinchoninic acid assay (BCA Protein Assay Kit; Pierce Chemical Co., Rockford, Ill.). The same amounts (200 μg) of homogenates were adjusted in volume, and then denatured in Laemmli's solution. The samples were then subjected to SDS-PAGE followed by immunoblotting using an anti-HGF antibody.

6.7 Western Blot Analysis

After SDS-PAGE, the gel was treated in transfer buffer containing 20 mM Tris, 150 mM lysine, and 20% methanol at 50 V overnight to transfer the samples to Immobile-P membrane. The membrane was then soaked in blotting buffer containing 10% skimmed milk for two hours. The blotting buffer was Dulbecco phosphate buffered saline (PBS; Sigma Chemical Co., St. Louis, Mo.) containing 0.05% TWEEN™ (polysorbate) 20. The primary antibody for HGFa detection was sc-1371 (Santa Cruz Biotechnology, Inc., Santa Cruz, Calif.). An antibody against HGF was obtained from the Institute of Immunology, Co. Ltd. (Tokyo, Japan). The primary antibody to HGFa was used at a 1:1,000 dilution. The antibody to HGF was used at a 1:500 dilution with blotting buffer containing 2% bovine serum albumin (BSA; Sigma Chemical Co., St. Louis, Mo.). The membrane was incubated with each primary antibody at room temperature for two hours, and then washed three times with blotting buffer containing 1% skimmed milk for 30 minutes in total. Next, the membrane was placed in blotting buffer containing 2% BSA, 1:5,000 diluted alkaline phosphatase-conjugated anti-goat IgG antibody (Promega Corp., Madison, Wis.) for HGFa detection, and 1:5,000 diluted anti-mouse IgG antibody (Promega Corp., Madison, Wis.) for HGF detection. After one hour of incubation at room temperature, the membrane was washed five times with Blotting buffer for 50 minutes in total, and immunostained using Western Blue Stabilized Substrate (Promega Corp., Madison, Wis.). The intensity of each positive band was determined using image analysis software: Image Gauge (Fuji Photo Film Co. Ltd., Japan).

6.8 Determination of Cytokine Levels

The concentrations of mouse TNF-α and IL-6 in plasma were determined using commercially available enzyme immunoassay kits (eBioscience, Kobe, Japan), according to the manufacturer's instructions.

6.9 BrdU Uptake Assay

Bromodeoxyuridine (BrdU) uptake was assayed 48 hours after hepatectomy. 50 mg/kg BrdU (Sigma Chemical Co., St. Louis, Mo.) was injected into peritoneal cavities, and the subjects were sacrificed after six hours. Liver samples were fixed with 4% formalin overnight, and then washed with Dulbecco phosphate buffered saline (PBS; Sigma Chemical Co., St. Louis, Mo.). The samples were then embedded in paraffin, and sliced into 5 mm sections. BrdU uptake was assessed by immunocytochemistry using an anti-BrdU monoclonal antibody (DakoCytomation Japan Co., Kyoto, Japan). BrdU-positive cells in four microscopic optical fields selected at random were counted in each sample. BrdU labeling index (BrdU L. I.) was calculated by the following formula: (number of BrdU-positive cells)/(number of total cells in the same area)×100(%).

6.10 Biochemical Analysis

The serum levels of AST, ALT, and bilirubin were each determined as liver necrosis markers using transaminase and bilirubin Test Wako (Wako Pure Chemical Industries Ltd., Osaka, Japan). The serum HA levels were assayed based on the sinusoidal cell function according to the manufacturer's instructions (Seikagaku Corp., Tokyo, Japan).

6.11 Administration of Anti-Human PCI Antibody

Prior to the hepatectomy experiments, to detect the influence of the antibodies, 100 μl of saline alone or saline containing 200 mg of neutralizing antibody against human PCI was administered into the caudal veins of both PCI-Tg and WT mice (n=6 in each group). The mice were sacrificed at predetermined times, and blood was collected as described above. The PCI activity in plasma was determined by a quantitative method for protein C activity using the chromogenic S-2366 substrate. 15 μl of the plasma samples were diluted three times with distilled water. 25 μl of the diluted samples were incubated with 50 μl of protein C activator (Protac; American Diagnostica Inc., Greenwich, Conn.) for ten minutes, and then 50 μl of S-2366 (concentration: 0.83 mg/ml; Daiichi Pure Chemicals Co. Ltd., Japan) was added thereto. The mixtures were incubated at 37° C. for ten minutes, and then 50 μl of 20% acetic acid was added to stop the reaction. Absorbance was read at 405 nm. After establishing the administration procedure, partial hepatectomies were performed, and the effect on liver regeneration was assessed in the same way as described above, using the weights nine days after surgery and BrdU uptake 48 hours after surgery.

6.12 Statistical Analysis

Data are presented as means and standard deviations. Each experiment was carried out three times at least. The differences in the means between two, three, or more groups were evaluated by Student t tests and variance analysis. Statistical significance was assumed with $p<0.05$.

Figure 7:
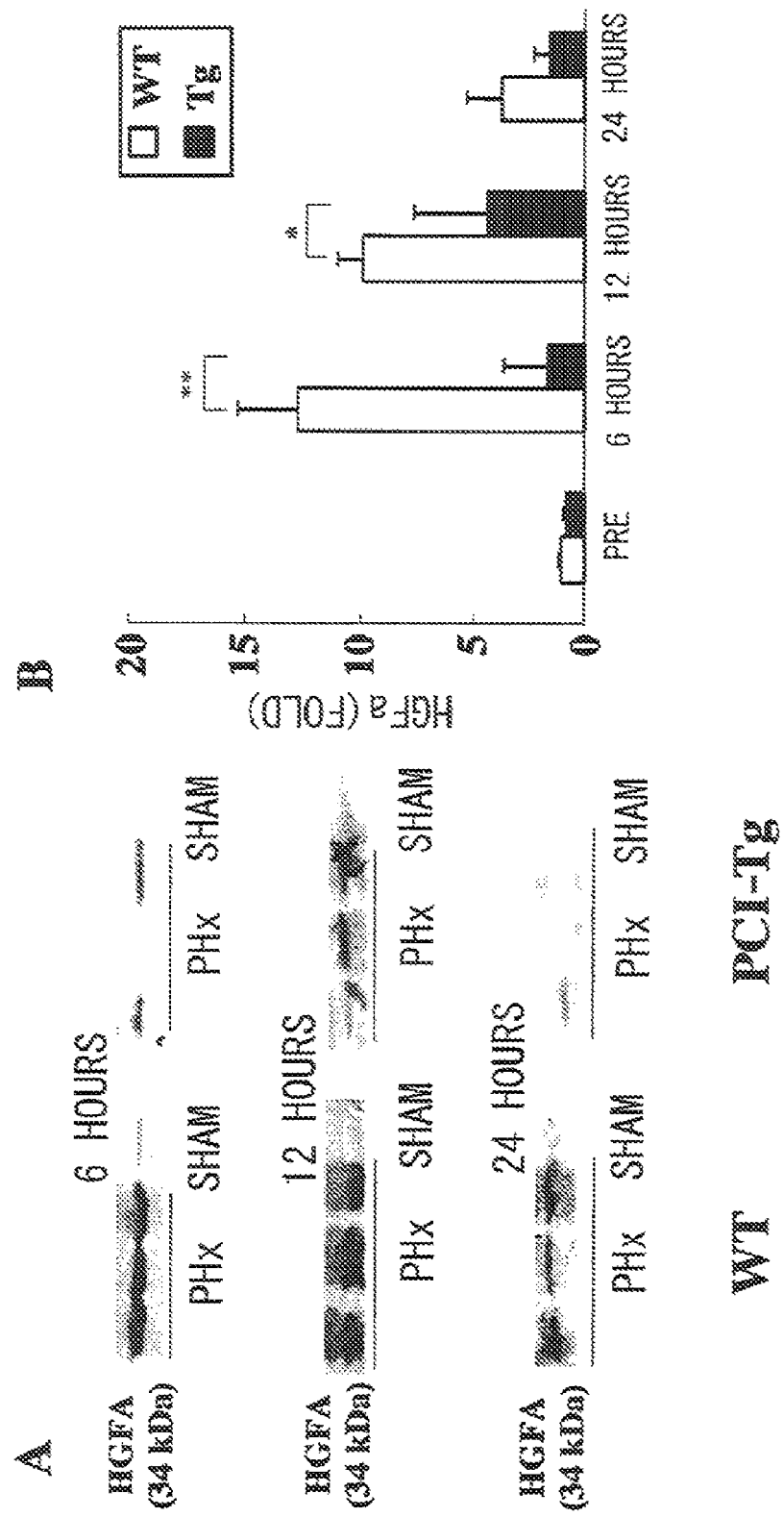
FIG. 7A is a photograph showing plasma HGFa activities in PCI-Tg and WT mice after partial hepatectomies. At a predetermined time, 200 µl of plasma was concentrated using a Heparin HP column. The sample was then analyzed by immunoblotting using anti-HGFa antibody as per the method described in the Examples.
FIG. 7B is a graph showing the results of density measurement and statistical analysis of the active HGFa shown to be in PCI-Tg and WT mice. These data were obtained by the method described in FIG. 7A. Each of the values for each of the conditions was normalized using plasma in untreated control WT mice. The data were presented as means±SD (n=6). *p<0.05, **p<0.01, in comparison with WT mice.
Figure 8:
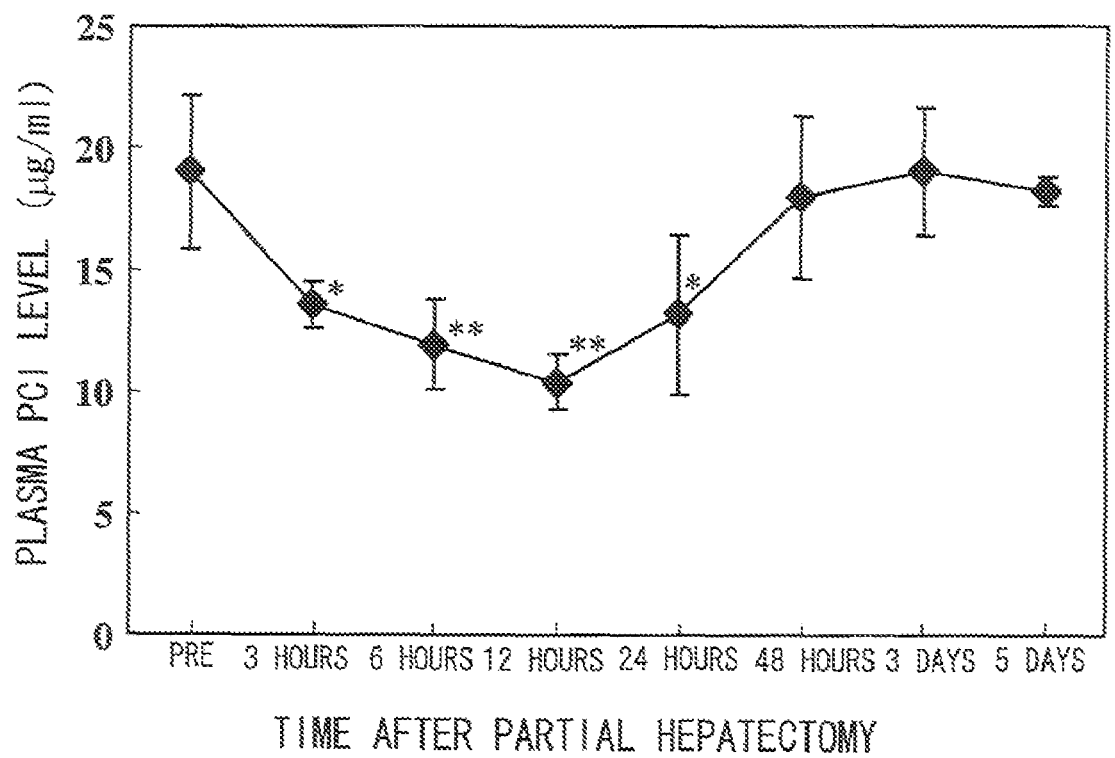
FIG. 8 is a graph showing changes in the plasma levels of human PCI in PCI-Tg mice after partial hepatectomies. The data were obtained using specific enzyme immunoassays. The data were presented as means±SD (n=6). *p<0.05, **p<0.01, in comparison with pre-surgery levels (pre).
Figure 9:
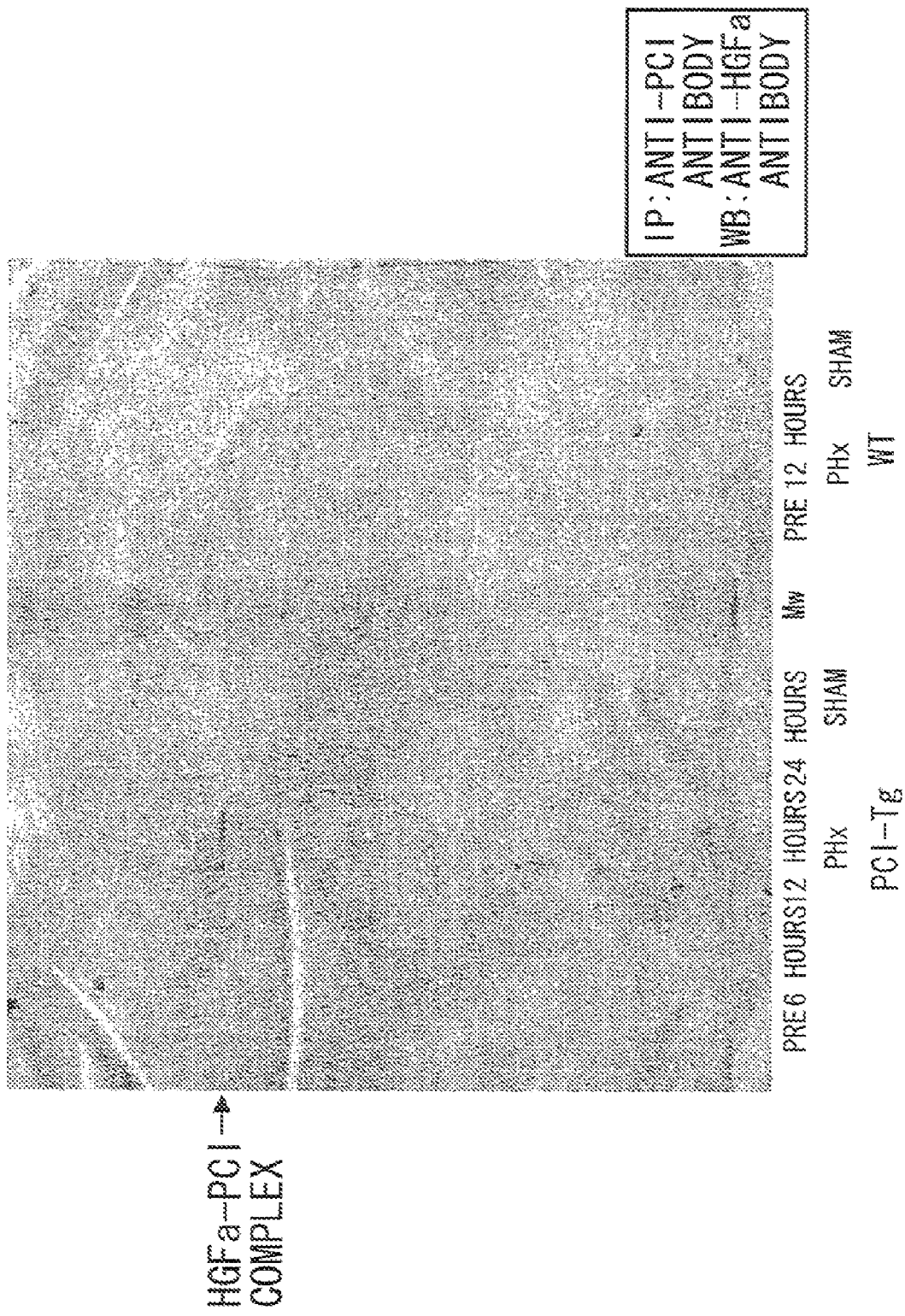
FIG. 9 is a photograph showing the results of detecting plasma HGFa-PCI complex in partially hepatectomized PCI-Tg mice by immunoprecipitation using anti-human PCI antibody and immunoblotting using anti-HGFa antibody. At a predetermined time, 200 µl of plasma was incubated with Sepharose immobilized with anti-human PCI IgG at room temperature for one hour. After thorough washing, anti-human PCI IgG-Sepharose beads were treated with Laemmli's solution, and the extract was subjected to SDS-PAGE, followed by immunoblotting using anti-HGFa antibody, as per the methods described in the Examples.
Figure 10:
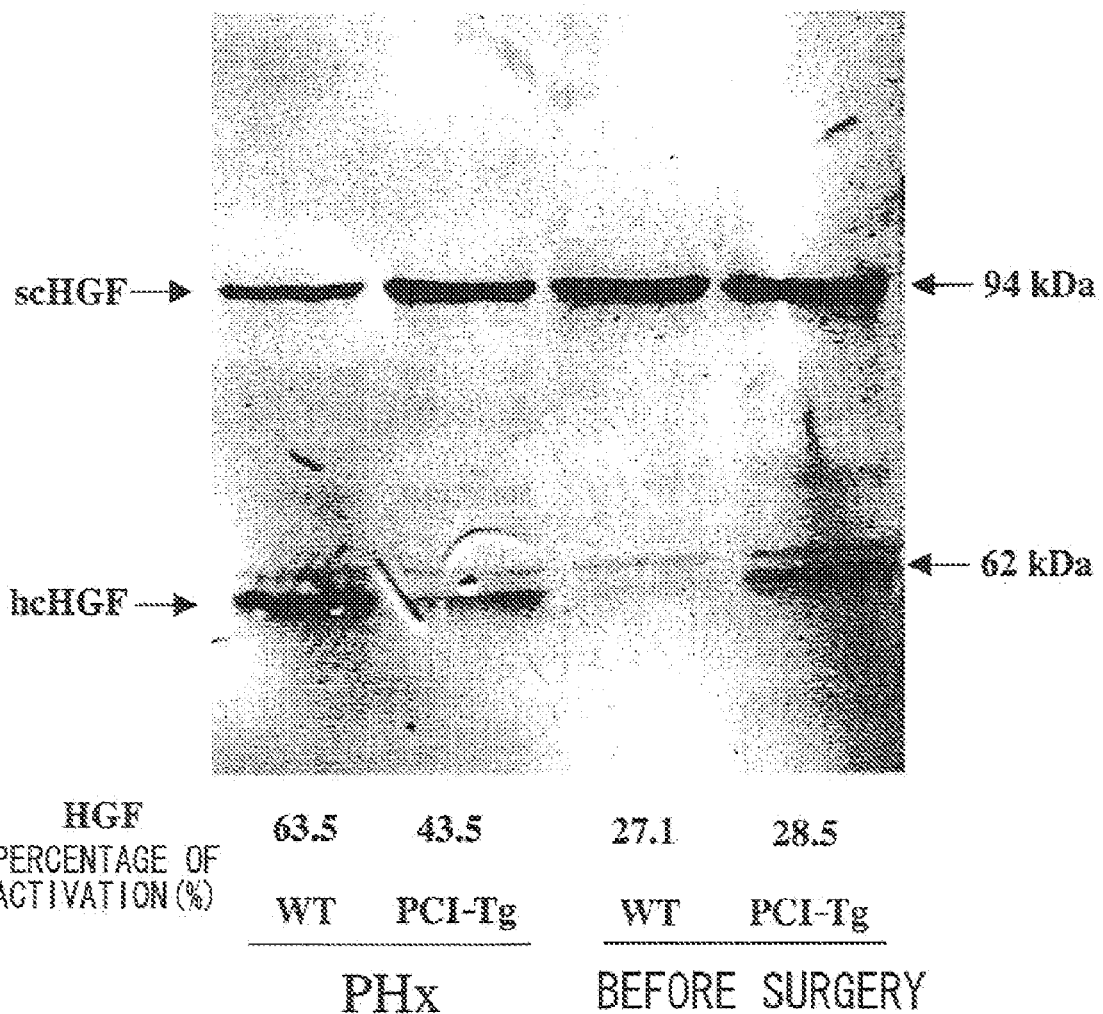
FIG. 10 is a photograph showing the results of Western blot analysis of the molecular form of HGF in extracts derived from liver tissue before and after hepatectomy. Active HGF (hcHGF) was detectable in the livers of PCI-Tg and WT mice post-hepatectomy, but the intensity of hcHGF was much lower in PCI-Tg mice than in WT mice. Meanwhile, inactive HGF (scHGF) was less abundant in PCI-Tg mice than in WT mice. The percentage of HGF activation was 43.5% in PCI-Tg mice, which was markedly lower than the 63.5% of WT mice.

6.13 Comparison of Plasma HGFa, PCI, and HGFa-PCI Levels, and of the Percentage of HGF Activation in Remnant Livers in the Earlier Stages after Hepatectomy The present inventors first determined plasma HGFa, PCI, and HGFa-PCI levels, and the percentage of HGF activation in remnant livers in the earlier stages after hepatectomy. Six hours after hepatectomy, plasma levels of 34-kDa HGFa in wild type mice were ten times greater than before surgery. However, HGFa levels did not increase in the PCI-Tg group. HGFa peaked twelve hours after surgery at levels five times greater than before surgery (FIG. 7). Furthermore, plasma PCI levels dropped rapidly after partial hepatectomy. PCI reached minimum levels 12 hours after surgery, and then recovered 48 hours after surgery (FIG. 8). In PCI-Tg mice, HGFa-PCI complex was found to be detectable 12 hours after surgery by immunoprecipitation using an anti-PCI antibody, and by Western blotting using an anti-HGFa antibody (FIG. 9). Thus, PCI-Tg mice had a lower percentage of remnant liver HGF activation (FIG. 10). These findings show that HGFa and PCI are consumed to form HGFa-PCI complex. Thus, HGF activation is suppressed in the remnant livers at earlier stages after partial hepatectomy in PCI-Tg mice.

6.14 Effect of PCI on Liver Regeneration

Figure 11:
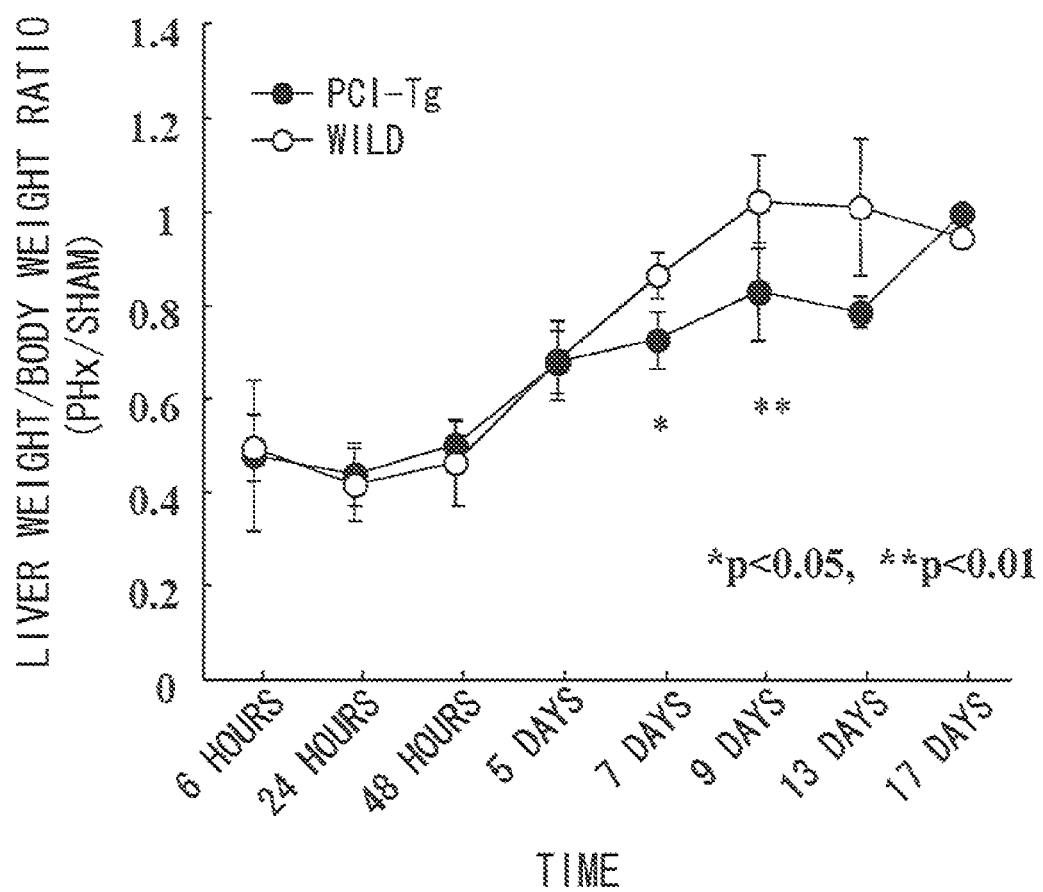
FIG. 11 shows a time course of the value obtained by dividing the liver weight/body weight ratio after partial hepatectomy by the liver weight/body weight ratio of mice which underwent a sham operation, using PCI transgenic mice (PCI-Tg) and wild type mice (Wild). The vertical axis indicates the liver weight/body weight ratio, and the horizontal axis indicates time.

The present inventors then assessed the effect of PCI on liver regeneration following partial hepatectomy. Specifically, the present inventors used PCI-Tg mice and their wild-type (WT) littermates to prepare a 70% partial hepatectomy model according to conventional methods. The right and left diaphragmatic lobes, and left visceral lobe were removed from the mice by surgery. Livers were collected six, 24, or 48 hours, or five, seven, nine, 13, or 17 days after hepatectomy. The wet weights and body weights were measured to determine organ/body weight ratios. The determined organ/body weight ratios were divided by the liver weight/body weight ratio of mice that underwent sham operations (non-hepatectomized mice anesthetized and laparotomized by the same procedure as used for the hepatectomized mice). The results are shown in FIG. 11. All mice in both groups survived. Liver regeneration started on post operation day (POD) 5 in both groups. Liver weight in WT mice was completely recovered on POD 9. On the other hand, in PCI-Tg mice liver weight did not completely recover and was about 80% that of the livers after sham operations. In PCI-Tg mice the process of liver regeneration was completed on POD 17 (FIG. 11; p<0.05, compared with WT mice on POD 7 and 9). BrdU uptake of remnant livers 48 hours after partial hepatectomy was quantified to assess the regeneration ability of remnant livers (FIG. 12). Whereas BrdU labeling index was 19.2±2.5% in WT mice, the index was 4.9±0.1% in PCI-Tg mice, and thus very low (p<0.01, compared with WT mice). The findings described above show that liver regeneration ability is poor in PCI-Tg mice compared to WT mice.

The levels of HGFa and PCI in plasma decreased in PCI-Tg mice over the 12 hours after hepatectomy (FIGS. 7 and 8). The HGFa-PCI complex was only detectable 12 hours after hepatectomy (FIG. 9). These data show that in PCI-Tg mice, HGFa and PCI are consumed to form HGFa-PCI complex at earlier stages after partial hepatectomy. This suppresses HGF activation in the remnant livers following partial hepatectomy (FIG. 10). Thus, the disorder reduces growth activity (FIG. 11), resulting in retardation of liver regeneration following partial hepatectomy (FIG. 12).

In humans, PCI is also detectable in plasma under normal conditions; 24 hours after hepatectomy the plasma levels of HGFa and PCI dropped rapidly and formation of HGFa-PCI complex increased (data not shown). These data suggest the possibility that PCI also inhibits HGFa and thus influences liver regeneration in the human model.

6.15 Assessment of the Difference in Damage Between PCI-Tg and WT Mice

Figure 13:
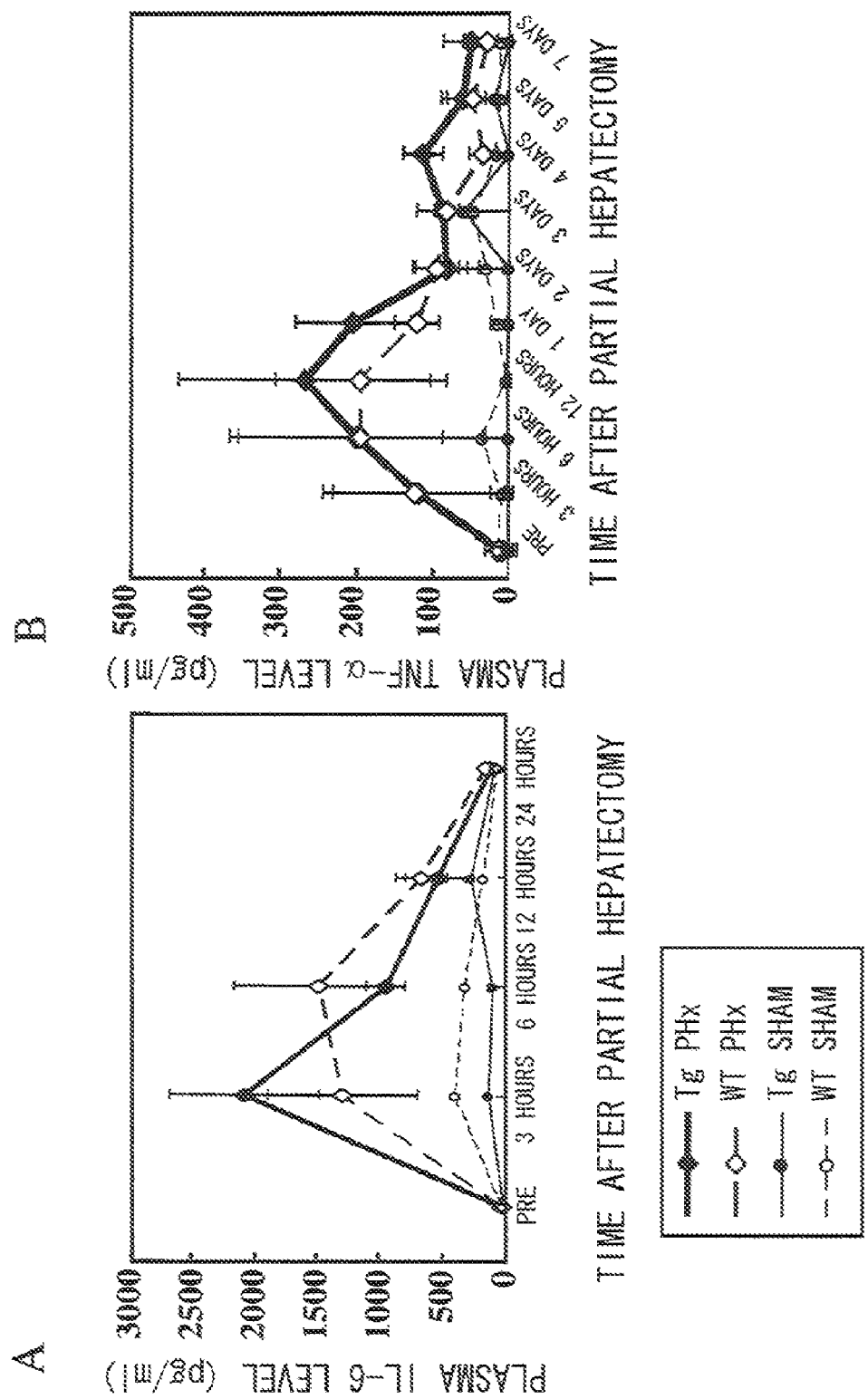
FIG. 13 is photographs and graphs showing changes in the plasma cytokine levels in PCI-Tg and WT mice after partial hepatectomies. Plasma IL-6 (FIG. 13A) and TNF-α (FIG. 13B) were quantified using specific enzyme immunoassays. The data were presented as means±SD (n=6).

The present inventors determined the levels of the proinflammatory cytokines, interleukin 6 (IL-6) and tumor necrosis factor (TNF)-α, to assess the difference in damages between the groups of PCI-Tg and WT mice after partial hepatectomy. As seen in FIG. 13A, the plasma IL-6 level increased rapidly and then returned to the normal range 24 hours after hepatectomy. Plasma IL-6 peaked more rapidly in PCI-Tg mice than in the group of WT mice; however, the levels were same in both groups. There was no significant difference in the TNF-α level of each group (FIG. 13B).

Figure 14:
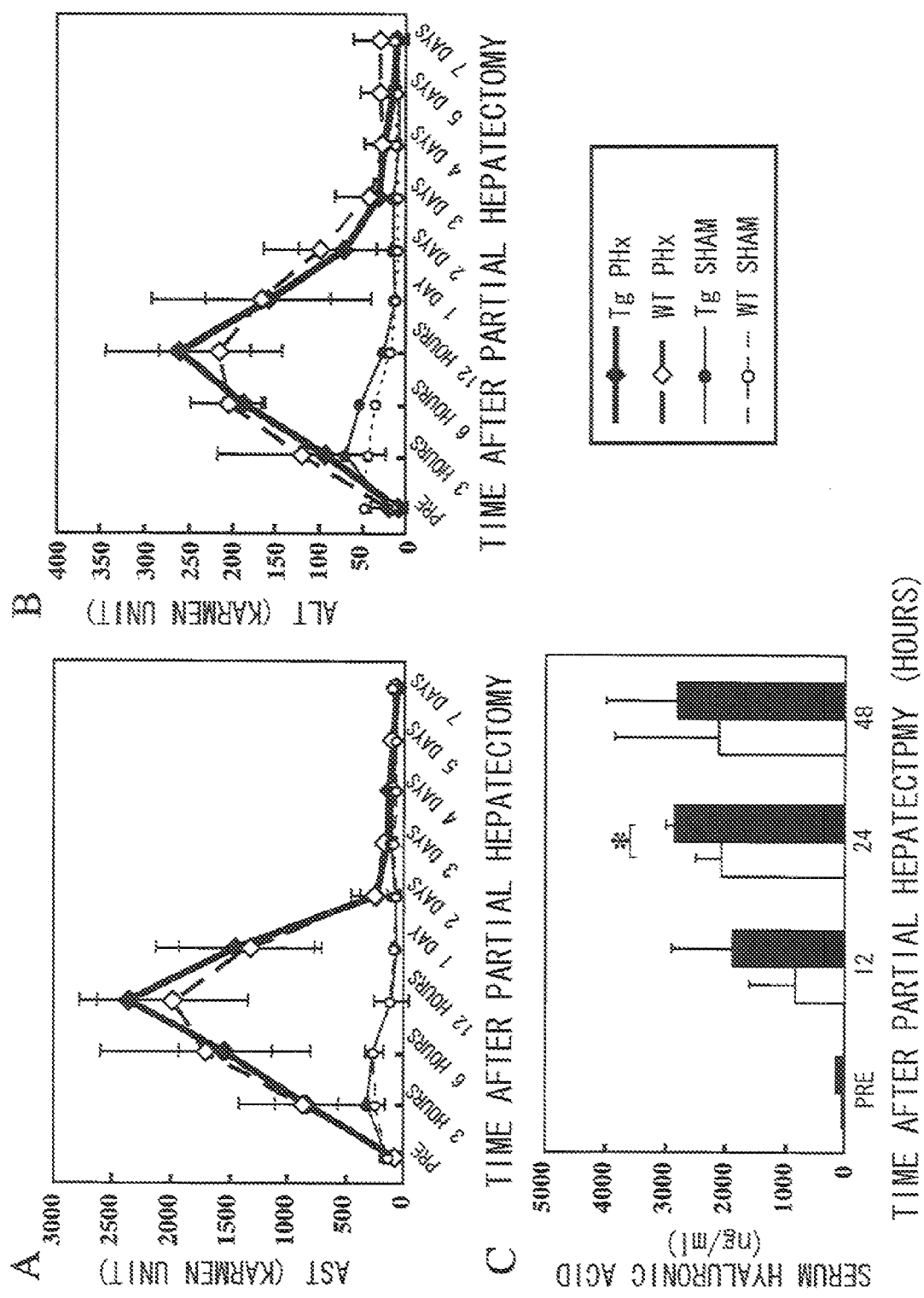
FIG. 14 is a graph showing changes in the levels of plasma transaminase and HA in PCI-Tg and WT mice after partial hepatectomies. The levels of AST (FIG. 14A), ALT (FIG. 14B), and HA (FIG. 14C) in plasma were determined using assay kits available in the market. The data were presented as means±SD (n=6). *p<0.05, in comparison with WT mice.

The present inventors then assessed long-term changes of the levels of transaminase, bilirubin, and plasma HA. FIGS. 14A and 14B respectively show that AST and ALT levels increased rapidly and peaked 12 hours after hepatectomy. However, there was no significant difference in each group. The (total and direct) bilirubin levels during the process of liver regeneration were in the normal ranges in the two groups (data not shown). The plasma HA level was higher at various time points after surgery in PCI-Tg mice than in WT mice (FIG. 14C; p<0.05 when compared with WT mice 12 hours after hepatectomy; no significant difference at other time points). These findings suggest that the damage to non-parenchymal cells progresses following partial hepatectomy in PCI-Tg mice.

6.16 Effect of Anti-PCI Antibody Administration on Liver Regeneration Disorders in PCI-Tg Mice Prior to this experiment, the present inventors assessed the effect of the antibody on PCI-Tg mice to determine an administration procedure. Specifically, PCI-Tg mice and their WT littermates underwent partial hepatectomies by the same method as described in Example 1. The PCI-neutralizing antibody (clone #19G8: described in WO 04/065418) was administered into the caudal vein at 10 mg/kg 12 hours before hepatectomy. The PCI-neutralizing antibody was also administered two, five, and eight days after hepatectomy. The buffer used was saline (physiological saline). Physiological saline was administered by the same method as a control group. Livers were collected nine days after hepatectomy, and their wet weights and body weights were measured to determine organ/body weight ratios.

Figure 15:
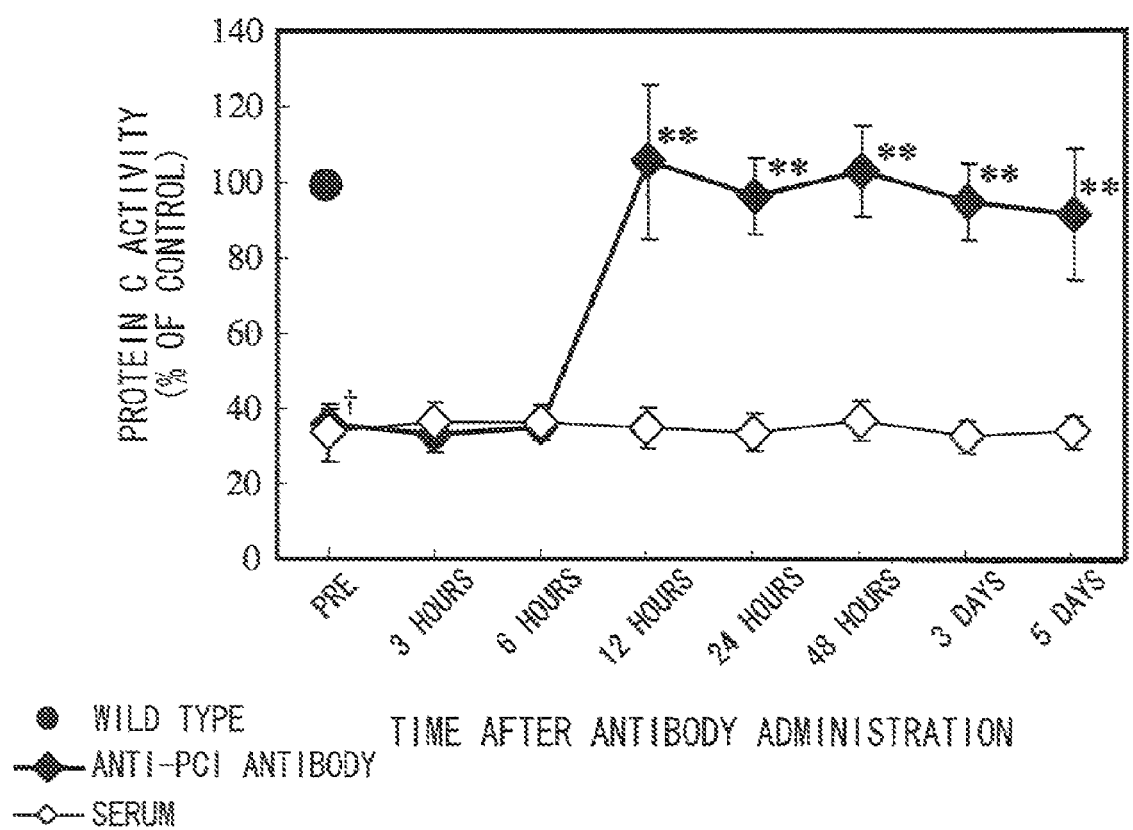
FIG. 15 is a graph showing changes in the effect of PCI on plasma protein C activity following antibody administration. The effect of PCI was determined using protein C activator and S-2366, as per the methods described in the Examples. The data were presented as means±SD (n=6). †p<0.01, in comparison with WT control plasma; **p<0.01, in comparison with the saline group.

Before injection, the aPC activity in plasma of PCI-Tg mice was found to be 35.8±4.3% of the activity in control plasma of WT mice (p<0.01). Twelve hours after administration, the aPC activity had already increased to about 100%. This effect lasted for a certain period, but decreased to about 70% up to five days after administration in some samples (FIG. 15). For this reason, the present inventors decided to administer the antibody every 72 hours, starting 12 hours before hepatectomy.

Figure 16:
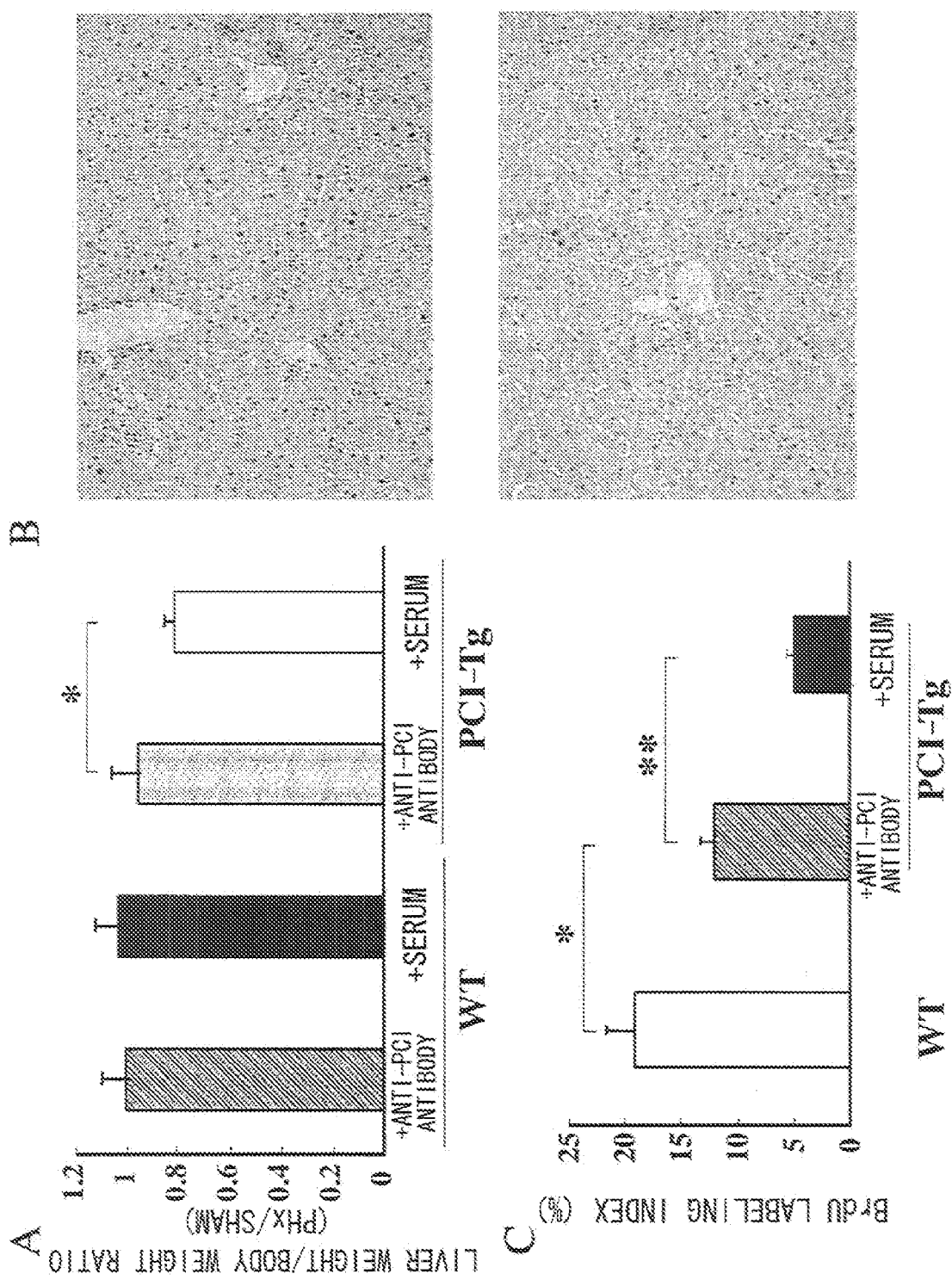
FIG. 16 is graphs and photographs showing the effect of anti-PCI antibody administration on liver regeneration in PCI-Tg mice after partial hepatectomies. Liver regeneration was assessed using the weight of the remnant liver (FIG. 16A) on POD 9 after partial hepatectomy, and BrdU uptake (FIGS. 16B and C) in the remnant liver 48 hours after partial hepatectomy. The data were presented as means±SD (n=6). *p<0.05, **p<0.01, in comparison with the anti-PCI antibody-administered group.

The determined organ/body weight ratios were divided by the liver weight/body weight ratios of mice that underwent sham operations and these results are shown in FIG. 16A. FIG. 16A suggests that, like WT mice, the liver weights of the mice administered with the antibody returned to pre-surgery condition on POD 9 (p<0.01, compared with the saline control). BrdU uptake also increased up to 12.1±1.2% when the antibody was administered (FIGS. 16B and 16C; p<0.01, compared with the saline group of PCI-Tg mice; p<0.05, compared with WT mice). In contrast, antibody administration produced no effect in WT mice. The data described above show that the administration of PCI-neutralizing antibody reduces the retardation of liver regeneration that was observed in PCI-Tg mice.

This suggests that therapeutic methods based on anti-PCI antibody administration can become favorable alternative therapeutic methods for liver regeneration treatment in the future.

INDUSTRIAL APPLICABILITY

The agents provided by the present invention can regulate liver regeneration. The agents for inducing and/or enhancing liver regeneration of the present invention, which comprise an anti-PCI antibody as an active ingredient, are effective against hepatic diseases, including various hepatitis, such as drug-induced hepatitis, fulminant hepatitis, and alcoholic hepatitis, and cirrhosis, all of which require liver regeneration. Meanwhile, there is a possibility of hyperregeneration when liver regeneration is enhanced by HGF, PCI-neutralizing antibody, or unknown methods. The agents for regulating liver regeneration, which comprise PCI as an active ingredient, can be used to regulate and control such liver hyperregeneration.

The present invention confirmed that anti-PCI antibodies enhance liver regeneration in a hepatectomy mouse model. This finding supports the report that PCI inhibits HGFa activity (Patent Document 2). The administration of an anti-PCI antibody is thought to enhance liver regeneration by neutralizing PCI activity and thus allowing HGFa-mediated formation of active HGF. Specifically, the administration of an anti-PCI antibody is expected to enhance in vivo production of active HGF. Thus, the agents for inducing and/or enhancing liver regeneration of the present invention, which comprise an anti-PCI antibody, are useful not only in liver regeneration but also in treating other diseases for which HGF is thought to be effective. Major diseases for which HGF can be used as a therapeutic agent include: (1) hepatic diseases, such as acute hepatitis, fatty liver, cirrhosis, fulminant hepatitis, and hepatic cancer; (2) vascular disorders, such as heart infarction and obstructive arteriosclerosis, and cardiovascular diseases, such as congestive cardiomyopathy; (3) bone diseases, such as osteoarthritis and rheumatic arthritis; and (4)

brain and neurological diseases, such as cerebral infarction and Parkinson's disease. In addition, there are reports on the involvement of HGF in curing injuries in the stomach, duodenum, and skin, and various symptoms of ischemia. The inducing and/or enhancing agents of the present invention are expected to be effective against these various diseases.

The invention claimed is:

1. A method for inducing or enhancing liver regeneration, which comprises administering an anti-protein C inhibitor (PCI) antibody to a subject in need of liver regeneration.

2. The method of claim 1, wherein the subject suffers from hepatitis.

3. The method of claim 1, wherein the subject suffers from cirrhosis.

4. The method of claim 1, wherein the subject suffers from fibrosis.

5. The method of claim 1, wherein the anti-PCI antibody is an antibody with the activity of neutralizing a PCI.

6. The method of claim 1, wherein the anti-PCI antibody is polyclonal.

7. The method of claim 1, wherein the anti-PCI antibody is monoclonal.

8. The method of claim 1, wherein the anti-PCI antibody is chimeric.

9. The method of claim 1, wherein the anti-PCI antibody is humanized.

10. A method for inducing or enhancing liver regeneration, which comprises administering an antigen-binding fragment of an anti-PCI antibody to a subject in need of liver regeneration.

11. The method of claim 10, wherein the antigen-binding fragment is a Fab fragment or F(ab')$_2$ fragment.

12. The method of claim 10, wherein the subject suffers from hepatitis.

13. The method of claim 10, wherein the subject suffers from cirrhosis.

14. The method of claim 10, wherein the subject suffers from fibrosis.

15. A method for inducing or enhancing liver regeneration, which comprises administering an anti-PCI scFv or sc(Fv)2 to a subject in need of liver regeneration.

16. The method of claim 15, wherein the subject suffers from hepatitis.

17. The method of claim 15, wherein the subject suffers from cirrhosis.

18. The method of claim 15, wherein the subject suffers from fibrosis.

* * * * *

```
                              SEQUENCE LISTING

<160> NUMBER OF SEQ ID NOS: 60

<210> SEQ ID NO 1
<211> LENGTH: 27
<212> TYPE: DNA
<213> ORGANISM: Artificial
<220> FEATURE:
<223> OTHER INFORMATION: Artificially synthesized sequence

<400> SEQUENCE: 1
acgaattcca ccatgcagct cttcctc                                           27

<210> SEQ ID NO 2
<211> LENGTH: 28
<212> TYPE: DNA
<213> ORGANISM: Artificial
<220> FEATURE:
<223> OTHER INFORMATION: Artificially synthesized sequence

<400> SEQUENCE: 2
ctggatcctc agggcggtt cactttgc                                           28

<210> SEQ ID NO 3
<211> LENGTH: 26
<212> TYPE: DNA
<213> ORGANISM: Artificial
<220> FEATURE:
<223> OTHER INFORMATION: Artificially synthesized sequence

<400> SEQUENCE: 3
ttggatccgg ggttcacttt gccaag                                            26

<210> SEQ ID NO 4
<211> LENGTH: 1237
<212> TYPE: DNA
<213> ORGANISM: Artificial
<220> FEATURE:
<223> OTHER INFORMATION: Artificially synthesized sequence encoding
      human PCI
<220> FEATURE:
<221> NAME/KEY: CDS
<222> LOCATION: (11)..(1228)

<400> SEQUENCE: 4
gaattccacc atg cag ctc ttc ctc ctc ttg tgc ctg gtg ctt ctc agc         49
           Met Gln Leu Phe Leu Leu Leu Cys Leu Val Leu Leu Ser
            1               5                   10 cct cag ggg gcc tcc ctt cac cgc cac cac ccc cgg gag atg aag aag        97
Pro Gln Gly Ala Ser Leu His Arg His His Pro Arg Glu Met Lys Lys
 15                  20                  25 aga gtc gag gac ctc cat gta ggt gcc acg gtg gcc ccc agc agc aga       145
Arg Val Glu Asp Leu His Val Gly Ala Thr Val Ala Pro Ser Ser Arg
 30                  35                  40                  45 agg gac ttt acc ttc gac ctc tac agg gtc ttg gct tcc gct gcc ccc       193
Arg Asp Phe Thr Phe Asp Leu Tyr Arg Val Leu Ala Ser Ala Ala Pro
                 50                  55                  60 agc cag aat atc ttc ttc tcc cct gtg agc atc tcc atg agc ctg gcc       241
Ser Gln Asn Ile Phe Phe Ser Pro Val Ser Ile Ser Met Ser Leu Ala
             65                  70                  75 atg ctc tcc ctg ggg gct ggg tcc agc aca aag atg cag atc ctg gag       289
```

```
              Met Leu Ser Leu Gly Ala Gly Ser Ser Thr Lys Met Gln Ile Leu Glu
                      80                  85                  90 ggc ctg ggc ctc aac ctc cag aaa agc tca gag gag gag ctg cac aga        337
Gly Leu Gly Leu Asn Leu Gln Lys Ser Ser Glu Glu Glu Leu His Arg
         95                 100                 105 ggc ttt cag cag ctc ctt cag gaa ctc aac cag ccc aga gat ggc ttc        385
Gly Phe Gln Gln Leu Leu Gln Glu Leu Asn Gln Pro Arg Asp Gly Phe
110                 115                 120                 125 cag ctg agc ctc ggc aat gcc ctt ttc acc gac ctg gtg gta gac ctg        433
Gln Leu Ser Leu Gly Asn Ala Leu Phe Thr Asp Leu Val Val Asp Leu
                130                 135                 140 cag gac acc ttc gta agt gcc atg aag acg ctg tac ctg gca gac act        481
Gln Asp Thr Phe Val Ser Ala Met Lys Thr Leu Tyr Leu Ala Asp Thr
            145                 150                 155 ttc ccc acc aac ttt agg gac tct gca ggg gcc atg aag cag atc aat        529
Phe Pro Thr Asn Phe Arg Asp Ser Ala Gly Ala Met Lys Gln Ile Asn
        160                 165                 170 gat tat gtg gca aag caa acg aag ggc aag att gtg gac ttg ctt aag        577
Asp Tyr Val Ala Lys Gln Thr Lys Gly Lys Ile Val Asp Leu Leu Lys
    175                 180                 185 aac ctc gat agc aat gcg gtc gtg atc atg gtg aat tac atc ttc ttt        625
Asn Leu Asp Ser Asn Ala Val Val Ile Met Val Asn Tyr Ile Phe Phe
190                 195                 200                 205 aaa gct aag tgg gag aca agc ttc aac cac aaa ggc acc caa gag caa        673
Lys Ala Lys Trp Glu Thr Ser Phe Asn His Lys Gly Thr Gln Glu Gln
                210                 215                 220 gac ttc tac gtg acc tcg gag act gtg gtg cgg gta ccc atg atg agc        721
Asp Phe Tyr Val Thr Ser Glu Thr Val Val Arg Val Pro Met Met Ser
            225                 230                 235 cgc gag gat cag tat cac tac ctc ctg gac cgg aac ctc tcc tgc agg        769
Arg Glu Asp Gln Tyr His Tyr Leu Leu Asp Arg Asn Leu Ser Cys Arg
        240                 245                 250 gtg gtg ggg gtc ccc tac caa ggc aat gcc acg gct ttg ttc att ctc        817
Val Val Gly Val Pro Tyr Gln Gly Asn Ala Thr Ala Leu Phe Ile Leu
    255                 260                 265 ccc agt gag gga aag atg cag cag gtg gag aat gga ctg agt gag aaa        865
Pro Ser Glu Gly Lys Met Gln Gln Val Glu Asn Gly Leu Ser Glu Lys
270                 275                 280                 285 acg ctg agg aag tgg ctt aag atg ttc aaa aag agg cag ctc gag ctt        913
Thr Leu Arg Lys Trp Leu Lys Met Phe Lys Lys Arg Gln Leu Glu Leu
                290                 295                 300 tac ctt ccc aaa ttc tcc att gag ggc tcc tat cag ctg gag aaa gtc        961
Tyr Leu Pro Lys Phe Ser Ile Glu Gly Ser Tyr Gln Leu Glu Lys Val
            305                 310                 315 ctc ccc agt ctg ggg atc agt aac gtc ttc acc tcc cat gct gat ctg       1009
Leu Pro Ser Leu Gly Ile Ser Asn Val Phe Thr Ser His Ala Asp Leu
        320                 325                 330 tcc ggc atc agc aac cac tca aat atc cag gtg tct gag atg gtg cac       1057
Ser Gly Ile Ser Asn His Ser Asn Ile Gln Val Ser Glu Met Val His
    335                 340                 345 aaa gct gtg gtg gag gtg gac gag tcg gga acc aga gca gcg gca gcc       1105
Lys Ala Val Val Glu Val Asp Glu Ser Gly Thr Arg Ala Ala Ala Ala
350                 355                 360                 365 acg ggg aca ata ttc act ttc agg tcg gcc cgc ctg aac tct cag agg       1153
Thr Gly Thr Ile Phe Thr Phe Arg Ser Ala Arg Leu Asn Ser Gln Arg
                370                 375                 380 cta gtg ttc aac agg ccc ttt ctg atg ttc att gtg gat aac aac atc       1201
Leu Val Phe Asn Arg Pro Phe Leu Met Phe Ile Val Asp Asn Asn Ile
            385                 390                 395 ctc ttc ctt ggc aaa gtg aac cgc ccc tgaggatcc                         1237
Leu Phe Leu Gly Lys Val Asn Arg Pro
```

```
Leu Phe Leu Gly Lys Val Asn Arg Pro
        400                 405

<210> SEQ ID NO 5
<211> LENGTH: 406
<212> TYPE: PRT
<213> ORGANISM: Artificial
<220> FEATURE:
<223> OTHER INFORMATION: Human PCI
<220> FEATURE:
<221> NAME/KEY: sig_peptide
<222> LOCATION: (1)..(19)

<400> SEQUENCE: 5

Met Gln Leu Phe Leu Leu Cys Leu Val Leu Leu Ser Pro Gln Gly
 1               5                  10                  15

Ala Ser Leu His Arg His His Pro Arg Glu Met Lys Lys Arg Val Glu
                20                  25                  30

Asp Leu His Val Gly Ala Thr Val Ala Pro Ser Ser Arg Arg Asp Phe
            35                  40                  45

Thr Phe Asp Leu Tyr Arg Val Leu Ala Ser Ala Ala Pro Ser Gln Asn
    50                  55                  60

Ile Phe Phe Ser Pro Val Ser Ile Ser Met Ser Leu Ala Met Leu Ser
65                  70                  75                  80

Leu Gly Ala Gly Ser Ser Thr Lys Met Gln Ile Leu Glu Gly Leu Gly
                85                  90                  95

Leu Asn Leu Gln Lys Ser Ser Glu Glu Glu Leu His Arg Gly Phe Gln
            100                 105                 110

Gln Leu Leu Gln Glu Leu Asn Gln Pro Arg Asp Gly Phe Gln Leu Ser
        115                 120                 125

Leu Gly Asn Ala Leu Phe Thr Asp Leu Val Val Asp Leu Gln Asp Thr
    130                 135                 140

Phe Val Ser Ala Met Lys Thr Leu Tyr Leu Ala Asp Thr Phe Pro Thr
145                 150                 155                 160

Asn Phe Arg Asp Ser Ala Gly Ala Met Lys Gln Ile Asn Asp Tyr Val
                165                 170                 175

Ala Lys Gln Thr Lys Gly Lys Ile Val Asp Leu Leu Lys Asn Leu Asp
            180                 185                 190

Ser Asn Ala Val Val Ile Met Val Asn Tyr Ile Phe Phe Lys Ala Lys
        195                 200                 205

Trp Glu Thr Ser Phe Asn His Lys Gly Thr Gln Glu Gln Asp Phe Tyr
    210                 215                 220

Val Thr Ser Glu Thr Val Val Arg Val Pro Met Met Ser Arg Glu Asp
225                 230                 235                 240

Gln Tyr His Tyr Leu Leu Asp Arg Asn Leu Ser Cys Arg Val Val Gly
                245                 250                 255

Val Pro Tyr Gln Gly Asn Ala Thr Ala Leu Phe Ile Leu Pro Ser Glu
            260                 265                 270

Gly Lys Met Gln Gln Val Glu Asn Gly Leu Ser Glu Lys Thr Leu Arg
        275                 280                 285

Lys Trp Leu Lys Met Phe Lys Arg Gln Leu Glu Leu Tyr Leu Pro
    290                 295                 300

Lys Phe Ser Ile Glu Gly Ser Tyr Gln Leu Glu Lys Val Leu Pro Ser
305                 310                 315                 320

Leu Gly Ile Ser Asn Val Phe Thr Ser His Ala Asp Leu Ser Gly Ile
                325                 330                 335

Ser Asn His Ser Asn Ile Gln Val Ser Glu Met Val His Lys Ala Val
```

```
                       340                 345                 350
Val Glu Val Asp Glu Ser Gly Thr Arg Ala Ala Ala Thr Gly Thr
                355                 360                 365

Ile Phe Thr Phe Arg Ser Ala Arg Leu Asn Ser Gln Arg Leu Val Phe
    370                 375                 380

Asn Arg Pro Phe Leu Met Phe Ile Val Asp Asn Ile Leu Phe Leu
385                 390                 395                 400

Gly Lys Val Asn Arg Pro
                405

<210> SEQ ID NO 6
<211> LENGTH: 1261
<212> TYPE: DNA
<213> ORGANISM: Artificial
<220> FEATURE:
<223> OTHER INFORMATION: Artificially synthesized DNA encoding human
      PCI with Flag-tag
<220> FEATURE:
<221> NAME/KEY: CDS
<222> LOCATION: (11)..(1258)

<400> SEQUENCE: 6
gaattccacc atg cag ctc ttc ctc ctc ttg tgc ctg gtg ctt ctc agc          49
           Met Gln Leu Phe Leu Leu Leu Cys Leu Val Leu Leu Ser
                 1               5                  10 cct cag ggg gcc tcc ctt cac cgc cac cac ccc cgg gag atg aag aag        97
Pro Gln Gly Ala Ser Leu His Arg His His Pro Arg Glu Met Lys Lys
     15                  20                  25 aga gtc gag gac ctc cat gta ggt gcc acg gtg gcc ccc agc agc aga       145
Arg Val Glu Asp Leu His Val Gly Ala Thr Val Ala Pro Ser Ser Arg
 30                  35                  40                  45 agg gac ttt acc ttc gac ctc tac agg gtc ttg gct tcc gct gcc ccc       193
Arg Asp Phe Thr Phe Asp Leu Tyr Arg Val Leu Ala Ser Ala Ala Pro
                 50                  55                  60 agc cag aat atc ttc ttc tcc cct gtg agc atc tcc atg agc ctg gcc       241
Ser Gln Asn Ile Phe Phe Ser Pro Val Ser Ile Ser Met Ser Leu Ala
             65                  70                  75 atg ctc tcc ctg ggg gct ggg tcc agc aca aag atg cag atc ctg gag       289
Met Leu Ser Leu Gly Ala Gly Ser Ser Thr Lys Met Gln Ile Leu Glu
         80                  85                  90 ggc ctg ggc ctc aac ctc cag aaa agc tca gag gag gag ctg cac aga       337
Gly Leu Gly Leu Asn Leu Gln Lys Ser Ser Glu Glu Glu Leu His Arg
     95                 100                 105 ggc ttt cag cag ctc ctt cag gaa ctc aac cag ccc aga gat ggc ttc       385
Gly Phe Gln Gln Leu Leu Gln Glu Leu Asn Gln Pro Arg Asp Gly Phe
110                 115                 120                 125 cag ctg agc ctc ggc aat gcc ctt ttc acc gac ctg gtg gta gac ctg       433
Gln Leu Ser Leu Gly Asn Ala Leu Phe Thr Asp Leu Val Val Asp Leu
                130                 135                 140 cag gac acc ttc gta agt gcc atg aag acg ctg tac ctg gca gac act       481
Gln Asp Thr Phe Val Ser Ala Met Lys Thr Leu Tyr Leu Ala Asp Thr
            145                 150                 155 ttc ccc acc aac ttt agg gac tct gca ggg gcc atg aag cag atc aat       529
Phe Pro Thr Asn Phe Arg Asp Ser Ala Gly Ala Met Lys Gln Ile Asn
        160                 165                 170 gat tat gtg gca aag caa acg aag ggc aag att gtg gac ttg ctt aag       577
Asp Tyr Val Ala Lys Gln Thr Lys Gly Lys Ile Val Asp Leu Leu Lys
    175                 180                 185 aac ctc gat agc aat gcg gtc gtg atc atg gtg aat tac atc ttc ttt       625
Asn Leu Asp Ser Asn Ala Val Val Ile Met Val Asn Tyr Ile Phe Phe
190                 195                 200                 205
```

```
aaa gct aag tgg gag aca agc ttc aac cac aaa ggc acc caa gag caa    673
Lys Ala Lys Trp Glu Thr Ser Phe Asn His Lys Gly Thr Gln Glu Gln
            210                 215                 220 gac ttc tac gtg acc tcg gag act gtg gtg cgg gta ccc atg atg agc    721
Asp Phe Tyr Val Thr Ser Glu Thr Val Val Arg Val Pro Met Met Ser
        225                 230                 235 cgc gag gat cag tat cac tac ctc ctg gac cgg aac ctc tcc tgc agg    769
Arg Glu Asp Gln Tyr His Tyr Leu Leu Asp Arg Asn Leu Ser Cys Arg
    240                 245                 250 gtg gtg ggg gtc ccc tac caa ggc aat gcc acg gct ttg ttc att ctc    817
Val Val Gly Val Pro Tyr Gln Gly Asn Ala Thr Ala Leu Phe Ile Leu
255                 260                 265 ccc agt gag gga aag atg cag cag gtg gag aat gga ctg agt gag aaa    865
Pro Ser Glu Gly Lys Met Gln Gln Val Glu Asn Gly Leu Ser Glu Lys
270                 275                 280                 285 acg ctg agg aag tgg ctt aag atg ttc aaa aag agg cag ctc gag ctt    913
Thr Leu Arg Lys Trp Leu Lys Met Phe Lys Lys Arg Gln Leu Glu Leu
            290                 295                 300 tac ctt ccc aaa ttc tcc att gag ggc tcc tat cag ctg gag aaa gtc    961
Tyr Leu Pro Lys Phe Ser Ile Glu Gly Ser Tyr Gln Leu Glu Lys Val
        305                 310                 315 ctc ccc agt ctg ggg atc agt aac gtc ttc acc tcc cat gct gat ctg   1009
Leu Pro Ser Leu Gly Ile Ser Asn Val Phe Thr Ser His Ala Asp Leu
    320                 325                 330 tcc ggc atc agc aac cac tca aat atc cag gtg tct gag atg gtg cac   1057
Ser Gly Ile Ser Asn His Ser Asn Ile Gln Val Ser Glu Met Val His
335                 340                 345 aaa gct gtg gtg gag gtg gac gag tcg gga acc aga gca gcg gca gcc   1105
Lys Ala Val Val Glu Val Asp Glu Ser Gly Thr Arg Ala Ala Ala Ala
350                 355                 360                 365 acg ggg aca ata ttc act ttc agg tcg gcc cgc ctg aac tct cag agg   1153
Thr Gly Thr Ile Phe Thr Phe Arg Ser Ala Arg Leu Asn Ser Gln Arg
            370                 375                 380 cta gtg ttc aac agg ccc ttt ctg atg ttc att gtg gat aac aac atc   1201
Leu Val Phe Asn Arg Pro Phe Leu Met Phe Ile Val Asp Asn Asn Ile
        385                 390                 395 ctc ttc ctt ggc aaa gtg aac cgc ccc gga tcc gac tac aag gac gac   1249
Leu Phe Leu Gly Lys Val Asn Arg Pro Gly Ser Asp Tyr Lys Asp Asp
    400                 405                 410 gat gac aag tga                                                    1261
Asp Asp Lys
    415

<210> SEQ ID NO 7
<211> LENGTH: 416
<212> TYPE: PRT
<213> ORGANISM: Artificial
<220> FEATURE:
<223> OTHER INFORMATION: Human PCI with Flag-tag
<220> FEATURE:
<221> NAME/KEY: sig_peptide
<222> LOCATION: (1)..(19)

<400> SEQUENCE: 7

Met Gln Leu Phe Leu Leu Leu Cys Leu Val Leu Leu Ser Pro Gln Gly
1               5                   10                  15

Ala Ser Leu His Arg His Pro Arg Glu Met Lys Lys Arg Val Glu
            20                  25                  30

Asp Leu His Val Gly Ala Thr Val Ala Pro Ser Ser Arg Arg Asp Phe
        35                  40                  45

Thr Phe Asp Leu Tyr Arg Val Leu Ala Ser Ala Ala Pro Ser Gln Asn
    50                  55                  60
```

```
Ile Phe Phe Ser Pro Val Ser Ile Ser Met Ser Leu Ala Met Leu Ser
 65                  70                  75                  80

Leu Gly Ala Gly Ser Ser Thr Lys Met Gln Ile Leu Glu Gly Leu Gly
                 85                  90                  95

Leu Asn Leu Gln Lys Ser Ser Glu Glu Leu His Arg Gly Phe Gln
            100                 105                 110

Gln Leu Leu Gln Glu Leu Asn Gln Pro Arg Asp Gly Phe Gln Leu Ser
            115                 120                 125

Leu Gly Asn Ala Leu Phe Thr Asp Leu Val Val Asp Leu Gln Asp Thr
        130                 135                 140

Phe Val Ser Ala Met Lys Thr Leu Tyr Leu Ala Asp Thr Phe Pro Thr
145                 150                 155                 160

Asn Phe Arg Asp Ser Ala Gly Ala Met Lys Gln Ile Asn Asp Tyr Val
                165                 170                 175

Ala Lys Gln Thr Lys Gly Lys Ile Val Asp Leu Leu Lys Asn Leu Asp
            180                 185                 190

Ser Asn Ala Val Val Ile Met Val Asn Tyr Ile Phe Phe Lys Ala Lys
        195                 200                 205

Trp Glu Thr Ser Phe Asn His Lys Gly Thr Gln Glu Gln Asp Phe Tyr
210                 215                 220

Val Thr Ser Glu Thr Val Val Arg Val Pro Met Met Ser Arg Glu Asp
225                 230                 235                 240

Gln Tyr His Tyr Leu Leu Asp Arg Asn Leu Ser Cys Arg Val Val Gly
                245                 250                 255

Val Pro Tyr Gln Gly Asn Ala Thr Ala Leu Phe Ile Leu Pro Ser Glu
            260                 265                 270

Gly Lys Met Gln Gln Val Glu Asn Gly Leu Ser Glu Lys Thr Leu Arg
        275                 280                 285

Lys Trp Leu Lys Met Phe Lys Lys Arg Gln Leu Glu Leu Tyr Leu Pro
290                 295                 300

Lys Phe Ser Ile Glu Gly Ser Tyr Gln Leu Glu Lys Val Leu Pro Ser
305                 310                 315                 320

Leu Gly Ile Ser Asn Val Phe Thr Ser His Ala Asp Leu Ser Gly Ile
                325                 330                 335

Ser Asn His Ser Asn Ile Gln Val Ser Glu Met Val His Lys Ala Val
            340                 345                 350

Val Glu Val Asp Glu Ser Gly Thr Arg Ala Ala Ala Thr Gly Thr
        355                 360                 365

Ile Phe Thr Phe Arg Ser Ala Arg Leu Asn Ser Gln Arg Leu Val Phe
370                 375                 380

Asn Arg Pro Phe Leu Met Phe Ile Val Asp Asn Asn Ile Leu Phe Leu
385                 390                 395                 400

Gly Lys Val Asn Arg Pro Gly Ser Asp Tyr Lys Asp Asp Asp Lys
                405                 410                 415

<210> SEQ ID NO 8
<211> LENGTH: 119
<212> TYPE: PRT
<213> ORGANISM: Mus musculus

<400> SEQUENCE: 8

Glu Val Gln Leu Gln Gln Ser Gly Ala Glu Leu Val Lys Pro Gly Ala
 1               5                  10                  15

Ser Val Lys Leu Ser Cys Thr Ala Ser Gly Phe Asp Ile Lys Asp Thr
             20                  25                  30
```

Phe Met His Trp Val Lys Gln Arg Pro Glu Gln Gly Leu Glu Trp Ile
        35                  40                  45

Gly Arg Ile Asp Tyr Val Asn Gly Asn Thr Lys Tyr Asp Pro Lys Phe
 50                  55                  60

Gln Gly Lys Ala Thr Ile Thr Gly Asp Thr Ser Asn Thr Ala Tyr
 65                  70                  75                  80

Leu Gln Leu Ser Ser Leu Thr Ser Glu Asp Thr Ala Val Tyr Tyr Cys
                85                  90                  95

Ala Arg Gly Gly Tyr Asp Val Arg Glu Phe Ala Tyr Trp Gly Gln Gly
                100                 105                 110

Thr Leu Val Thr Val Ser Ala
        115

<210> SEQ ID NO 9
<211> LENGTH: 119
<212> TYPE: PRT
<213> ORGANISM: Mus musculus

<400> SEQUENCE: 9

Glu Val Gln Leu Gln Gln Ser Gly Ala Glu Leu Val Lys Pro Gly Ala
 1               5                   10                  15

Ser Val Lys Leu Ser Cys Thr Ala Ser Gly Phe Asp Ile Lys Asp Thr
                20                  25                  30

Phe Met His Trp Val Lys Gln Arg Pro Glu Gln Gly Leu Glu Trp Ile
        35                  40                  45

Gly Arg Ile Asp Tyr Val Asn Gly Asn Thr Lys Tyr Asp Pro Lys Phe
 50                  55                  60

Gln Gly Lys Ala Thr Ile Thr Gly Asp Thr Ser Asn Thr Ala Tyr
 65                  70                  75                  80

Leu Gln Leu Ser Ser Leu Thr Ser Glu Asp Thr Ala Val Tyr Tyr Cys
                85                  90                  95

Ala Arg Gly Gly Tyr Asp Val Arg Glu Phe Ala Tyr Trp Gly Gln Gly
                100                 105                 110

Thr Leu Val Thr Val Ser Ala
        115

<210> SEQ ID NO 10
<211> LENGTH: 119
<212> TYPE: PRT
<213> ORGANISM: Mus musculus

<400> SEQUENCE: 10

Glu Val Gln Leu Gln Gln Ser Gly Ala Glu Leu Val Lys Pro Gly Ala
 1               5                   10                  15

Ser Val Lys Leu Ser Cys Thr Ala Ser Gly Phe Asp Ile Arg Asp Thr
                20                  25                  30

Phe Met His Trp Val Lys Gln Arg Pro Glu Gln Gly Leu Glu Trp Ile
        35                  40                  45

Gly Arg Ile Asp Leu Val Asn Val Asn Thr Lys Tyr Asp Pro Asn Phe
 50                  55                  60

Gln Asp Arg Ala Thr Ile Thr Ala Asp Thr Ser Ser Asn Thr Ala Tyr
 65                  70                  75                  80

Leu Gln Leu Thr Ser Leu Thr Ser Glu Asp Thr Ala Val Tyr Tyr Cys
                85                  90                  95

Ala Arg Gly Gly Tyr Asp Val Arg Glu Phe Ala Tyr Trp Gly Gln Gly
                100                 105                 110

Thr Leu Val Thr Val Ser Ala
        115

<210> SEQ ID NO 11
<211> LENGTH: 119
<212> TYPE: PRT
<213> ORGANISM: Mus musculus

<400> SEQUENCE: 11

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
            20                  25                  30

Tyr Ile His Trp Val Lys Gln Arg Pro Glu Gln Gly Leu Glu Trp Ile
        35                  40                  45

Gly Arg Ile Asp Leu Glu Lys Gly Asn Ile Ile Tyr Asp Pro Lys Phe
    50                  55                  60

Gln Gly Lys Asp Asn Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Gly Gly Tyr Asp Val Pro Ser Phe Ala Tyr Trp Gly Gln Gly
            100                 105                 110

Thr Leu Val Thr Val Ser Ala
        115

<210> SEQ ID NO 12
<211> LENGTH: 119
<212> TYPE: PRT
<213> ORGANISM: Mus musculus

<400> SEQUENCE: 12

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Lys Thr Leu Tyr
65                  70                  75                  80

Leu Gln Met Asn Lys Val Arg Ser Glu Asp Thr Ala Leu Tyr Tyr Cys
                85                  90                  95

Ala Arg Phe Phe Tyr Tyr Gly Thr Pro Asp Tyr Trp Gly Gln Gly Thr
            100                 105                 110

Thr Leu Thr Val Ser Ser Ala
        115

<210> SEQ ID NO 13
<211> LENGTH: 119
<212> TYPE: PRT
<213> ORGANISM: Mus musculus

<400> SEQUENCE: 13

Glu Val Lys Leu Leu Glu Ser Gly Gly Gly Leu Val Gln Pro Gly Gly
1               5                   10                  15

Ser Leu Lys Phe Ser Cys Glu Ala Ser Gly Phe Asp Phe Ser Arg Tyr
            20                  25                  30

```
Trp Met Ser Trp Val Arg Gln Ala Pro Gly Lys Gly Leu Glu Trp Ile
        35                  40                  45

Gly Glu Ile Asn Pro Asp Ser Ser Thr Ile Tyr Thr Ser Ser Leu
 50                  55                  60

Lys Asp Arg Phe Ile Ile Ser Arg Asp Asn Ala Lys Asn Thr Val Tyr
 65                  70                  75                  80

Leu Gln Met Ser Lys Val Arg Ser Glu Asp Thr Ala Leu Tyr Tyr Cys
                85                  90                  95

Ala Arg Leu Phe Tyr Tyr Gly Thr Pro Asp Tyr Trp Gly Gln Gly Thr
            100                 105                 110

Thr Leu Thr Val Ser Ser Ala
            115
```

```
<210> SEQ ID NO 14
<211> LENGTH: 120
<212> TYPE: PRT
<213> ORGANISM: Mus musculus

<400> SEQUENCE: 14

Gln Val Gln Leu Gln Gln Ser Gly Ala Glu Leu Val Lys Pro Gly Ala
 1               5                  10                  15

Ser Val Lys Met Ser Cys Lys Ala Phe Gly Tyr Thr Phe Thr Thr Tyr
                20                  25                  30

Pro Ile Glu Trp Met Lys Gln Asn His Gly Lys Ser Leu Glu Trp Ile
            35                  40                  45

Gly Lys Phe His Pro Asp Asn Asp Asp Thr Asn Tyr Asn Glu Lys Phe
 50                  55                  60

Lys Gly Lys Ala Lys Leu Thr Val Glu Lys Ser Ser Ser Thr Val Tyr
 65                  70                  75                  80

Leu Glu Leu Ser Arg Leu Thr Ser Asp Asp Ser Ala Val Tyr Tyr Cys
                85                  90                  95

Ala Arg Gly His Asp Tyr Asp Tyr Gly Met Asp Tyr Trp Gly Gln Gly
            100                 105                 110

Thr Ser Val Thr Val Ser Ser Ala
            115                 120
```

```
<210> SEQ ID NO 15
<211> LENGTH: 106
<212> TYPE: PRT
<213> ORGANISM: Mus musculus

<400> SEQUENCE: 15

Gln Ile Val Leu Thr Gln Ser Pro Ala Ile Met Ser Ala Ser Pro Gly
 1               5                  10                  15

Glu Lys Val Thr Ile Thr Cys Ser Ala Thr Ser Ser Leu Ile Tyr Met
                20                  25                  30

His Trp Phe Gln Gln Lys Pro Gly Ser Ser Pro Glu Leu Trp Ile Tyr
            35                  40                  45

Ser Thr Ser Asn Leu Ala Ser Gly Val Pro Ala Arg Phe Ser Gly Ser
 50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys
            100                 105
```

```
<210> SEQ ID NO 16
<211> LENGTH: 106
<212> TYPE: PRT
<213> ORGANISM: Mus musculus

<400> SEQUENCE: 16

Gln Ile Val Leu Thr Gln Ser Pro Ala Ile Met Ser Ala Ser Pro Gly
 1               5                  10                  15

Glu Lys Val Thr Ile Thr Cys Ser Ala Thr Ser Ser Leu Ile Tyr Met
            20                  25                  30

His Trp Phe Gln Gln Lys Pro Gly Ser Ser Pro Glu Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys
            100                 105

<210> SEQ ID NO 17
<211> LENGTH: 106
<212> TYPE: PRT
<213> ORGANISM: Mus musculus

<400> SEQUENCE: 17

Gln Ile Val Leu Thr Gln Ser Pro Ala Ile Met Ser Ala Ser Pro Gly
 1               5                  10                  15

Glu Lys Val Thr Ile Thr Cys Ser Ala Thr Ser Ser Leu Ile Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys
            100                 105

<210> SEQ ID NO 18
<211> LENGTH: 106
<212> TYPE: PRT
<213> ORGANISM: Mus musculus

<400> SEQUENCE: 18

Gln Ile Val Leu Thr Gln Ser Pro Ala Ile Met Ser Ala Ser Pro Gly
 1               5                  10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80
```

```
Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys
            100                 105

<210> SEQ ID NO 19
<211> LENGTH: 108
<212> TYPE: PRT
<213> ORGANISM: Mus musculus

<400> SEQUENCE: 19

Asp Ile Val Met Thr Gln Ser His Lys Phe Met Ser Ala Ser Val Gly
  1               5                  10                  15

Asp Arg Val Ser Ile Thr Cys Lys Ala Ser Gln Asp Val Ile Val Ala
                20                  25                  30

Val Ala Trp Tyr Gln Gln Lys Pro Gly Gln Ser Pro Glu Leu Leu Ile
            35                  40                  45

Tyr Ser Ala Ser Tyr Arg Tyr Thr Gly Val Pro Asp Arg Phe Thr Gly
 50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Ser Pro Pro
                85                  90                  95

Trp Thr Phe Gly Gly Gly Thr Lys Leu Glu Ile Lys
            100                 105

<210> SEQ ID NO 20
<211> LENGTH: 108
<212> TYPE: PRT
<213> ORGANISM: Mus musculus

<400> SEQUENCE: 20

Asp Ile Val Met Thr Gln Ser His Lys Phe Met Ser Thr Ser Val Gly
  1               5                  10                  15

Asp Arg Val Ser Ile Thr Cys Lys Ala Ser Gln Asp Val Ile Lys Ala
                20                  25                  30

Val Ala Trp Tyr Gln Gln Lys Pro Gly Gln Ser Pro Lys Leu Leu Ile
            35                  40                  45

Tyr Ser Thr Ser Tyr Arg Tyr Thr Gly Val Pro Asp Arg Phe Ser Gly
 50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Ser Pro Pro
                85                  90                  95

Trp Thr Phe Gly Gly Gly Thr Lys Leu Glu Ile Lys
            100                 105

<210> SEQ ID NO 21
<211> LENGTH: 111
<212> TYPE: PRT
<213> ORGANISM: Mus musculus

<400> SEQUENCE: 21

Asp Ile Val Leu Thr Gln Ser Pro Ala Ser Leu Ala Val Ser Leu Gly
  1               5                  10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Lys Pro Gly Gln Pro Pro
```

```
                  35                  40                  45
Lys Leu Leu Ile Tyr Gly Ala Ser Asn Leu Glu Ser Gly Thr Pro Ala
             50                  55                  60

Arg Phe Ser Gly Ser Gly Ser Gly Thr Asp Phe Thr Leu Asp Ile His
 65                  70                  75                  80

Pro Val Glu Glu Glu Asp Ala Ala Thr Tyr Tyr Cys Gln Gln Ser Asn
                 85                  90                  95

Glu Asp Pro Pro Thr Phe Gly Gly Gly Thr Lys Leu Glu Ile Thr
            100                 105                 110
```

<210> SEQ ID NO 22
<211> LENGTH: 5
<212> TYPE: PRT
<213> ORGANISM: Mus musculus

<400> SEQUENCE: 22

```
Asp Thr Phe Met His
 1               5
```

<210> SEQ ID NO 23
<211> LENGTH: 5
<212> TYPE: PRT
<213> ORGANISM: Mus musculus

<400> SEQUENCE: 23

```
Asp Tyr Tyr Ile His
 1               5
```

<210> SEQ ID NO 24
<211> LENGTH: 5
<212> TYPE: PRT
<213> ORGANISM: Mus musculus

<400> SEQUENCE: 24

```
Arg Tyr Trp Met Ser
 1               5
```

<210> SEQ ID NO 25
<211> LENGTH: 5
<212> TYPE: PRT
<213> ORGANISM: Mus musculus

<400> SEQUENCE: 25

```
Thr Tyr Pro Ile Glu
 1               5
```

<210> SEQ ID NO 26
<211> LENGTH: 17
<212> TYPE: PRT
<213> ORGANISM: Mus musculus

<400> SEQUENCE: 26

```
Arg Ile Asp Tyr Val Asn Gly Asn Thr Lys Tyr Asp Pro Lys Phe Gln
 1               5                  10                  15

Gly
```

<210> SEQ ID NO 27
<211> LENGTH: 17
<212> TYPE: PRT
<213> ORGANISM: Mus musculus

<400> SEQUENCE: 27

```
Arg Ile Asp Leu Val Asn Val Asn Thr Lys Tyr Asp Pro Asn Phe Gln
```

```
                  1               5                  10                  15
Asp

<210> SEQ ID NO 28
<211> LENGTH: 17
<212> TYPE: PRT
<213> ORGANISM: Mus musculus

<400> SEQUENCE: 28

Arg Ile Asp Leu Glu Lys Gly Asn Ile Ile Tyr Asp Pro Lys Phe Gln
  1               5                  10                  15

Gly

<210> SEQ ID NO 29
<211> LENGTH: 17
<212> TYPE: PRT
<213> ORGANISM: Mus musculus

<400> SEQUENCE: 29

Glu Ile Asn Pro Asp Ser Ser Thr Ile Asn Tyr Thr Pro Ser Leu Lys
  1               5                  10                  15

Asp

<210> SEQ ID NO 30
<211> LENGTH: 17
<212> TYPE: PRT
<213> ORGANISM: Mus musculus

<400> SEQUENCE: 30

Glu Ile Asn Pro Asp Ser Ser Thr Ile Thr Tyr Thr Ser Ser Leu Lys
  1               5                  10                  15

Asp

<210> SEQ ID NO 31
<211> LENGTH: 17
<212> TYPE: PRT
<213> ORGANISM: Mus musculus

<400> SEQUENCE: 31

Lys Phe His Pro Asp Asn Asp Thr Asn Tyr Asn Glu Lys Phe Lys
  1               5                  10                  15

Gly

<210> SEQ ID NO 32
<211> LENGTH: 10
<212> TYPE: PRT
<213> ORGANISM: Mus musculus

<400> SEQUENCE: 32

Gly Gly Tyr Asp Val Arg Glu Phe Ala Tyr
  1               5                  10

<210> SEQ ID NO 33
<211> LENGTH: 10
<212> TYPE: PRT
<213> ORGANISM: Mus musculus

<400> SEQUENCE: 33

Gly Gly Tyr Asp Val Pro Ser Phe Ala Tyr
  1               5                  10

<210> SEQ ID NO 34
```

```
<211> LENGTH: 9
<212> TYPE: PRT
<213> ORGANISM: Mus musculus

<400> SEQUENCE: 34

Phe Phe Tyr Tyr Gly Thr Pro Asp Tyr
1               5

<210> SEQ ID NO 35
<211> LENGTH: 9
<212> TYPE: PRT
<213> ORGANISM: Mus musculus

<400> SEQUENCE: 35

Leu Phe Tyr Tyr Gly Thr Pro Asp Tyr
1               5

<210> SEQ ID NO 36
<211> LENGTH: 10
<212> TYPE: PRT
<213> ORGANISM: Mus musculus

<400> SEQUENCE: 36

Gly His Asp Tyr Asp Tyr Gly Met Asp Tyr
1               5                   10

<210> SEQ ID NO 37
<211> LENGTH: 10
<212> TYPE: PRT
<213> ORGANISM: Mus musculus

<400> SEQUENCE: 37

Ser Ala Thr Ser Ser Leu Ile Tyr Met His
1               5                   10

<210> SEQ ID NO 38
<211> LENGTH: 10
<212> TYPE: PRT
<213> ORGANISM: Mus musculus

<400> SEQUENCE: 38

Ser Ala Ser Ser Ser Val Ser Tyr Met His
1               5                   10

<210> SEQ ID NO 39
<211> LENGTH: 11
<212> TYPE: PRT
<213> ORGANISM: Mus musculus

<400> SEQUENCE: 39

Lys Ala Ser Gln Asp Val Ile Val Ala Val Ala
1               5                   10

<210> SEQ ID NO 40
<211> LENGTH: 11
<212> TYPE: PRT
<213> ORGANISM: Mus musculus

<400> SEQUENCE: 40

Lys Ala Ser Gln Asp Val Ile Lys Ala Val Ala
1               5                   10

<210> SEQ ID NO 41
<211> LENGTH: 15
<212> TYPE: PRT
<213> ORGANISM: Mus musculus
```

```
<400> SEQUENCE: 41

Lys Ala Ser Gln Ser Val Asp Tyr Asp Gly Asp Ser Tyr Leu Asn
 1               5                  10                  15

<210> SEQ ID NO 42
<211> LENGTH: 11
<212> TYPE: PRT
<213> ORGANISM: Mus musculus

<400> SEQUENCE: 42

Ser Thr Ser Asn Leu Ala Ser Gly Val Pro Ala
 1               5                  10

<210> SEQ ID NO 43
<211> LENGTH: 11
<212> TYPE: PRT
<213> ORGANISM: Mus musculus

<400> SEQUENCE: 43

Ser Ala Ser Tyr Arg Tyr Thr Gly Val Pro Asp
 1               5                  10

<210> SEQ ID NO 44
<211> LENGTH: 11
<212> TYPE: PRT
<213> ORGANISM: Mus musculus

<400> SEQUENCE: 44

Ser Thr Ser Tyr Arg Tyr Thr Gly Val Pro Asp
 1               5                  10

<210> SEQ ID NO 45
<211> LENGTH: 11
<212> TYPE: PRT
<213> ORGANISM: Mus musculus

<400> SEQUENCE: 45

Gly Ala Ser Asn Leu Glu Ser Gly Thr Pro Ala
 1               5                  10

<210> SEQ ID NO 46
<211> LENGTH: 7
<212> TYPE: PRT
<213> ORGANISM: Mus musculus

<400> SEQUENCE: 46

Arg Ser Ser Tyr Pro Phe Thr
 1               5

<210> SEQ ID NO 47
<211> LENGTH: 8
<212> TYPE: PRT
<213> ORGANISM: Mus musculus

<400> SEQUENCE: 47

His Tyr Ser Ser Pro Pro Trp Thr
 1               5

<210> SEQ ID NO 48
<211> LENGTH: 7
<212> TYPE: PRT
<213> ORGANISM: Mus musculus

<400> SEQUENCE: 48
```

```
Ser Asn Glu Asp Pro Pro Thr
 1               5

<210> SEQ ID NO 49
<211> LENGTH: 5
<212> TYPE: PRT
<213> ORGANISM: Artificial
<220> FEATURE:
<223> OTHER INFORMATION: Heavy chain CDR1
<220> FEATURE:
<221> NAME/KEY: misc_feature
<222> LOCATION: (2)..(2)
<223> OTHER INFORMATION: "Xaa" in position 2 represents "Thr" or "Tyr"
<220> FEATURE:
<221> NAME/KEY: misc_feature
<222> LOCATION: (3)..(3)
<223> OTHER INFORMATION: "Xaa" in position 3 represents "Phe" or "Tyr"
<220> FEATURE:
<221> NAME/KEY: misc_feature
<222> LOCATION: (4)..(4)
<223> OTHER INFORMATION: "Xaa" in position 4 represents "Met" or "Ile"

<400> SEQUENCE: 49

Asp Xaa Xaa Xaa His
 1               5

<210> SEQ ID NO 50
<211> LENGTH: 17
<212> TYPE: PRT
<213> ORGANISM: Artificial
<220> FEATURE:
<223> OTHER INFORMATION: Heavy chain CDR2
<220> FEATURE:
<221> NAME/KEY: misc_feature
<222> LOCATION: (4)..(4)
<223> OTHER INFORMATION: "Xaa" in position 4 represents "Tyr" or "Leu"
<220> FEATURE:
<221> NAME/KEY: misc_feature
<222> LOCATION: (5)..(5)
<223> OTHER INFORMATION: "Xaa" in position 5 represents "Val" or "Glu"
<220> FEATURE:
<221> NAME/KEY: misc_feature
<222> LOCATION: (6)..(6)
<223> OTHER INFORMATION: "Xaa" in position 6 represents "Asn" or "Lys"
<220> FEATURE:
<221> NAME/KEY: misc_feature
<222> LOCATION: (7)..(7)
<223> OTHER INFORMATION: "Xaa" in position 7 represents "Gly" or "Val"
<220> FEATURE:
<221> NAME/KEY: misc_feature
<222> LOCATION: (9)..(9)
<223> OTHER INFORMATION: "Xaa" in position 9 represents "Thr" or "Ile"
<220> FEATURE:
<221> NAME/KEY: misc_feature
<222> LOCATION: (10)..(10)
<223> OTHER INFORMATION: "Xaa" in position 10 represents "Lys" or "Ile"
<220> FEATURE:
<221> NAME/KEY: misc_feature
<222> LOCATION: (14)..(14)
<223> OTHER INFORMATION: "Xaa" in position 14 represents "Lys" or "Asn"
<220> FEATURE:
<221> NAME/KEY: misc_feature
<222> LOCATION: (17)..(17)
<223> OTHER INFORMATION: "Xaa" in position 17 represents "Gly" or "Asp"

<400> SEQUENCE: 50

Arg Ile Asp Xaa Xaa Xaa Xaa Asn Xaa Xaa Tyr Asp Pro Xaa Phe Gln
 1               5                  10                  15

Xaa

<210> SEQ ID NO 51
<211> LENGTH: 10
<212> TYPE: PRT
<213> ORGANISM: Artificial
```

```
<220> FEATURE:
<223> OTHER INFORMATION: Heavy chain CDR3
<220> FEATURE:
<221> NAME/KEY: misc_feature
<222> LOCATION: (6)..(6)
<223> OTHER INFORMATION: "Xaa" in position 6 represents "Arg" or "Pro"
<220> FEATURE:
<221> NAME/KEY: misc_feature
<222> LOCATION: (7)..(7)
<223> OTHER INFORMATION: "Xaa" in position 7 represents "Glu" or "Ser"

<400> SEQUENCE: 51

Gly Gly Tyr Asp Val Xaa Xaa Phe Ala Tyr
1               5                   10

<210> SEQ ID NO 52
<211> LENGTH: 5
<212> TYPE: PRT
<213> ORGANISM: Artificial
<220> FEATURE:
<223> OTHER INFORMATION: Heavy chain CDR1

<400> SEQUENCE: 52

Arg Tyr Trp Met Ser
1               5

<210> SEQ ID NO 53
<211> LENGTH: 17
<212> TYPE: PRT
<213> ORGANISM: Artificial
<220> FEATURE:
<223> OTHER INFORMATION: Heavy chain CDR2
<220> FEATURE:
<221> NAME/KEY: misc_feature
<222> LOCATION: (10)..(10)
<223> OTHER INFORMATION: "Xaa" in position 10 represents "Asn" or "Thr"
<220> FEATURE:
<221> NAME/KEY: misc_feature
<222> LOCATION: (13)..(13)
<223> OTHER INFORMATION: "Xaa" in position 13 represents "Pro" or "Ser"

<400> SEQUENCE: 53

Glu Ile Asn Pro Asp Ser Ser Thr Ile Xaa Tyr Thr Xaa Ser Leu Lys
1               5                   10                  15

Asp

<210> SEQ ID NO 54
<211> LENGTH: 9
<212> TYPE: PRT
<213> ORGANISM: Artificial
<220> FEATURE:
<223> OTHER INFORMATION: Heavy chain CDR3
<220> FEATURE:
<221> NAME/KEY: misc_feature
<222> LOCATION: (1)..(1)
<223> OTHER INFORMATION: "Xaa" in position 1 represents "Phe" or "Leu"

<400> SEQUENCE: 54

Xaa Phe Tyr Tyr Gly Thr Pro Asp Tyr
1               5

<210> SEQ ID NO 55
<211> LENGTH: 10
<212> TYPE: PRT
<213> ORGANISM: Artificial
<220> FEATURE:
<223> OTHER INFORMATION: Light chain CDR1
<220> FEATURE:
<221> NAME/KEY: misc_feature
<222> LOCATION: (3)..(3)
<223> OTHER INFORMATION: "Xaa" in position 3 represents "Thr" or "Ser"
```

```
<220> FEATURE:
<221> NAME/KEY: misc_feature
<222> LOCATION: (6)..(6)
<223> OTHER INFORMATION: "Xaa" in position 6 represents "Leu" or "Val"
<220> FEATURE:
<221> NAME/KEY: misc_feature
<222> LOCATION: (7)..(7)
<223> OTHER INFORMATION: "Xaa" in position 7 represents "Ile" or "Ser"

<400> SEQUENCE: 55

Ser Ala Xaa Ser Ser Xaa Xaa Tyr Met His
1               5                   10

<210> SEQ ID NO 56
<211> LENGTH: 11
<212> TYPE: PRT
<213> ORGANISM: Artificial
<220> FEATURE:
<223> OTHER INFORMATION: Light chain CDR2

<400> SEQUENCE: 56

Ser Thr Ser Asn Leu Ala Ser Gly Val Pro Ala
1               5                   10

<210> SEQ ID NO 57
<211> LENGTH: 7
<212> TYPE: PRT
<213> ORGANISM: Artificial
<220> FEATURE:
<223> OTHER INFORMATION: Light chain CDR3

<400> SEQUENCE: 57

Arg Ser Ser Tyr Pro Phe Thr
1               5

<210> SEQ ID NO 58
<211> LENGTH: 11
<212> TYPE: PRT
<213> ORGANISM: Artificial
<220> FEATURE:
<223> OTHER INFORMATION: Light chain CDR1
<220> FEATURE:
<221> NAME/KEY: misc_feature
<222> LOCATION: (8)..(8)
<223> OTHER INFORMATION: "Xaa" in position 8 represents "Val" or "Lys"

<400> SEQUENCE: 58

Lys Ala Ser Gln Asp Val Ile Xaa Ala Val Ala
1               5                   10

<210> SEQ ID NO 59
<211> LENGTH: 11
<212> TYPE: PRT
<213> ORGANISM: Artificial
<220> FEATURE:
<223> OTHER INFORMATION: Light chain CDR2
<220> FEATURE:
<221> NAME/KEY: misc_feature
<222> LOCATION: (2)..(2)
<223> OTHER INFORMATION: "Xaa" in position 2 represents "Ala" or "Thr"

<400> SEQUENCE: 59

Ser Xaa Ser Tyr Arg Tyr Thr Gly Val Pro Asp
1               5                   10

<210> SEQ ID NO 60
<211> LENGTH: 8
<212> TYPE: PRT
<213> ORGANISM: Artificial
<220> FEATURE:
```

```
<223> OTHER INFORMATION: Light chain CDR3

<400> SEQUENCE: 60

His Tyr Ser Ser Pro Pro Trp Thr
  1               5
```